US008030052B2

(12) United States Patent
Watanabe et al.

(10) Patent No.: US 8,030,052 B2
(45) Date of Patent: Oct. 4, 2011

(54) MIDECAMYCIN HYPER PRODUCING STRAIN

(75) Inventors: Manabu Watanabe, Odawara (JP); Masaaki Nakahashi, Odawara (JP)

(73) Assignee: Meiji Seika Kaisha, Ltd., Tokyo (JP)

( * ) Notice: Subject to any disclaimer, the term of this patent is extended or adjusted under 35 U.S.C. 154(b) by 223 days.

(21) Appl. No.: 11/391,444

(22) Filed: Mar. 29, 2006

(65) Prior Publication Data

US 2006/0223146 A1 Oct. 5, 2006

(30) Foreign Application Priority Data

Mar. 31, 2005 (JP) ............................. P. 2005-101836

(51) Int. Cl.
*C12N 1/21* (2006.01)
*C12N 15/00* (2006.01)
*C07H 21/04* (2006.01)

(52) U.S. Cl. ................ 435/252.3; 435/183; 435/252.35; 536/23.2; 536/23.7; 536/23.1

(58) Field of Classification Search ............... 435/252.3, 435/183, 252.35; 536/23.2, 23.7, 23.1
See application file for complete search history.

(56) References Cited

U.S. PATENT DOCUMENTS

| 3,761,588 A * | 9/1973 | Tsuruoka et al. ............. 424/121 |
| 7,070,980 B2 * | 7/2006 | Midoh et al. ................ 435/252.3 |
| 2004/0091975 A1 | 5/2004 | Midoh et al. | |

FOREIGN PATENT DOCUMENTS

JP 2004-049100 A 2/2004

OTHER PUBLICATIONS

Guo et al., Protein tolerance to random amino acid change. Proc Natl Acad Sci U S A. Jun. 22, 2004;101(25):9205-10. Epub Jun. 14, 2004.*
Kimchi-Sarfaty C et al., A "silent" polymorphism in the MDR1 gene changes substrate specificity. Science. Jan. 26, 2007;315(5811):525-8.*
Wiley et al., 1990, Biochemistry, pp. 126-129.*
Stefano Donadio, et al., "Modular Organization of Genes Required for Complex Polyketide Biosynthesis," Research Articles, May 3, 1991, pp. 675-679.
Torsten Schwecke, et al., "The biosynthetic gene cluster for the polyketide immunosuppressant rapamycin," Proc. Natl. Acad. Sci. USA, vol. 92, pp. 7839-7843, Aug. 1995, Biochemistry.
Axel A. Brakhage, "Molecular Regulation of β-Lactam Biosynthesis in Filamentous Fungi," Microbiology and Molecular Biology Reviews, Sep. 1998, pp. 547-585, vol. 62, No. 3.
Hans Weiher, et al., "Segment-specific mutagenesis: Extensive mutagenesis of a *lac* promoter/operator element," Proc. Natl. Acad. Sci. USA, vol. 79, pp. 1408-1412, Mar. 1982, Biochemistry.
Thomas Kunkel, "Rapid and efficient site-specific mutagenesis without phenotypic selection," Proc. Natl. Acad. Sci. USA, vol. 82, pp. 488-492, Jan. 1985, Genetics.
CR Hutchinson et al., "Genetic engineering of doxorubicin production in *Streptomyces peucetius*: a review," Journal of Industrial Microbiology & Biotechnology (1999) 23, 647-652.
Omoto et al.; "Modifications of a Macrolide Antibiotic Midecamycin (SF-837)"; The Journal of Antibiotics; May 1976; pp. 536-548; vol. 29, No. 5.
Yoshida et al.; "Bacteriological Evaluation of Midecamycin Acetate and its Metabolites"; The Japanese Journal of Antibiotics; Jun. 1982, pp. 1462-1475; vol. 35, No. 6.
MacNeil et al.; Complex organization of the *Streptomyces avermitilis* genes encoding the avermectin polyketide synthase; Gene; 1992; pp. 119-125; vol. 115.
Summers et al.; "Sequencing and mutagenesis of genes from the erythromycin biosynthetic gene cluster of *Saccharopolyspora erythraea* that are involved in L-mycarose and D-desosamine production"; Microbiology; 1997; pp. 3251-3262; vol. 143.
Gaisser et al.; "Analysis of seven genes from the eryAI-eryK region of the erythromycin biosynthetic gene cluster in *Saccharopolyspora erythraea* "; Mol. Gen. Genet.; 1997; pp. 239-251; vol. 256.
L. A. Merson-Davies and E. Cundliffe; "Analysis of five tylosin biosynthetic genes from the tylIBA region of the *Streptomyces fradiae* genome"; Molecular Microbiology; 1994; pp. 349-355; vol. 13, No. 2.
J. Kennedy and G. Turner; "δ(L-$_x$-Aminoadipyl)-L-cysteinyl-D-valine synthetase is a rate limiting enzyme for penicillin production in *Aspergillus nidulans*"; Mol. Gen. Genet.; 1996; pp. 189-197; vol. 253.
R. H. Baltz; "Molecular Genetic Approaches to Yield Improvement in Actinomycetes"; Lilly Research Laboratories, Eli Lilly and Company, Indianapolis, IN; pp. 49-62.
Bierman et al.; "Plasmid cloning vectors for the conjugal transfer of DNA from *Escherichia coli* to Streptomyces spp."; Gene; 1992; pp. 43-49; vol. 116.
H. Shiraishi and Y. Shimura; "A rapid and efficient method for targeted random mutagenesis"; Gene; 1988; pp. 313-319; vol. 64.
Ito et al.; "A general method for introducing a series of mutations into cloned DNA using the polymerase chain reaction"; Gene; 1991; pp. 67-70; vol. 102.
Hashimoto-Gotoh et al.; "An oligodeoxyribonucleotide-directed dual amber method for site-directed mutagenisis"; Gene; 1995; pp. 271-275; vol. 152.
T.-J. Shen et al.; "A marker-coupled method for site-directed mutagenesis"; Gene; 1991; pp. 73-77; vol. 103.

(Continued)

*Primary Examiner* — Maria Leavitt
(74) *Attorney, Agent, or Firm* — Sughrue Mion, PLLC

(57) ABSTRACT

A midecamycin hyper producing strain having improved productivity of midecamycin which is a member of macrolide antibiotics, and a method for producing midecamycins using the strain are provided. The midecamycin producing actinomycetes comprises a midecamycin biosynthesis gene or a homologue thereof, wherein at least one module in a polyketide synthase gene of a midecamycin biosynthesis gene or partial sequences of the at least one module, is substituted so as to encode the corresponding amino acid sequences of the other module.

2 Claims, 3 Drawing Sheets

OTHER PUBLICATIONS

Notification of First Office Action issued in counterpart Chinese Application No. 200610073849.7 dated Jan. 22, 2010.

Japanese Office Action issued on Sep. 14, 2010 in the corresponding Japanese Patent Application No. 2005-101836.

* cited by examiner

| Midecamycin | R₁ | R₂ | R₃ | X |
|---|---|---|---|---|
| A₁ | -COCH₂CH₃ | -CHO | -COCH₂CH₃ | -OH |
| A₂ | -COCH₂CH₃ | -CHO | -COCH₂CH₂CH₃ | -OH |
| A₃ | -COCH₂CH₃ | -CHO | -COCH₂CH₃ | =O |
| B | -COCH₃ | -CHO | -COCH₂CH₃ | -OH |
| DH | -COCH₂CH₃ | -CH₂OH | -COCH₂CH₃ | -OH |
| E | -COCH₂CH₂CH₃ | -CHO | -COCH₂CH₃ | -OH |
| CH₃ | -COCH₂CH₃ | -CH₃ | -COCH₂CH₂CH₃ or -COCH(CH₃)₂ | -OH |

Fig. 2

| Strain name | Midecamycin productivity(μm/ml) |
|---|---|
| Streptomyces mycarofaciens SF 837 (ATCC 21454) | 60 |
| \| | |
| Streptomyces mycarofaciens 938-15 | 798 |
| \| | |
| Streptomyces mycarofaciens 1149-38 | 1127 |
| \| | |
| Streptomyces mycarofaciens 1251-2 | 1127 |

Fig. 3

```
wild_ks2  EPIAVVGMACRYPGGVAAPEELWDLVAGGGHAISPLPANRGWDLEGLYDPEPGVPGKSYVREGGFLHGAAEFDAEFFGVS  2662
          ||||||||||||||||||| |||||  |  |||| || ||||  ||||||  |   | ||||||||||||||||||||||
hyp_ks3   EPIAVVGMACRYPGGVAAPEDLWDLVVAGTDAISPFPADRGWDVEGLYDPDPDAVGRSYVREGGFLHGAAEFDAEFFGVS  114
          ||||||||||||||||||||||||||||||||||||||||||||||||||||||||||||||||||||||||||||||||
wild_ks3  EPIAVVGMACRYPGGVAAPEDLWDLVVAGTDAISPFPADRGWDVEGLYDPDPDAVGRSYVREGGFLHGAAEFDAEFFGVS  114 wild_ks2  PREAAAMDPQQRLLLETSWEALERAGIVPAALRGTRTGVFTGISQQDYAAQLGDAAETYGGHVLTGNLGSVVSGRVAYSL  2742
          ||||||||||||||||||||||||||||||||||||||||||||||||||||||||||||||||||||||||||||||||
hyp_ks3   PREAAAMDPQQRLLLETSWEALERAGIVPAALRGTRTGVFTGISQQDYAAQLGDAAETYGGHVLTGNLGSVVSGRVAYSL  194
          ||||||||||||||||||||||||||||||||||||||||  ||  |  |  | |   |  | || ||||||||
wild_ks3  PREAAAMDPQQRLLLETSWEALERAGIVPAALRGTRTGVFTGVMYDDYGSQFDSAPPEYEGYLVNGSAGSIASGRVAYSL  194 wild_ks2  GLEGPALTVDTACSSSLVALHLAVQSLRRGECDMALAGGVTVMATPTVFVEFSRQRGLASDGRCKAFAEGADGTAWGEGV  2822
          ||||||||||||||||||||||||||||||||||||||||||||||||||||||||||||||||||||||||||||||||
hyp_ks3   GLEGPALTVDTACSSSLVALHLAVQSLRRGECDMALAGGVTVMATPTVFVEFSRQRGLASDGRCKAFAEGADGTAWGEGV  274
          |||||||||||||||||||||||||||||||||||||||||||||||||||||||||| ||||||||||||||||||||
wild_ks3  GLEGPALTVDTACSSSLVALHLAVQSLRRGECDMALAGGVTVMATPTVFVEFSRQRGLAPDGRCKAFAEGADGTAWGEGV  274 wild_ks2  GVLLVERLSDARRLGHSVLAVVRGSAVNQDGASNGLTAPSGPAQQRVIREALADAGLGSGDVDVVEAHGTGTALGDPIEA  2902
          ||||||||||||||||||||||||||||||||||||||||||||||||||||||||||||||||||||||||||||||||
hyp_ks3   GVLLVERLSDARRLGHSVLAVVRGSAVNQDGASNGLTAPSGPAQQRVIREALADAGLGSGDVDVVEAHGTGTALGDPIEA  354
          ||||||||||||||||||||||||||||||||||||||||||||||||||||||||||||||||||||||||||||||||
wild_ks3  GVLLVERLSDARRLGHSVLAVVRGSAVNQDGASNGLTAPSGPAQQRVIREALADAGLGSGDVDVVEAHGTGTALGDPIEA  354 wild_ks2  GALLATYGRERVGDPLWLGSLKSNIGHTQAAAGVGGVIKMVEALRHGTLPRTLHVDAPSSKVEWGSGAVELLTEARAWPR  2982
          ||||||||||||||||||||||||||||||||||||||||||||||||||||||||||||||||||||||||||||||||
hyp_ks3   GALLATYGRERVGDPLWLGSLKSNIGHTQAAAGVGGVIKMVEALRHGTLPRTLHVDAPSSKVEWGSGAVELLTEARAWPR  434
          |||||||||||||||||||||||||||||||||||||||||||||||||||||||||||||||| |||||||||||||
wild_ks3  GALLATYGRERVGDPLWLGSLKSNIGHTQAAAGVGGVIKMVEALRHGTLPRTLHVDAPSSKVEWGWGAVELLTEARAWPR  434 wild_ks2  RADRKRRAAVSAFGVSGTNAHVVIEE                                                       3008
          ||||||||||||||||||||||||||
hyp_ks3   RADRKRRAAVSAFGVSGTNAHVVIEE                                                       460
          ||||||||||||||||||||||||||
wild_ks3  RADRKRRAAVSAFGVSGTNAHVVIEE                                                       460
```

MIDECAMYCIN HYPER PRODUCING STRAIN

BACKGROUND OF THE INVENTION

1. Field of the Invention

The present invention relates to a midecamycin hyper producing strain having improved productivity of midecamycin which is a member of macrolide antibiotics, and a method for producing midecamycins using this strain.

2. Background Art

Macrolide antibiotics are antibacterial agents effective upon Gram-positive bacteria, *Mycoplasma, Chlamydia* and the like and classified into clinically important antibacterial agents because they can be orally administered and have low toxicity. Among them, commercially available 16-membered ring macrolide antibiotics are broadly used in the world including Asian countries, because they have advantages in that resistances are hardly induced, interaction with other drugs is less in comparison with 14-membered ring macrolide antibiotics and influence upon the intestinal tract is also less.

Midecamycins (FIG. 1) are 16-membered ring macrolide antibiotics produced by *Streptomyces mycarofaciens* (ATCC 21454) and the like species of actinomysetes. Miocamycin as an acylation derivative thereof (Omoto, S. et al., *J. Antibiot.*, 29, 536 (1976); Yoshida, T. et al., *Jpn. J. Antibiot.*, 35, 1462 (1982)) is clinically broadly used and produced from a fermentation product of *Streptomyces mycarofaciens*. In addition, since *Streptomyces mycarofaciens* does not produce leucomycins, it also has an advantage in that removal of leucomycins by purification and the like steps can be omitted by the use of this strain.

Actinomysetes have been occupying an important position for a long time in the field of fermentation industries as producer strains of antibiotics, physiologically active substances and the like secondary metabolites, and improvement of their productivities have been carried out by various strain breeding techniques. Strain breeding by mutagenesis using various mutagens has also been carried out on the production of midecamycin by *Streptomyces mycarofaciens*. According to such a strain breeding method, it has an advantage in that a strain having a phenotype of interest can be conveniently obtained, but it cannot be elucidated about what a type of mutation was introduced into which gene. As a result of introducing random mutation, there is a possibility that a mutation that is not useful (e.g., not increasing a productivity) is jointly introduced in the breeding thereafter.

From such a point of view, it is possible to extract a useful mutation by comparing genomic sequence of a low production strain with that of a hyper producing strain, and it is possible to create a hyper producing strain in which a useful mutation alone is accumulated making use of recombinant DNA techniques.

In the microorganisms which produce macrolide antibiotics, the majority of macrolide biosynthesis genes are together concentrated within a region of from 70 to 80 kb of the genome in many cases (Donadio, S. et al., *Science*, 252, 675 (1991); MacNeil, D. J. et al., *Gene*, 115, 119 (1992); Schwecke, T. et al., *Proc. Natl. Acad. Sci.*, 92, 7839 (1995)). A high homology gene coding for a giant multifunctional protein called type I polyketide synthase (to be referred also to as PKS hereinafter) is present in the center of their cluster.

The PKS gene is generally constituted from 3 to 5 genes, and its protein forms a complex consisting of an initiator module and several extender modules. Each of them adds a specific acyl-CoA precursor to a polyketide chain in the middle of its synthesis and specifically modifies β-keto group. Accordingly, the polyketide structure is determined by the composition and order of these modules in PKS. The modules contain several domains, and each of them carries out specified function.

The initiator module consists of an acyl carrier protein (to be referred to as ACP hereinafter) domain to which acyl group of the precursor binds and an acyl transferase (to be referred to as AT hereinafter) domain which catalyzes addition of acyl group to the ACP domain. Depending on the specificity of this AT domain, the kind of acyl-CoA to be added thereto is determined. All of the extender modules contain a β-ketosynthase (β-ketoacyl acyl carrier protein synthase, to be referred also to as KS hereinafter) domain which adds the previously presenting polyketide chain to new acyl-ACP by decarboxylation condensation, and AT domain and ACP domain.

Also, each of the extender modules contain some of the domains which modify specific β-keto groups, in addition to these, and modification of the β-keto groups is determined based on the structure of the domain to be contained. These include a β-ketoreductase (to be referred also to as KR hereinafter) domain which reduces β-keto group to hydroxyl group, a dehydratase (to be referred also to as DH hereinafter) domain that removes hydroxyl group and forms double bond and an enoyl reductase (to be referred also to as ER hereinafter) domain which forms saturated carbon bond.

The last extender module is completed with a thioesterase (to be referred also to as TE hereinafter) domain which releases polyketide through its cyclization from PKS. Boundaries of modules, domains and open reading frame (to be referred also to as ORF hereinafter) of PKS can be estimated based on the sequence information on already known PKS genes.

The polyketide backbone formed by PKS undergoes methylation, acylation, oxidation, reduction, specific sugar addition and the like additional modifications, and a macrolide antibiotic is finally synthesized. Most of the genes necessary for these modifications are present in the periphery of the PKS gene.

Genes which encode deoxy sugar biosynthesis enzymes have been revealed regarding erythromycin, tylosin and the like (Summers, R. G. et al., *Microbiology*, 143, 3251 (1997); Gaisser, S. et al., *Mol. Gen. Genet.*, 256, 239 (1997); Merson-Davies, L. A. and Cundliffe, E., *Mol. Microbiol.*, 13, 349 (1994)). Synthesis of these deoxy sugars comprises activation of glucose by the addition of nucleotide diphosphate and subsequent deoxygenation, reduction, epimerization, amination, methylation and the like reactions. These sugars are introduced into macrolides by the action of specific glycosyltransferase.

Since the structures of midecamycin bear resemblance to the structures of tylosin, it is considered that it passes through almost the same biosynthetic pathway. Biosynthesis of midecamycin starts with the synthesis of malonyl-CoA, methyl malonyl-CoA, ethyl malonyl-CoA and methoxy malonyl-CoA which are precursors of the polyketide backbone. These precursors undergo cyclization through the stepwise condensation reaction by polyketide synthase, and the polyketide backbone is synthesized as a result. Thereafter, midecamycin is finally synthesized via sugar saccharide addition, hydroxylation, formylation, acylation and the like modification reactions.

In order to improve its productivity by gene recombination techniques, expression reinforcement of genes encoding the rate-determining biosynthesis reactions, expression reinforcement or gene disruption of genes which regulate expression of the biosynthesis genes, interception of unnecessary secondary metabolism systems and the like have been carried out (Kennedy, J. and Turner, G., *Mol. Gen. Genet.*, 253, 189 (1996); Review: Balts, R. H., Biotechnology of Antibiotics Second Edition, Revised and Expanded, Marcel Dekker, Inc., New York, p. 49 (1997); Review: Hutchinson, C. R. and Colombo, A. L., *Ind. Microbiol. Biotechnol.*, 23, 647 (1999); Review: Brakhage, A. A., *Microbiol. Mol. Biol. Rev.*, 62, 547 (1998)). Accordingly, when the biosynthesis gene is specified, the productivity can be improved by means of gene recombination techniques, by connecting it to an appropriate vector and introducing into a secondary metabolite producing strain.

SUMMARY OF THE INVENTION

The aforementioned methods aim at enhancing expression quantity of a rate-determining gene or deleting a rate-determining gene and thereby enhancing or deleting amount of an enzyme protein as the gene product. However, it is difficult to identify the rate-determining step by precisely grasping produced amount of the biosynthesis intermediates. For example, there are cases in which the biosynthesis scheme cannot be predicted, the predicted biosynthesis intermediate cannot be detected, standards of biosynthesis intermediate need, and the like.

The present inventors have obtained a strain having high productivity from a midecamycin-producing *Streptomyces mycarofaciens* by its breeding using a mutation treatment, and compared DNA sequences of the midecamycin biosynthesis genes derived from this hyper producing strain with the sequence of the wild strain (low production strain), and have examined to find out a mutation specific for a hyper producing strain, namely a mutation which gives high productivity.

That is, the present inventors have succeeded in isolating a DNA fragment containing midecamycin biosynthesis gene from a genomic library of a midecamycin hyper producing strain-derived genomic DNA, prepared using a *Streptomyces mycarofaciens*-derived DNA fragment as the probe which had been amplified by polymerase chain reaction (to be referred also to as PCR hereinafter) using sequences homologous to a actinomycetes-derived polyketide synthase gene as the primers. By comparing DNA sequence of the thus obtained hyper producing strain-derived midecamycin biosynthesis gene with that of the wild strain-derived midecamycin biosynthesis gene (US Patent Publication 2004-0091975A1, JP-A-2004-49100), it was found that partial substitution of β ketosynthase domain of the polyketide synthase gene occurred and productivity of midecamycin was thereby improved. Based on the above knowledge, we have continued extensive studies and, as a result, the invention was accomplished.

Accordingly, the present invention contains the following embodiments of the invention.

1. A midecamycin producing actinomycetes comprising a midecamycin biosynthesis gene or a homologue thereof, wherein at least one module in a polyketide synthase gene of a midecamycin biosynthesis gene or partial sequences of the at least one module, is substituted so as to encode the corresponding amino acid sequences of the other module.

2. The midecamycin producing actinomycetes according to the item 1, wherein a part or all of a nucleotide sequence coding for the amino acid sequence of KS3: β-ketoacyl acyl carrier protein synthase in ORF2 of the midecamycin synthase gene is substituted so as to encode the corresponding amino acid sequence of KS2: β-ketoacyl acyl carrier protein synthase in ORF 1.

3. The midecamycin producing actinomycetes according to the item 2, wherein a part or all of a nucleotide sequence coding for the amino acid sequence of from 157th to 420th positions of KS3 in ORF2 of the midecamycin synthase gene is substituted so as to encode a part or all of the corresponding amino acid sequence of from 2705th to 2968th positions of KS2 in ORF 1.

4. The midecamycin producing actinomycetes according to the item 3, wherein a part or all of a nucleotide sequence coding for the amino acid sequence of from 157th to 254th positions of KS3 in ORF2 of the midecamycin synthase gene is substituted so as to encode a part or all of the corresponding amino acid sequence of from 2705th to 2802nd positions of KS2 in ORF 1.

5. The midecamycin producing actinomycetes according to the item 4, wherein apart or all of a nucleotide sequence coding for the amino acid sequence of from 157th to 186th positions of KS3 in ORF2 of the midecamycin synthase gene is substituted so as to encode a part or all of the corresponding amino acid sequence of from 2705th to 2734th positions of KS2 in ORF 1.

6. The midecamycin producing actinomycetes according to any one of the items 1 to 5, wherein the actinomycetes is *Streptomyces mycarofaciens*.

7. The midecamycin producing actinomycetes according to the item 6, wherein the actinomycetes is *Streptomyces mycarofaciens* 1149-38 strain deposited under the number FERM BP-10501.

8. A midecamycin producing actinomycetes which is obtained by further effecting mutagenesis of the midecamycin producing actinomycetes described in any one of the items 1 to 5.

9. A method for producing midecamycin, which comprises: culturing the midecamycin producing actinomycetes described in any one of the items 1 to 5; and isolating the midecamycin produced.

10. A method for producing midecamycin substantially free from leucomycin, which comprises: culturing the midecamycin producing actinomycetes described in the item 6 or 7; and isolating the midecamycin produced.

There are provided a midecamycin hyper producing strain having improved productivity of midecamycin which is a member of macrolide antibiotics, and a method for producing midecamycins using this strain.

BRIEF DESCRIPTION OF THE DRAWINGS

FIG. 2 is a distribution diagram of *Streptomyces mycarofaciens* strains.

FIG. 3 is a similarity showing comparison of amino acid sequences of the KS2 presenting in orf 1 and KS3 in ORF2 of midecamycin polyketide synthase of a *Streptomyces mycarofaciens* strain ATCC 21454 and the KS3 (hyper KS3) presenting in ORF2 of midecamycin polyketide synthase of a *Streptomyces mycarofaciens* strain 1149-38. The amino acid number in the drawing is expressed by defining the initiation codon of each orf as 1. Sequences identified as wild_ks2, hyp_ks3, and wild_ks3 correspond to SEQ ID NO: 12, SEQ ID NO: 13, and SEQ ID NO: 14, respectively.

DETAILED DESCRIPTION OF THE INVENTION

Figure 1:
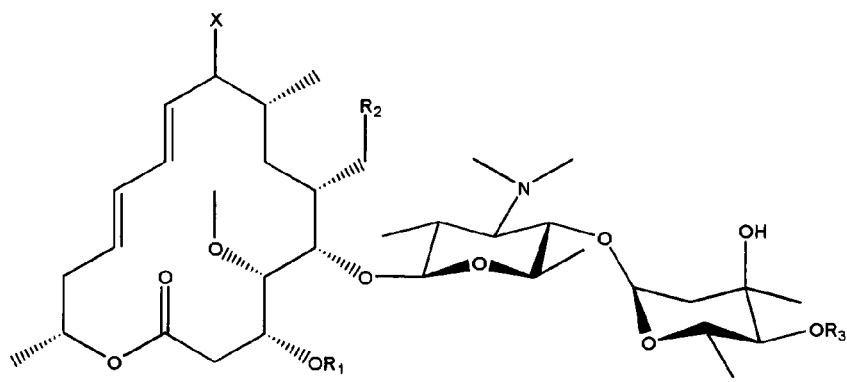
FIG. 1 is an illustration showing structure of midecamycins.

The following describes the invention in detail.
Deposition of Microorganisms

The *Streptomyces mycarofaciens* strain 1149-38 obtained in Meiji Seika Kaisha has been deposited on Feb. 16, 2005, in International Patent Organism Depositary, National Institute of Advanced Industrial Science and Technology (postal code 305-8566; Central 6, 1-1-1 Higashi, Tsukuba, Ibaraki, Japan). The deposition number is FERM P-20405 (transferred to FERM BP-10501 in Feb. 2, 2006).

The *Escherichia coli* transformed with pCOMW1 has been deposited on Jul. 16, 2002, in International Patent Organism Depositary, National Institute of Advanced Industrial Science and Technology (postal code 305-8566; Central 6, 1-1-1 Higashi, Tsukuba, Ibaraki, Japan). The deposition number is FERN P-18935 (transferred to FERM BP-8168 in Aug. 21, 2002).

The *Escherichia coli* transformed with pCOMW2 has been deposited on Jul. 16, 2002, in International Patent Organism Depositary, National Institute of Advanced Industrial Science and Technology (postal code 305-8566; Central 6, 1-1-1 Higashi, Tsukuba, Ibaraki, Japan). The deposition number is FERM P-18936 (transferred to FERM BP-8169 in Aug. 21, 2002).

The *Escherichia coli* transformed with pCOMW4 has been deposited on Jul. 16, 2002, in International Patent Organism Depositary, National Institute of Advanced Industrial Science and Technology (postal code 305-8566; Central 6, 1-1-1 Higashi, Tsukuba, Ibaraki, Japan). The deposition number is FERN P-18937 (transferred to FERM BP-8170 in Aug. 21, 2002).

Midecamycin Biosynthesis Gene According to the Invention

The wild strain (*Streptomyces mycarofaciens* ATCC 21454)-derived midecamycin biosynthesis gene is disclosed in US Patent Publication 2004-0091975A1 and JP-A-2004-49100.

According to the invention, productivity of midecamycin can be improved by exchanging each module contained in a midecamycin biosynthesis gene, polyketide synthase gene, or a partial sequence thereof, such that it encodes corresponding amino acid sequence of other module. The replacing sequence is not particularly limited, with the proviso that productivity of midecamycin is improved, but enzyme activity of polyketide synthase (productivity of midecamycin) can be improved, for example, by using the upstream β ketosynthase domain or a part thereof to substitute the corresponding part of the same downstream domain, like the case of the midecamycin hyper producing strain-derived polyketide synthase.

Length of the amino acid sequence to be replaced is not particularly limited, but is preferably from 1 to 300 residues, more preferably from 1 to 200 residues, most preferably from 1 to 100 residues.

The midecamycin productivity to be improved is 1.2 times or more, preferably 1.4 times or more based on the strain not undergoing the replacement, as the midecamycin productivity determined by the method in accordance with Examples 1 to 8 described in the following, and its improvement of 10 times or more, preferably 15 times or more, further preferably 18 times or more, in comparison with the wild strain (ATCC 21454), can be attained by combining with other mutation.

In the aforementioned substitution, it is desirable to substitute the amino acid sequence of the KS3 domain on ORF2 or a part thereof with a corresponding part of the KS2 domain on ORF 1, it is more desirable to substitute a part or all of an amino acid sequence of from the 157th to 420th positions of the KS3 domain with a corresponding part of the KS2 domain (a part or all of an amino acid sequence of from the 2705th to 2968th positions), it is further desirable to substitute a part or all of an amino acid sequence of from the 157th to 254th positions of the KS3 domain with a corresponding part of the KS2 domain (a part or all of an amino acid sequence of from the 2705th to 2802nd positions), and it is further desirable to substitute a part or all of an amino acid sequence of from the 157th to 186th positions of the KS3 domain with a corresponding part of the KS2 domain (a part or all of an amino acid sequence of from the 2705th to 2734th positions). The numbers of amino acid are a result of numbering by defining the translation initiation codon (atg/Met) as 1.

Preparation Method of Midecamycin According to the Invention

The midecamycin producing actinomycetes comprising a midecamycin biosynthesis gene or a homologue thereof, wherein one or two or more modules contained in a midecamycin biosynthesis gene, polyketide synthase gene, or partial sequences thereof, are substituted with corresponding amino acid sequences of other modules, can be obtained, for example, by the following method.

A strain having improved productivity of midecamycin is obtained by applying an ultraviolet ray irradiation or a mutagen (e.g., nitrosoguanidine) treatment to a midecamycin producer strain *Streptomyces mycarofaciens*. Midecamycin biosynthesis genes of this strain are prepared and compared with an already determined biosynthesis gene to find the mutation-introduced position. In order to confirm effectiveness of the mutation, the thus obtained mutant gene is transferred by homologous recombination into a midecamycin producer strain having no mutation (e.g., the method of Bierman et al., *Gene*, 116, 46 (1992)), and change in the productivity is verified.

Polyketide synthase is possessed of the aforementioned KS, AT and ACP domains, but their enzyme activities (reaction speeds) are considered to be irregular, so that it is considered that metabolic intermediates are accumulated thereby. Thus, it is considered that the polyketide synthesizing ability is improved by specifying a module having low reaction speed, and replacing it with a module having high reaction speed. Illustrative replacing method can be constructed making use of the methods conventionally used in the field of gene manipulation, and its examples include a method in which a restriction enzyme recognition sequence is introduced and the replacing site of interest is inserted therein, or the site of interest is amplified by PCR and ligated.

The midecamycin biosynthesis gene having improved midecamycin productivity according to the invention, in which an amino acid sequence corresponding to each module contained in a midecamycin biosynthesis gene, polyketide synthase gene, or a partial sequence thereof, is replaced by an amino acid sequence corresponding to other module, may contain one or more mutations selected from deletion, addition, insertion and substitution, other than the aforementioned substitution of amino acid sequence of each module or a part thereof (a gene having such a mutation is referred to as "analogue" hereinafter). The number of one or more mutations selected from deletion, insertion, addition and substitution is not particularly limited with the proviso that productivity of midecamycin is maintained, but is a mutation of preferably from 1 to 10, more preferably from 1 to 6, most preferably from 1 to 4, amino acid residues.

Preparation of Such a Strain to which a Mutation is Further added can be carried out for example in the following manner.

It is possible to obtain a gene in which at least one of deletion, addition, insertion and substitution of one or two or more amino acid residues is effected in the amino acid sequence of the natural enzyme of the invention, by introducing a random mutation or a site-specific mutation. By this, it is possible also to obtain a gene coding for the enzyme of the invention which is possessed of the enzyme activity of the invention but having slightly different properties such as optimum temperature, stable temperature, optimum pH, stable pH, substrate specificity and the like.

Regarding the method for introducing random mutation, for example, a method in which a transition mutation to convert cytosine into uracil is generated by the action of sodium hydrogen sulfite [Weiher, H. et al., *Proceedings of the National Academy of Sciences of the USA*, vol. 79, pp. 1408-1412 (1982)] can be used as a method for chemically treating DNA, a method in which a base substitution is generated in the process of synthesizing double strand in the presence of [α-S] dNTP [Shiraishi, H. et al., *Gene*, vol. 64, pp. 313-319 (1988)] can be used as a biochemical method, and a method in which accuracy of nucleotide incorporation is lowered by carrying out PCR by adding manganese to the reaction system [*Analytical Biochemistry*, vol. 224, pp. 347-353 (1995)) can be used as a method which uses PCR.

Regarding the method for introducing site-specific mutation, for example, a method which uses amber mutation [gapped duplex method, *Nucleic Acids Research*, vol. 12, no. 24, pp. 9441-9456 (1984)], a method which uses restriction enzyme recognition site [*Analytical Biochemistry*, vol. 200, pp. 81-88 (1992), Ito, W. et al., *Gene*, vol. 102, pp. 67-70 (1991)], a method which uses dut (dUTPase) and ung (uracil DNA glycosylase) mutation [Kunkel method, Kunkel, A. T., *Proceedings of the National Academy of Sciences of the USA*, vol. 82, pp. 488-492 (1985)], a method which uses an amber mutation using DNA polymerase and DNA ligase [oligo-nucleotide-directed dual amber (ODA) method, Hashimoto-Goto, T. et al., *Gene*, vol. 152, pp. 271-275 (1995), JP-A-7-289262], a method which uses a host in which a DNA repairing system is induced (JP-A-8-70874), a method which uses a protein that catalyses DNA chain exchange reaction (JP-A-8-140685), a PCR method which uses two primers for mutation induction use to which restriction enzyme recognition site is added (U.S. Pat. No. 5,512,463), a PCR method which uses a double-stranded DNA vector having inactivated drug resistance gene and two primers [Shen, T. et al., *Gene*, vol. 103, pp. 73-77 (1991)], a PCR method which uses an amber mutation [WO 98/02535] and the like can be used.

In addition, the site-specific mutation can be easily introduced by the use of a commercially available kit. As the commercially available kit, for example, Mutan (registered trademark)-G which uses the gapped duplex method (mfd. by Takara Bio), Mutan (registered trademark)-K which uses the Kunkel method (mfd. by Takara Bio), Mutan (registered trademark)-Express Km which uses the ODA method (mfd. by Takara Bio), QuikChange™ Site-Directed Mutagenesis Kit which uses primers for mutation induction use and *Pyrococcus furiosus*-derived DNA polymerase (mfd. by STRATAGENE) and the like can be used, and TaKaRa LA PCR in vitro Mutagenesis Kit (mfd. by Takara Bio), Mutan (registered trademark)-Super Express Km (mfd. by Takara Bio) and the like can be used as the kits which use PCR method.

The method for preparing a midecamycin biosynthesis gene having improved midecamycin productivity from a strain having improved midecamycin productivity is described using, as an example, a case in which it is prepared from *Streptomyces mycarofaciens* strain 1149-38.

The midecamycin biosynthesis gene of the invention can be isolated from the *Streptomyces mycarofaciens* strain 1149-38, for example by the following method. Since the sequence is revealed as disclosed in the invention, the concerned gene may be artificially synthesized, but it is possible to prepare it efficiently from *Streptomyces mycarofaciens* strain 1149-38.

Genomic DNA is extracted from cells of the *Streptomyces mycarofaciens* strain 1149-38 by a conventional method described in Kieser, T. et al., Practical *Streptomyces* Genetics, The John Innes Foundation, Norwick, UK (2000). A genomic library consisting of the genomic DNA of *Streptomyces mycarofaciens* is prepared by digesting this genomic DNA with an appropriate restriction enzyme and then ligating the product with an appropriate vector.

As the vector, for example, a plasmid vector, a phage vector, a cosmid vector, a BAC vector and the like various vectors and plasmids can be used.

Preparation of a DNA Fragment Containing the Midecamycin biosynthesis gene of interest from the genomic library can be attained by a hybridization using an appropriate probe. For example, appropriate primers are synthesized based on the conserved region of the amino acid sequence of a conventionally known polyketide synthase, PCR is carried out using them and using genomic DNA of *Streptomyces mycarofaciens* as the template, and the thus amplified DNA fragment can be used as the probe. In addition, since the sequence of midecamycin biosynthesis gene is revealed as disclosed in the invention, appropriate primers are synthesized based on the sequence information, PCR is carried out using genomic DNA of *Streptomyces mycarofaciens* as the template, and the thus amplified DNA fragment can also be used as the probe. Screening of the genomic library is carried out using the thus obtained DNA fragment as the probe.

Also, since the sequence of midecamycin biosynthesis gene is revealed as disclosed in the invention, primers for use in the amplification of a desired gene are synthesized based on the sequence information, PCR is carried out using genomic DNA of *Streptomyces mycarofaciens* as the template, and then the thus amplified DNA fragment can be isolated by ligating it with an appropriate vector.

Thus, regarding the polyketide synthase gene having improved midecamycin biosynthesis ability, it is possible to produce midecamycin by directly using a mutant strain before isolation, or the polyketide synthase gene having improved midecamycin biosynthesis ability may be transferred into a midecamycin producer strain, but the midecamycin of interest can also be obtained by transforming into an optional host together with total length of the midecamycin biosynthesis cluster.

The vector to be used is decided in response to the kind of host and not particularly limited, but for example, vectors of a pBR322 system and a pUC system can be cited as the *Escherichia coli* vector, and vectors of a pUB110 system, a pPL603 system and a pC194 system as the *Bacillus subtilis* vector, vectors of a pYC system and pYE system as the yeast vector, and vectors of a pIJ101 system, a pSET152 system, a pSGS system, a pSCP2* system, a SAM2 system, a pKC1139 system and a φC31 system as the actinomycetes vector (Kieser, T. et al., Practical *Streptomyces* Genetics, The John Innes Foundation, Norwick, UK (2000)).

Next, the gene is transferred into a host using the thus obtained plasmid. The host may be optionally selected from an actinomycetes, *Escherichia coli*, *Bacillus subtilis*, a yeast, a filamentous fungus and other microorganisms, in response to the kind of vector to be used.

Particularly desirable examples as the host when the vector is for actinomycetes use include *Streptomyces mycarofaciens, Streptomyces coelicolor, Streptomyces hygroscopicus, Streptomyces fradiae, Streptomyces lividans, Streptomyces kitasatoensis, Streptomyces ambofaciens* and *Streptomyces themotolerans*.

As the method for transferring a vector into a host strain, a most efficient method is selected depending on the kinds of host and vector. When an actinomycetes vector is used, transfer by conjugation with *Escherichia coli*, infection with an actinomycetes phage, introduction of host strain into protoplast and the like can be carried out (Kieser, T. et al., Practical *Streptomyces* Genetics, The John Innes Foundation, Norwick, UK (2000)). Genetic indexes possessed by the vectors to be used, such as antibiotics resistance, pock formation, melanin biosynthesis and the like, can be used in the selection of recombinants obtained by the transformation.

By culturing the thus obtained recombinants by a conventionally known method, their newly acquired properties can be examined.

Production of Midecamycin

Midecamycin can be produced by culturing the aforementioned mutant strain containing a midecamycin synthesis gene having improved midecamycin biosynthesis ability, or a recombinant into which the midecamycin synthesis gene having improved midecamycin biosynthesis ability is transferred.

Regarding the medium, conventionally used components such as glucose, sucrose, starch syrup, dextrin, starch, glycerol, molasses, animal and plant oils and the like can be used as the carbon source. Also, soybean powder, wheat germ, corn steep liquor, cotton seed meal, meat extract, polypeptone, malt extract, yeast extract, ammonium sulfate, sodium nitrate, urea and the like can be used as the nitrogen source. In addition to these components, it is also effective as occasion demands to add sodium, potassium, calcium, magnesium, cobalt, chlorine, phosphoric acid (dipotassium hydrogenphosphate or the like), sulfuric acid (magnesium sulfate or the like) and other inorganic salts which can form ions. Also, thiamine (thiamine hydrochloride or the like) and the like various vitamins, glutamic acid (sodium glutamate or the like), asparagine (DL-asparagine or the like) and the like amino acids, nucleotide and the like trace nutrients and antibiotics and the like selection drugs can also be added as occasion demands. In addition, organic matter and inorganic matter capable of assisting growth of the strain and promoting production of midecamycin can be optionally added.

The medium pH is, for example, approximately from pH 5.5 to pH 8. Regarding the culturing method, solid culture under aerobic condition, shaking culture, aeration agitation culture or submerged aeration culture can be employed, of which submerged aeration culture is particularly suitable. The temperature suitable for the culturing is from 15° C. to 40° C., but the strain grows at approximately from 22° C. to 30° C. inmost cases. Though production of midecamycin varies depending on the medium and culture conditions or the host to be used, its accumulation reaches maximum generally within 2 days to 10 days by any one of the culture methods. When the amount of midecamycin during the culturing reached maximum, the culturing is stopped and the substance of interest is isolated and purified from the cultured mixture.

In order to collect midecamycin from the cultured mixture, it can be extracted and purified by general separation means making use of its properties, such as solvent extraction, ion exchange resin method, adsorption or partition column chromatography, gel filtration, dialysis, precipitation, crystallization and the like, which may be used alone or by an optional combination. For example, it is extracted from the cultured mixture with acetone, methanol, butanol, ethyl acetate, butyl acetate or the like.

In order to further purify midecamycin, it may be effective to carryout a chromatography using silica gel, alumina or the like adsorbent, Sephadex LH-20 (mfd. by Amersham Bioscience), Toyopearl HW-40 (mfd. by Tosoh) or the like.

Pure midecamycin is obtained by such methods or an optional combination thereof.

EXAMPLES

The following illustratively describes the invention based on examples, though these do not limit the invention.

Example 1-1

Isolation of *Streptomyces mycarofaciens* (ATCC 21454)-Derived Genomic DNA and Preparation of Genomic Library Frozen seed of *Streptomyces mycarofaciens* (ATCC 21454) was inoculated into 50 ml of an S#14 medium (2% glucose, 1% polypeptone, 0.05% $K_2HPO_4$, 0.05% $MgSO_4.7H_2O$, 0.3% NaCl, pH 7.0) and cultured at 28° C. for 20 hours. The culture liquid was filtered using Bottle top filter 0.22 μm (mfd. by Corning), and then the cells on the filter were washed twice with 10 mM EDTA to recover the cells. The thus obtained cells were frozen with liquid nitrogen and then ground using a mortar and a pestle. Genomic DNA was isolated from the ground cells using ISOPLANT (mfd. by Nippon Gene) and in accordance with the protocols attached thereto.

The thus isolated genomic DNA was partially digested with Sau3AI, and then its termini were dephosphorylated. A recombinant cosmid vector was prepared by ligating this DNA fragment with SuperCos I (mfd. by Stratagene) which had been digested with BamHI and XbaI (dephosphorylation of the XbaI site alone). In vitro packaging was carried out on this recombinant cosmid vector using MaxPlax packaging extract (mfd. by Epicentre Technologies) and in accordance with the protocols attached thereto. Thereafter, an *Escherichia coli* strain XL1-BlueMR was infected with this recombinant phage and cultured on a plate to effect formation of colonies.

Example 1-2

Preparation of Probe

The following primers were prepared from the conserved region of PKS gene.
KS-F: 5'-CGGTSAAGTCSAACATCGG-3' (SEQ ID NO:1)
KS-R: 5'-GCRATCTCRCCCTGCGARTG-3' (SEQ ID NO:2)

Using KS-F and KS-R, PCR was carried out using the genomic DNA as the template. The PCR was carried out using ExTaq DNA polymerase (mfd. by Takara Bio). The thus amplified DNA fragment was inserted into pCR2.1-TOPO plasmid vector using TOPO TA cloning kit (mfd. by Invitrogen) and in accordance with the protocols attached thereto.

Sequencing of the inserted DNA fragment was carried out using a DNA sequencing kit dRhodamine Terminator Cycle Sequencing Ready Reaction (mfd. by Applied Biosystems) and ABI PRISM Genetic Analyzer (mfd. by Applied Biosystems) and in accordance with the protocols attached thereto. It was confirmed by this that the isolated DNA fragment is a part of the PKS gene.

Example 1-3

Screening of Cosmid Library

The DNA fragment was amplified by PCR, using the plasmid containing a part of midecamycin PKS gene as the template and using the primers KS-F and KS-R, and used as the probe of hybridization.

Hybond-N+ membrane (Amersham Pharmacia Biotech) was put on the plate on which colonies of the genomic library were formed, thereby effecting adhesion of the colonies thereto. By subjecting this membrane to an alkali treatment, cell lysis was effected and the recombinant cosmid DNA on the membrane was also denatured thereby into single strands and adhered to the membrane. Detection of positive clones on the membrane was carried out using ECL direct nucleic acid labeling and detection system (mfd. by Amersham Bioscience) and in accordance with the protocols attached thereto. In this manner, cosmid clones pCOMW1 (FERN P-18935) and pCOMW2 (FERN P-18936) containing a region homologous to the probe were isolated. A probe was newly prepared by PCR from a terminal sequence of the partially analyzed pCOMW1 (FERN P-18935). Screening of the genomic library was again carried out using this probe, and pCOMW4 (FERN P-18937) was isolated.

Example 1-4

Determination of Nucleotide Sequence

The clones pCOMW1 (FERM P-18935) and pCOMW2 (FERN P-18936) were partially digested with HaeIII, and then a fragment of about 2 kb was purified by an electrophoresis and ligated with pUC19 which had been digested with SmaI. This plasmid was introduced into an *Escherichia coli* strain XL1-blue, plasmids were extracted from optional colonies, and Sequencing was carried out using −21M13 forward primer and M13 reverse primer as the primers, by ABI 3700 (mfd. by Applied Biosystems) and in accordance with the protocols attached thereto. From the thus obtained results, regions of insufficient analysis were again subjected to sequencing by designing new primers based on the already analyzed nucleotide sequences. Thereafter, based on this results of analysis, a partial sequence of pCOMW4 (FERN P-18937) was determined by the primer waking.

Example 1-5

Cloning and Sequence Analysis of *Streptomyces Mycarofaciens* Strain 1251-2 Midecamycin Biosynthesis Gene Cluster The *Streptomyces mycarofaciens* strain 1251-2 is a strain in which its midecamycin productivity was improved by nitrosoguanidine treatment (FIG. 2). Since it was considered that the productivity improvement of this strain is due to mutation of midecamycin biosynthesis genes, the gene cluster was cloned and compared with the ATCC 21454-derived biosynthesis gene.

Isolation of the *Streptomyces mycarofaciens* strain 1251-2 derived genomic DNA, preparation of cosmid library and cloning were carried out in the same manner as in the cloning of ATCC 21454-derived gene.

A *Streptomyces mycarofaciens* strain 1251-2-derived cosmid library was screened to obtain pCOM1 and pCOM2. As a result of the sequence analysis of them, it was revealed that from orf 36 to 11 among, the midecamycin biosynthesis genes are contained therein.

Example 1-6

Comparison of Midecamycin Biosynthesis Gene Cluster Between Respective Strains

Regarding respective translation regions of the two types of midecamycin biosynthesis gene cluster obtained in the above manner, their DNA sequences were compared. Nucleotide sequence of orf 1 of the midecamycin polyketide synthase of *Streptomyces mycarofaciens* strain ATCC 21454 is shown in SEQ ID NO:3 and its amino acid sequence is shown in SEQ ID NO: 4, and nucleotide sequence of ORF2 in SEQ ID NO:5 and its amino acid sequence in SEQ ID NO: 6, and nucleotide sequence of ORF2 of the midecamycin polyketide synthase of *Streptomyces mycarofaciens* strain 1251-2 in SEQ ID NO:7 and its amino acid sequence is shown in SEQ ID NO:8.

As a result, it was revealed that among the *Streptomyces* mycarofaciens strain 1251-2 derived midecamycin biosynthesis gene cluster, the KS3 domain of ORF2 concerned in the aglycon biosynthesis was mutated and possessed of a sequence partially identical to the KS2 domain which is present in the ORF 1 (FIG. 3).

Example 1-7

Detection of Midecamycin Hyper Producing Strain Holding Mutant Midecamycin Biosynthesis Gene In order to judge the stage among the successive strains where the aforementioned mutation of polyketide synthase specific to *Streptomyces mycarofaciens* strain 1251-2 is introduced, detection of the mutation was carried out by the PCR method. Using combinations of W-ORF2-U with ORF2-L and H-ORF2-U with ORF2-L as the primers and using LA-PCR kit manufactured by Takara Bio, thermal denaturation was carried out at 94° C. for 3 minutes and then a step consisting of 94° C. for 1 minute and 68° C. for 2.5 minutes was repeated 25 cycles, thereby amplifying the KS3 domain of ORF2.

W-ORF2-U: 5'-GTGATGTATGACGACTACGG-3' (SEQ ID No:9)

H-ORF2-U: 5'-AAACCTCGGAAGTGTGGTCT-3' (SEQ ID No:10)

ORF2-L: 5'-ATCGAGGGCGTCGGCGGTAC-3' (SEQ ID No:11)

As a result, mutation was introduced between Strain 938-15 and Strain 1149-38.

Example 1-8

Comparison of Midecamycin Productivity of *Streptomyces Mycarofaciens* Strain 938-15 and Strain 1149-38 (FERM BP-10501)

A 0.1 ml portion of frozen seed of each of the *Streptomyces mycarofaciens* strain 938-15 and strain 1149-38 (FERM BP-10501) was inoculated into 10 ml of a seed medium (2% soluble starch, 1% glucose, 0.5% polypeptone, 0.3% yeast extract, 0.6% wheat germ, 0.2% defatted soybean cake, 0.2% $CaCO_3$, 0.02% anti foaming agent (Silicon KM-72, mfd. by Shin-Etsu Chemical), pH 7.0 before sterilization, 2 beads of 6 mm in diameter) contained in a test tube of 2 cm in inner diameter and cultured at 28° C. for 22 hours on a shaker, and this was used as the seed culture. Subsequently, 1.0 ml of the seed culture was inoculated into 30 ml of a production medium (1% glucose, 1% peptone, 0.5% meat extract, 0.4% vegetable peptone, 3% soybean crude oil, 0.2% NaCl, 0.3% $CaCO_3$, 0.08% emulsifier (Nikkol CO-20TX, mfd. by Nikko Chemical), pH 7.0) contained in a 250 ml capacity conical flask and cultured at 28° C. for 67 to 77 hours on a shaker. The culture liquid was adjusted to pH 4.0 or less with 50% sulfuric acid and then filtered, and this was used as a sample for analysis. Regarding the analyzing method, detection was carried out under conditions of: column; YMC-Pack ODS-AM (S-5 μm, 6.0×150 mm, YMC), mobile phase; buffer (0.01 M CH$_3$COONH$_4$, 0.0001 M K$_2$HPO$_4$, pH 6.05):CH$_3$CN: C$_2$H$_5$OH=3:3:2, column temperature; 35° C., flow rate; 1.20 ml/min, and detection wavelengths; 232 nm and 280 nm.

As a result, the total midecamycin quantity was 798 μg/ml in the case of strain 938-15 and 1127 μg/ml in the case of strain 1149-38 (FERM BP-10501).

This application is based on Japanese patent application JP 2005-101836, filed on Mar. 31, 2005, the entire content of which is hereby incorporated by reference, the same as if set forth at length.

What is claimed is:

1. A midecamycin-producing mutant of a *Streptomyces mycarofacines* strain ATCC 21454, wherein said mutant comprises a polyketide synthetase gene cluster that encodes a polyketide synthetase that produces a polyketide involved in midecamycin biosynthesis, wherein said polyketide synthetase gene cluster comprises an open-reading frame (ORF) encoding an initiation module, and several ORFs each encoding a separate extender module, wherein one of said several ORFs is ORF1, which encodes a β-ketoacyl-acyl carrier protein synthase domain KS2, and wherein another of said several ORFs is ORF2, which encodes a β-ketoacyl-acyl carrier protein synthase domain KS3, wherein the nucleotide sequence encoding the β-ketoacyl-acyl carrier protein synthase domain KS2 in ORF1 encodes the amino acid sequence of SEQ ID NO:12, and wherein the nucleotide sequence encoding the β-ketoacyl-acyl carrier protein synthase domain KS3 in ORF2 is substituted so as to encode the amino acid sequence of SEQ ID NO:12, whereby midecamycin production is improved.

2. A method for producing midecamycin, comprising culturing the midecamycin-producing mutant *Streptomyces mycarofacines* of claim 1 under conditions wherein the initiation module and the extender modules are expressed so as to produce a functional polyketide synthetase protein so as to produce a polyketide, whereby midecamycin is produced.

* * * * *

SEQUENCE LISTING

```
<160> NUMBER OF SEQ ID NOS: 14

<210> SEQ ID NO 1
<211> LENGTH: 19
<212> TYPE: DNA
<213> ORGANISM: Artificial
<220> FEATURE:
<223> OTHER INFORMATION: Synthetic primer

<400> SEQUENCE: 1
cggtsaagtc saacatcgg                                                  19

<210> SEQ ID NO 2
<211> LENGTH: 20
<212> TYPE: DNA
<213> ORGANISM: Artificial
<220> FEATURE:
<223> OTHER INFORMATION: Synthetic primer

<400> SEQUENCE: 2
gcratctcrc cctgcgartg                                                 20

<210> SEQ ID NO 3
<211> LENGTH: 13536
<212> TYPE: DNA
<213> ORGANISM: Streptomyces mycarofaciens
<220> FEATURE:
<221> NAME/KEY: CDS
<222> LOCATION: (1)..(13533)

<400> SEQUENCE: 3 atg ctg gtg tct gga gat ctc gtg act tcc cga att gac gac cga tcc      48
Met Leu Val Ser Gly Asp Leu Val Thr Ser Arg Ile Asp Asp Arg Ser
1               5                  10                  15 gat gca att gcc gtt gtc gga atg tcc tgt cga ttt ccc ggc gcc ccg      96
Asp Ala Ile Ala Val Val Gly Met Ser Cys Arg Phe Pro Gly Ala Pro
            20                  25                  30 gga gtc gaa gaa ttc tgg aaa ctg ctg acc gac gga acg gaa gcc gtc     144
Gly Val Glu Glu Phe Trp Lys Leu Leu Thr Asp Gly Thr Glu Ala Val
        35                  40                  45 agt cgc gcg gcc gat ggc cgt cgg cgc ggc atg atc gag gcg gtc ggc     192
Ser Arg Ala Ala Asp Gly Arg Arg Arg Gly Met Ile Glu Ala Val Gly
    50                  55                  60 gac ttc gac gcc acg ttc ttc ggc atg tca ccg cgc gag gcc gcc gag     240
Asp Phe Asp Ala Thr Phe Phe Gly Met Ser Pro Arg Glu Ala Ala Glu
65                  70                  75                  80 acc gat ccg cag cag cgc ctg ctg ctc gaa ctc ggc tgg gag gcc ctg     288
Thr Asp Pro Gln Gln Arg Leu Leu Leu Glu Leu Gly Trp Glu Ala Leu
                85                  90                  95 gag gac gcc gga atc gtc ccg ggg tcg ctg cgc ggc gag gcg gtc ggc     336
Glu Asp Ala Gly Ile Val Pro Gly Ser Leu Arg Gly Glu Ala Val Gly
            100                 105                 110 atc ttc gtc ggt gcc atg cac aac gac tac gcc acc ctg ctg cac cgg    384
Ile Phe Val Gly Ala Met His Asn Asp Tyr Ala Thr Leu Leu His Arg
        115                 120                 125
```

```
gcc ggc gca ccg gcc ggc gcc cac acc gcc acc ggc ctc cag ccc gcc      432
Ala Gly Ala Pro Ala Gly Ala His Thr Ala Thr Gly Leu Gln Pro Ala
        130             135                 140 atg ctc gcc aac cgg ctc tcc tac gtc ctg gga acg cgc ggc ccc agc      480
Met Leu Ala Asn Arg Leu Ser Tyr Val Leu Gly Thr Arg Gly Pro Ser
145                 150                 155                 160 ctg gcg gtt gac acc gcg cag tcg tcg tcg ctg gtc gcc gtg gcc ctc      528
Leu Ala Val Asp Thr Ala Gln Ser Ser Ser Leu Val Ala Val Ala Leu
                165                 170                 175 gcg gtc gag agc ctg cgc gcc gga acc tcc cgc atc gcc atc gca ggc      576
Ala Val Glu Ser Leu Arg Ala Gly Thr Ser Arg Ile Ala Ile Ala Gly
            180                 185                 190 ggc gtc aac ctg atc ctc gcc gac gag ggc tcg gcc acc atg gag cgg      624
Gly Val Asn Leu Ile Leu Ala Asp Glu Gly Ser Ala Thr Met Glu Arg
        195                 200                 205 ctc ggc gcg ctc tcc ccc gac ggg cgt tgc tac acc ttc gac gcc cgc      672
Leu Gly Ala Leu Ser Pro Asp Gly Arg Cys Tyr Thr Phe Asp Ala Arg
    210                 215                 220 gcc aac ggc tat gtg cgt ggc gag ggc ggt gcc gcc gtc gta ctg aag      720
Ala Asn Gly Tyr Val Arg Gly Glu Gly Gly Ala Ala Val Val Leu Lys
225                 230                 235                 240 ccc ctc gcc gac gcc ttg gcc gac ggc gac ccg gtg tac tgc gtg gtg      768
Pro Leu Ala Asp Ala Leu Ala Asp Gly Asp Pro Val Tyr Cys Val Val
                245                 250                 255 cgc agc gcc gcc act ggc aac gac ggc ggc ggc ccc ggg ctg acc tcc      816
Arg Ser Ala Ala Thr Gly Asn Asp Gly Gly Gly Pro Gly Leu Thr Ser
            260                 265                 270 ccc gac cac gaa ggc cag gaa gcc gtg ctc cgg gcg gcc tgc gcc cag      864
Pro Asp His Glu Gly Gln Glu Ala Val Leu Arg Ala Ala Cys Ala Gln
        275                 280                 285 gcc gga gtc gac ccc gca aag gtg cgc ttc gtc gaa ctg cac ggc acc      912
Ala Gly Val Asp Pro Ala Lys Val Arg Phe Val Glu Leu His Gly Thr
    290                 295                 300 ggc acc ccc gtg ggc gac ccg gtc gag gca cgg gcc ctg ggt gcg gtc      960
Gly Thr Pro Val Gly Asp Pro Val Glu Ala Arg Ala Leu Gly Ala Val
305                 310                 315                 320 cac ggc tcc ggg cgg ccg gcg gac gca ccc ctg ctg gtg ggc tcc gtg     1008
His Gly Ser Gly Arg Pro Ala Asp Ala Pro Leu Leu Val Gly Ser Val
                325                 330                 335 aag acc aac atc ggc cac ctg gaa ggc gca gcc ggc atc gcg ggg ctg     1056
Lys Thr Asn Ile Gly His Leu Glu Gly Ala Ala Gly Ile Ala Gly Leu
            340                 345                 350 gtc aag gcc gca ctc tgc ctg cgg aat cgc acc ctg ccc ggc tcg ctc     1104
Val Lys Ala Ala Leu Cys Leu Arg Asn Arg Thr Leu Pro Gly Ser Leu
        355                 360                 365 aac ttc gtc acc ccc cac ccc gcc atc cct ctg gac cgg ctc cgg ctg     1152
Asn Phe Val Thr Pro His Pro Ala Ile Pro Leu Asp Arg Leu Arg Leu
    370                 375                 380 aag gtg cag acg acc ccg acc acg ctg cac ccc gat ccg gac ggc tcc     1200
Lys Val Gln Thr Thr Pro Thr Thr Leu His Pro Asp Pro Asp Gly Ser
385                 390                 395                 400 ccc ctg ctg gcg ggt gtc agc tcc ttc ggt atc ggc ggc acc aac tgc     1248
Pro Leu Leu Ala Gly Val Ser Ser Phe Gly Ile Gly Gly Thr Asn Cys
                405                 410                 415 cat gtc gtc ctg gag cac ctg ccc gag ccg gcc ccc acc aca agg gaa     1296
His Val Val Leu Glu His Leu Pro Glu Pro Ala Pro Thr Thr Arg Glu
            420                 425                 430 gcc cta ccc gcc ccg cac ctg gtc ccg ccc ctg ctg ttg tcg gcc cgt     1344
Ala Leu Pro Ala Pro His Leu Val Pro Pro Leu Leu Leu Ser Ala Arg
        435                 440                 445
```

|     |     |
| --- | --- |
| tcc cac ccg gca ctg ctg gcc cag gcg gcg cgg ctc cgt gac cac ctg<br>Ser His Pro Ala Leu Leu Ala Gln Ala Ala Arg Leu Arg Asp His Leu<br>450                          455                      460 | 1392 |
| agc cgc acc gct gcc gac ccg cag gac gtc gct tac tcc ctg gcc acc<br>Ser Arg Thr Ala Ala Asp Pro Gln Asp Val Ala Tyr Ser Leu Ala Thr<br>465                        470                      475                  480 | 1440 |
| aca cgc tcc ctc ttc gag cac cgc gcc gcg ctg ccc tgc ggc aac cgc<br>Thr Arg Ser Leu Phe Glu His Arg Ala Ala Leu Pro Cys Gly Asn Arg<br>                    485                          490                      495 | 1488 |
| gag gag ttg gtc gcc gcc ctc gac gca ctc gcc cac ggc agg atc acg<br>Glu Glu Leu Val Ala Ala Leu Asp Ala Leu Ala His Gly Arg Ile Thr<br>            500                        505                      510 | 1536 |
| gcg ggc gtg cga gtc gac tcg gct gtg tcg ggt ggg acg gct gtg ttg<br>Ala Gly Val Arg Val Asp Ser Ala Val Ser Gly Gly Thr Ala Val Leu<br>515                          520                      525 | 1584 |
| ttt acg ggt cag ggt gcg cag tgg gtt ggt atg ggg cgt gag ttg tat<br>Phe Thr Gly Gln Gly Ala Gln Trp Val Gly Met Gly Arg Glu Leu Tyr<br>530                          535                      540 | 1632 |
| ggg ttg gat ggg gtg ttt gct gcg gcg ttg gat gag gtt ttg ggt gtg<br>Gly Leu Asp Gly Val Phe Ala Ala Ala Leu Asp Glu Val Leu Gly Val<br>545                        550                      555                  560 | 1680 |
| gtg ggg gag gtg ggt ggt tgg tct ttg cgt gag gtg atg ttt ggt gag<br>Val Gly Glu Val Gly Gly Trp Ser Leu Arg Glu Val Met Phe Gly Glu<br>                    565                          570                      575 | 1728 |
| ggt ggt ggt gtt ggg gtg ggg ttg ttg gat ggt acg gag ttt gcg cag<br>Gly Gly Gly Val Gly Val Gly Leu Leu Asp Gly Thr Glu Phe Ala Gln<br>            580                        585                      590 | 1776 |
| cct gct ttg ttt gcg ttg gag gtg gcg ttg ttt cgg gct gtg gag gct<br>Pro Ala Leu Phe Ala Leu Glu Val Ala Leu Phe Arg Ala Val Glu Ala<br>595                          600                      605 | 1824 |
| cgg ggg gtg cgg gct tcg gtg gtg ttg ggg cat tcg gtg ggg gag gtt<br>Arg Gly Val Arg Ala Ser Val Val Leu Gly His Ser Val Gly Glu Val<br>            610                        615                      620 | 1872 |
| gct gct gcg tgt gtg gcg ggg gtg ttt tcg ctt gcg gat gcg gcg cgg<br>Ala Ala Ala Cys Val Ala Gly Val Phe Ser Leu Ala Asp Ala Ala Arg<br>625                          630                      635                  640 | 1920 |
| ttg gtg gtg gcg cgt ggt cgg ttg atg ggt gcg ttg cct gtg ggt ggg<br>Leu Val Val Ala Arg Gly Arg Leu Met Gly Ala Leu Pro Val Gly Gly<br>                    645                          650                      655 | 1968 |
| ggg atg ttg tcg gtt cgt gcg tct gag gcc gaa ctt gtt gat gtt gtg<br>Gly Met Leu Ser Val Arg Ala Ser Glu Ala Glu Leu Val Asp Val Val<br>                    660                          665                      670 | 2016 |
| gct ggg ttg ggt ggt cgg gtg tcg gtg gct gcg gtc aat ggt ccg gcg<br>Ala Gly Leu Gly Gly Arg Val Ser Val Ala Ala Val Asn Gly Pro Ala<br>            675                        680                      685 | 2064 |
| tcg gtg gtg ttg tct ggt gag tgt ggt gcg ttg gat gtt gtt gcg gcg<br>Ser Val Val Leu Ser Gly Glu Cys Gly Ala Leu Asp Val Val Ala Ala<br>            690                        695                      700 | 2112 |
| cgg ttg ggt ggg cgt ggg gtg gag tgc aag cgg ttg gtg gtg tcg cat<br>Arg Leu Gly Gly Arg Gly Val Glu Cys Lys Arg Leu Val Val Ser His<br>705                          710                      715                  720 | 2160 |
| gcg ttt cat tcg gcg ttg atg gat ccg atg ttg gag gag ttt cgt ggg<br>Ala Phe His Ser Ala Leu Met Asp Pro Met Leu Glu Glu Phe Arg Gly<br>                    725                          730                      735 | 2208 |
| gtt gct gag agt gtg gag tat cgg cgg ccg tgt gtg ccg gtg gtg tcg<br>Val Ala Glu Ser Val Glu Tyr Arg Arg Pro Cys Val Pro Val Val Ser<br>            740                        745                      750 | 2256 |
| aat gtg acg ggt ggg gtg gtt ggg ttt gat gag ttg ggt tgt gcc gag<br>Asn Val Thr Gly Gly Val Val Gly Phe Asp Glu Leu Gly Cys Ala Glu<br>            755                        760                      765 | 2304 |

```
tat tgg gtg cgg cat gcg cgg gag gcg gtg cgt ttc gct gag ggg att      2352
Tyr Trp Val Arg His Ala Arg Glu Ala Val Arg Phe Ala Glu Gly Ile
    770             775                 780 cgg gct gct cgt gct ctt ggt gtg gat acg ttc ctg gag gtg ggt ccg      2400
Arg Ala Ala Arg Ala Leu Gly Val Asp Thr Phe Leu Glu Val Gly Pro
785             790                 795                 800 cat gcg gtt ttg acg gcg atg gct ggt cag tgt ctt gat gct gag gag      2448
His Ala Val Leu Thr Ala Met Ala Gly Gln Cys Leu Asp Ala Glu Glu
            805                 810                 815 gct gac ttg gcg ttt gtg ccg gtc ctg cgg cgt gat cgg ccg gca ttg      2496
Ala Asp Leu Ala Phe Val Pro Val Leu Arg Arg Asp Arg Pro Ala Leu
        820                 825                 830 cag acc ttc acc acc gca ctc gcc act ctg cac acc cgt gat gcc gaa      2544
Gln Thr Phe Thr Thr Ala Leu Ala Thr Leu His Thr Arg Asp Ala Glu
                835                 840                 845 ctc gac gcc gtg gcg ctc cat tca ggc agc gat gcc cgg cgg atc gac      2592
Leu Asp Ala Val Ala Leu His Ser Gly Ser Asp Ala Arg Arg Ile Asp
850                 855                 860 ctg ccc acc tac ccc ttc caa cgc cgt act cac tgg tcg ccg gcg ctg      2640
Leu Pro Thr Tyr Pro Phe Gln Arg Arg Thr His Trp Ser Pro Ala Leu
865             870                 875                 880 agc cac gga cac gcg gcc ggc gtc gtg cgg gcc tcg acc gct acc gag      2688
Ser His Gly His Ala Ala Gly Val Val Arg Ala Ser Thr Ala Thr Glu
                885                 890                 895 atc cgg ggg aac gac gag atc ccg gag agt gcc gag gca ctc ctt cgg      2736
Ile Arg Gly Asn Asp Glu Ile Pro Glu Ser Ala Glu Ala Leu Leu Arg
            900                 905                 910 gac ccg gcc gac ggg tcg ctc gcg gca tcc ccg gag ccg gcg aca ccc      2784
Asp Pro Ala Asp Gly Ser Leu Ala Ala Ser Pro Glu Pro Ala Thr Pro
        915                 920                 925 gac cag ctc gtc cgg ctg gtc cgc gag acc act gct gcc gtc ctg ggc      2832
Asp Gln Leu Val Arg Leu Val Arg Glu Thr Thr Ala Ala Val Leu Gly
    930                 935                 940 cac gac gac ccc gac gag atc gtc ctc gac cgc acc ttc acc tct cag      2880
His Asp Asp Pro Asp Glu Ile Val Leu Asp Arg Thr Phe Thr Ser Gln
945                 950                 955                 960 ggc ctg gaa tcg gtg acc gcg gtc gaa ctc cgc gac cta ctg aac cgg      2928
Gly Leu Glu Ser Val Thr Ala Val Glu Leu Arg Asp Leu Leu Asn Arg
                965                 970                 975 gcc acg ggg ctg acc ctc gcg gcc acg ctc gtc tac gac ctg ccc acc      2976
Ala Thr Gly Leu Thr Leu Ala Ala Thr Leu Val Tyr Asp Leu Pro Thr
            980                 985                 990 ccg cgc gcc gtc gcc gat tac ctg tcg gcc gcg atg ctc gcg acc gac      3024
Pro Arg Ala Val Ala Asp Tyr Leu Ser Ala Ala Met Leu Ala Thr Asp
        995                 1000                1005 gat gcg aac tcc agc gcg cac caa acc acc gcg gcg gcg acc acc      3069
Asp Ala Asn Ser Ser Ala His Gln Thr Thr Ala Ala Ala Thr Thr
    1010                1015                1020 cgg agc ggt gcg cgg aac gac gac ccg atc gcc atc gtc ggc gtc      3114
Arg Ser Gly Ala Arg Asn Asp Asp Pro Ile Ala Ile Val Gly Val
1025                1030                1035 ggc tcc cac ttc ccc ggc ggc gtg gac tcg cgc gcc ggc ctg tgg      3159
Gly Ser His Phe Pro Gly Gly Val Asp Ser Arg Ala Gly Leu Trp
    1040                1045                1050 gat ctg ctg gcc tcc ggc acc gac gcg atc tcg tcc ttt ccc acc      3204
Asp Leu Leu Ala Ser Gly Thr Asp Ala Ile Ser Ser Phe Pro Thr
1055                1060                1065 gac cgt ggt tgg gat ctc aac gag ctg tac gac ccc gag ccc ggc      3249
Asp Arg Gly Trp Asp Leu Asn Glu Leu Tyr Asp Pro Glu Pro Gly
    1070                1075                1080
```

```
atc ccc ggc aag acc tat gtg cgt cag ggc ggc ttc ctg cat cag    3294
Ile Pro Gly Lys Thr Tyr Val Arg Gln Gly Gly Phe Leu His Gln
1085            1090                1095 gcg gcc gag ttc gac gcg gag ttc ttc ggc atc tcg ccg cgc gag    3339
Ala Ala Glu Phe Asp Ala Glu Phe Phe Gly Ile Ser Pro Arg Glu
    1100                1105                1110 gcg acc gcc atg gac ccc cag cag cgg ctg ctg ctg gag acc tcc    3384
Ala Thr Ala Met Asp Pro Gln Gln Arg Leu Leu Leu Glu Thr Ser
1115                1120                1125 tgg gag gcg ctg gag gac gcc gga gtg tgc ccc gag tcg ctg cgc    3429
Trp Glu Ala Leu Glu Asp Ala Gly Val Cys Pro Glu Ser Leu Arg
    1130                1135                1140 ggc acc aac acc ggc gtg ttc atc ggc gca gtc gca ccg gag tac    3474
Gly Thr Asn Thr Gly Val Phe Ile Gly Ala Val Ala Pro Glu Tyr
1145                1150                1155 ggc ccg agg ctc cac gag gga gcg gac ggg tac gag ggg tat ctg    3519
Gly Pro Arg Leu His Glu Gly Ala Asp Gly Tyr Glu Gly Tyr Leu
    1160                1165                1170 ctc acc ggc acc acg gcg agc gtg gcc tcc ggc cgg atc gcc tac    3564
Leu Thr Gly Thr Thr Ala Ser Val Ala Ser Gly Arg Ile Ala Tyr
1175                1180                1185 acc ttc ggc acg cgc ggg ccg gcg ctc acg gtg gat acc gcg tgt    3609
Thr Phe Gly Thr Arg Gly Pro Ala Leu Thr Val Asp Thr Ala Cys
    1190                1195                1200 tcg tcg tcg ttg gtg gcg ttg cac ctg gcg gtg cag tcg ttg cgg    3654
Ser Ser Ser Leu Val Ala Leu His Leu Ala Val Gln Ser Leu Arg
1205                1210                1215 cgg ggt gag tgt gat atg gcg ttg gcc ggc gga gcc acg gtg atg    3699
Arg Gly Glu Cys Asp Met Ala Leu Ala Gly Gly Ala Thr Val Met
    1220                1225                1230 tcc ggc ccc ggc atg ttc gtg gag ttc tcc cgg cag cgt ggg ttg    3744
Ser Gly Pro Gly Met Phe Val Glu Phe Ser Arg Gln Arg Gly Leu
1235                1240                1245 gcg tcg gat ggg cgg tgc aag gcg ttc tcc gcc gat gcc gac ggc    3789
Ala Ser Asp Gly Arg Cys Lys Ala Phe Ser Ala Asp Ala Asp Gly
    1250                1255                1260 acg gcc tgg tcc gag ggc gtc gcc gtt ctg gcg ctg gag cgt ctc    3834
Thr Ala Trp Ser Glu Gly Val Ala Val Leu Ala Leu Glu Arg Leu
1265                1270                1275 tcc gac gcc cgc cgc gcc ggt cac cgg gtg ctg gcg ctg gtc cgg    3879
Ser Asp Ala Arg Arg Ala Gly His Arg Val Leu Ala Leu Val Arg
    1280                1285                1290 ggc agc gcg gtc aac cag gac ggc gcc agc aac ggt ctc acc gcg    3924
Gly Ser Ala Val Asn Gln Asp Gly Ala Ser Asn Gly Leu Thr Ala
1295                1300                1305 ccc agc ggt ccc gcc cag gag agt gtc atc cgt gag gcg ttg gcg    3969
Pro Ser Gly Pro Ala Gln Glu Ser Val Ile Arg Glu Ala Leu Ala
    1310                1315                1320 gat gcc ggg ttg ggg ccg ggt gat gtg gat gtg gtg gag gcg cat    4014
Asp Ala Gly Leu Gly Pro Gly Asp Val Asp Val Val Glu Ala His
1325                1330                1335 ggt acg ggt acg gcg ttg ggt gat ccg atc gag gct ggt gcg ttg    4059
Gly Thr Gly Thr Ala Leu Gly Asp Pro Ile Glu Ala Gly Ala Leu
    1340                1345                1350 ctg gcc acg tat gga tgt gag cgg gtg ggt gat ccg ttg tgg ttg    4104
Leu Ala Thr Tyr Gly Cys Glu Arg Val Gly Asp Pro Leu Trp Leu
1355                1360                1365 ggg tcg ctg aag tcc aac atc ggg cac act cag gcc gcg gcg ggt    4149
Gly Ser Leu Lys Ser Asn Ile Gly His Thr Gln Ala Ala Ala Gly
    1370                1375                1380
```

-continued

| | | |
|---|---|---|
| gtc gcc ggt gtc atc aag atg gtg gag gcc ctg cgc cat ggc acg<br>Val Ala Gly Val Ile Lys Met Val Glu Ala Leu Arg His Gly Thr<br>1385                    1390                    1395 | | 4194 |
| ctg ccg cgg acg ctc cac gcc gac cgc ccc agc aca cac gtc gac<br>Leu Pro Arg Thr Leu His Ala Asp Arg Pro Ser Thr His Val Asp<br>1400                    1405                    1410 | | 4239 |
| tgg tct tcg ggg ggc gtg gag ttg ctg acc gag gcg cgc ccg tgg<br>Trp Ser Ser Gly Gly Val Glu Leu Leu Thr Glu Ala Arg Pro Trp<br>1415                    1420                    1425 | | 4284 |
| ccg gag cgg gag ggc cgg ccg cgg cgg gcc gcg gtg tcg gcc ttc<br>Pro Glu Arg Glu Gly Arg Pro Arg Arg Ala Ala Val Ser Ala Phe<br>1430                    1435                    1440 | | 4329 |
| ggt gtc agc ggt acc aac gct cac ctg gtc att gaa gag ccc ccc<br>Gly Val Ser Gly Thr Asn Ala His Leu Val Ile Glu Glu Pro Pro<br>1445                    1450                    1455 | | 4374 |
| gtg gag ttg cct gct ggt gct ggt gct ggt gct ggt gct ggt gct<br>Val Glu Leu Pro Ala Gly Ala Gly Ala Gly Ala Gly Ala Gly Ala<br>1460                    1465                    1470 | | 4419 |
| ggg gtg tct tcg gtt gtg gcg tgg ccg ttg tcg gct cgt tcg ggt<br>Gly Val Ser Ser Val Val Ala Trp Pro Leu Ser Ala Arg Ser Gly<br>1475                    1480                    1485 | | 4464 |
| gag gcg ttg cgg gcg cag gcg gtg cgg ttg cgt gag cat gtg gag<br>Glu Ala Leu Arg Ala Gln Ala Val Arg Leu Arg Glu His Val Glu<br>1490                    1495                    1500 | | 4509 |
| cgt gtt ggg gct gat ccg gtt gat gtt gcc ttt tcg ttg gcg gtg<br>Arg Val Gly Ala Asp Pro Val Asp Val Ala Phe Ser Leu Ala Val<br>1505                    1510                    1515 | | 4554 |
| acg cgt gcg tcg ttc ggt gag cgt gcg gtg gtc gtt ggt ggt gac<br>Thr Arg Ala Ser Phe Gly Glu Arg Ala Val Val Val Gly Gly Asp<br>1520                    1525                    1530 | | 4599 |
| cgt gcg gag ttg ctg gcg ggg ctt gat gcg ctt gct ggg ggg cgt<br>Arg Ala Glu Leu Leu Ala Gly Leu Asp Ala Leu Ala Gly Gly Arg<br>1535                    1540                    1545 | | 4644 |
| cgg ggg ccg ggg gtt gtc cgg ggc tcg gct gtg tcg ggt ggg acg<br>Arg Gly Pro Gly Val Val Arg Gly Ser Ala Val Ser Gly Gly Thr<br>1550                    1555                    1560 | | 4689 |
| gct gtg ttg ttt acg ggt cag ggt gcg cag tgg gtt ggt atg ggg<br>Ala Val Leu Phe Thr Gly Gln Gly Ala Gln Trp Val Gly Met Gly<br>1565                    1570                    1575 | | 4734 |
| cgt gag ttg tat ggg ttg gat ggg gtg ttt gct gcg gcg ttg gat<br>Arg Glu Leu Tyr Gly Leu Asp Gly Val Phe Ala Ala Ala Leu Asp<br>1580                    1585                    1590 | | 4779 |
| gag gtg ttg ggt gtg gtg ggg gag gtg ggt ggt tgg tct ttg cgt<br>Glu Val Leu Gly Val Val Gly Glu Val Gly Gly Trp Ser Leu Arg<br>1595                    1600                    1605 | | 4824 |
| gag gtg atg ttt ggt gag ggt ggt ggt gtt ggg gtg ggg ttg ttg<br>Glu Val Met Phe Gly Glu Gly Gly Gly Val Gly Val Gly Leu Leu<br>1610                    1615                    1620 | | 4869 |
| gat ggt acg gag ttt gcg cag cct gct ttg ttt gcg ttg gag gtg<br>Asp Gly Thr Glu Phe Ala Gln Pro Ala Leu Phe Ala Leu Glu Val<br>1625                    1630                    1635 | | 4914 |
| gcg ttg ttt cgg gct gtg gag gct cgg ggg gtg cgg gct tcg gtg<br>Ala Leu Phe Arg Ala Val Glu Ala Arg Gly Val Arg Ala Ser Val<br>1640                    1645                    1650 | | 4959 |
| gtg ttg ggg cat tcg gtg ggg gag gtt gct gct gcg tgt gtg gcg<br>Val Leu Gly His Ser Val Gly Glu Val Ala Ala Ala Cys Val Ala<br>1655                    1660                    1665 | | 5004 |
| ggg gtg ttt tcg ctt gcg gat gcg gcg cgg ttg gtg gtg gcg cgt<br>Gly Val Phe Ser Leu Ala Asp Ala Ala Arg Leu Val Val Ala Arg<br>1670                    1675                    1680 | | 5049 |

-continued

| | | |
|---|---|---|
| ggt cgg ttg atg ggt ggg ttg cct gtg ggt ggg ggg atg ttg tcg<br>Gly Arg Leu Met Gly Gly Leu Pro Val Gly Gly Gly Met Leu Ser<br>1685                    1690                    1695 | 5094 |
| gtt cgt gcg tct gag gcc gaa ctt gct gat gtt gtg gct ggg ttg<br>Val Arg Ala Ser Glu Ala Glu Leu Ala Asp Val Val Ala Gly Leu<br>1700                    1705                    1710 | 5139 |
| ggt ggt cgg gtg tcg gtg gct gcg gtc aat ggt ccg gcg tcg gtg<br>Gly Gly Arg Val Ser Val Ala Ala Val Asn Gly Pro Ala Ser Val<br>1715                    1720                    1725 | 5184 |
| gtg ttg tct ggt gag tgt ggt gcg ttg gat gtt gtt gcg gcg cgg<br>Val Leu Ser Gly Glu Cys Gly Ala Leu Asp Val Val Ala Ala Arg<br>1730                    1735                    1740 | 5229 |
| ttg ggt ggg cgt ggg gtg gag tgc aag cgg ttg gtg gtg tcg cat<br>Leu Gly Gly Arg Gly Val Glu Cys Lys Arg Leu Val Val Ser His<br>1745                    1750                    1755 | 5274 |
| gcg ttt cat tcg gcg ttg atg gag ccg atg ttg gag gag ttt cgt<br>Ala Phe His Ser Ala Leu Met Glu Pro Met Leu Glu Glu Phe Arg<br>1760                    1765                    1770 | 5319 |
| ggg gtt gct gag agt gtg gag tat cgg cgg ccg tgt gtg ccg gtg<br>Gly Val Ala Glu Ser Val Glu Tyr Arg Arg Pro Cys Val Pro Val<br>1775                    1780                    1785 | 5364 |
| gtg tcg aat gtg acg ggt ggg gtg gtt ggg ttt gat gag ttg ggt<br>Val Ser Asn Val Thr Gly Gly Val Val Gly Phe Asp Glu Leu Gly<br>1790                    1795                    1800 | 5409 |
| tgt gcc gag tat tgg gtg cgg cat gcg cgg gag gcg gtg cgt ttc<br>Cys Ala Glu Tyr Trp Val Arg His Ala Arg Glu Ala Val Arg Phe<br>1805                    1810                    1815 | 5454 |
| gct gag ggg ata cgg gct gct cgt gct ctt ggt gtg gat acg ttc<br>Ala Glu Gly Ile Arg Ala Ala Arg Ala Leu Gly Val Asp Thr Phe<br>1820                    1825                    1830 | 5499 |
| ctg gag gtt ggt ccg cat gcg gtt ttg acg gcg atg gct ggt cag<br>Leu Glu Val Gly Pro His Ala Val Leu Thr Ala Met Ala Gly Gln<br>1835                    1840                    1845 | 5544 |
| tgt ctt gat gga gag gag gct gac ttg gcg ttt gtg ccg gtc ctg<br>Cys Leu Asp Gly Glu Glu Ala Asp Leu Ala Phe Val Pro Val Leu<br>1850                    1855                    1860 | 5589 |
| cgg cgt gat cgg ccg gca tcg cag acc ttc acc acc gca ctc gcc<br>Arg Arg Asp Arg Pro Ala Ser Gln Thr Phe Thr Thr Ala Leu Ala<br>1865                    1870                    1875 | 5634 |
| acg ctt tgt gtt cgg ggc act gag gtc gat tgg gcc acg ccg cac<br>Thr Leu Cys Val Arg Gly Thr Glu Val Asp Trp Ala Thr Pro His<br>1880                    1885                    1890 | 5679 |
| cgg aag agt ggt gca caa cgc att gac ctg ccc acg tac ccc ttc<br>Arg Lys Ser Gly Ala Gln Arg Ile Asp Leu Pro Thr Tyr Pro Phe<br>1895                    1900                    1905 | 5724 |
| cag cgc gcc cga tac tgg ctt gac ccc gcc cct gca atg gcg ctc<br>Gln Arg Ala Arg Tyr Trp Leu Asp Pro Ala Pro Ala Met Ala Leu<br>1910                    1915                    1920 | 5769 |
| act acc gtg gcc gcc agt tcg gcc gag gcc gcg acg gca act<br>Thr Thr Val Ala Ala Ser Ser Ala Glu Ala Ala Thr Ala Thr<br>1925                    1930                    1935 | 5814 |
| gag ggg aca gcc ctg gaa acg gcc ggg ctc cgc tac cgc atc gcc<br>Glu Gly Thr Ala Leu Glu Thr Ala Gly Leu Arg Tyr Arg Ile Ala<br>1940                    1945                    1950 | 5859 |
| tgg cag gcc gcc gcc acg gac cgc ggc acc tct cgc tcg gcg ggg<br>Trp Gln Ala Ala Ala Thr Asp Arg Gly Thr Ser Arg Ser Ala Gly<br>1955                    1960                    1965 | 5904 |
| cac gtg gtg cta ctc acc tcg gac gac gac gcg acc gaa tcc gga<br>His Val Val Leu Leu Thr Ser Asp Asp Asp Ala Thr Glu Ser Gly<br>1970                    1975                    1980 | 5949 |

```
ctt gcc gcc gcg att acc cgc gaa ctc gcc gtg cgc ggc gcc gag         5994
Leu Ala Ala Ala Ile Thr Arg Glu Leu Ala Val Arg Gly Ala Glu
1985                1990                1995 gta cgc acc gcg atc ctg cca gtc ggc acc gac cgc gag acg gcc         6039
Val Arg Thr Ala Ile Leu Pro Val Gly Thr Asp Arg Glu Thr Ala
    2000                2005                2010 gca gac ctg cta cga acc tcc ggt gac ggc gcc gca cgc agc acg         6084
Ala Asp Leu Leu Arg Thr Ser Gly Asp Gly Ala Ala Arg Ser Thr
2015                2020                2025 cac gtc ctg tgg ctc gcc ccg gcc gag ccc gac acg gcc gac gcc         6129
His Val Leu Trp Leu Ala Pro Ala Glu Pro Asp Thr Ala Asp Ala
        2030                2035                2040 gtc gcg ctg atc cag gcc ctg ggc gag gca ggg cac gac gcc cca         6174
Val Ala Leu Ile Gln Ala Leu Gly Glu Ala Gly His Asp Ala Pro
2045                2050                2055 ctg tgg atc gcc acg cgt gac gcg gtg gcc gtc cag ccg ggc gag         6219
Leu Trp Ile Ala Thr Arg Asp Ala Val Ala Val Gln Pro Gly Glu
        2060                2065                2070 aag ctg tcc gtc gcc gga gcg cag ctc tgg ggg ctc ggg cag gtc         6264
Lys Leu Ser Val Ala Gly Ala Gln Leu Trp Gly Leu Gly Gln Val
2075                2080                2085 gcc gcc ctc gaa ctg ttc cag cgc tgg ggc ggc ctg gtg gac ctg         6309
Ala Ala Leu Glu Leu Phe Gln Arg Trp Gly Gly Leu Val Asp Leu
        2090                2095                2100 ccc gag aac ccg tcg ccc gct gcg gtc cgc gcg ttc gtc ggg gcg         6354
Pro Glu Asn Pro Ser Pro Ala Ala Val Arg Ala Phe Val Gly Ala
2105                2110                2115 ctg ttc gcg gag ggt gac gac aac cag atc gcg gtg cgg ccc tcc         6399
Leu Phe Ala Glu Gly Asp Asp Asn Gln Ile Ala Val Arg Pro Ser
        2120                2125                2130 ggc gtg tac gtc cgc cgc gtg gcc ccc gcc ccc gcc ccc gct ccc         6444
Gly Val Tyr Val Arg Arg Val Ala Pro Ala Pro Ala Pro Ala Pro
2135                2140                2145 gcc ctc atc ggg cag gct gcg cag gac gac cgg tcc ggc ccg tcc         6489
Ala Leu Ile Gly Gln Ala Ala Gln Asp Asp Arg Ser Gly Pro Ser
        2150                2155                2160 gat gga ctc gat ggg aac aat gga acc gcg ccg gtg aac tgg cac         6534
Asp Gly Leu Asp Gly Asn Asn Gly Thr Ala Pro Val Asn Trp His
2165                2170                2175 ccc tcc ggc acc gta ctg atc acc ggt ggc acc ggg gcc ctc ggc         6579
Pro Ser Gly Thr Val Leu Ile Thr Gly Gly Thr Gly Ala Leu Gly
        2180                2185                2190 gca cag gtg gcc cgc agg ctc gcc cga gcg ggc gcg ccg cat ctg         6624
Ala Gln Val Ala Arg Arg Leu Ala Arg Ala Gly Ala Pro His Leu
2195                2200                2205 ctc ctg gtc agc cgc gtt gga ccg gac ggc cct ggt acg ggc gaa         6669
Leu Leu Val Ser Arg Arg Gly Pro Asp Gly Pro Gly Thr Gly Glu
        2210                2215                2220 ctg gtc ggg gaa ctg aca gcg cac ggc acc gaa gtg acc gtc acg         6714
Leu Val Gly Glu Leu Thr Ala His Gly Thr Glu Val Thr Val Thr
2225                2230                2235 gcc tgt gac gcc gcc gac cgc gat gcg ctc gcc gag ctg ctc gcg         6759
Ala Cys Asp Ala Ala Asp Arg Asp Ala Leu Ala Glu Leu Leu Ala
        2240                2245                2250 agc att ccc gag gat cgc ccc ctc acc gcc gta ctg cac gcg gca         6804
Ser Ile Pro Glu Asp Arg Pro Leu Thr Ala Val Leu His Ala Ala
2255                2260                2265 ggt gtg ctc gac gac ggc gtg ctc gac gcg ctc acc ccc gat cgg         6849
Gly Val Leu Asp Asp Gly Val Leu Asp Ala Leu Thr Pro Asp Arg
        2270                2275                2280
```

| | | | | | | | | | | | | |
|---|---|---|---|---|---|---|---|---|---|---|---|---|
| ctc | gac | gcc | gta | ctg | cgc | gcc | aag | gta | acc | gtg | gcc | cgc | cac | ctg | 6894 |
| Leu | Asp | Ala | Val | Leu | Arg | Ala | Lys | Val | Thr | Val | Ala | Arg | His | Leu | |
| 2285 | | | | 2290 | | | | | 2295 | | | | | | |

| | | | | | | | | | | | | |
|---|---|---|---|---|---|---|---|---|---|---|---|---|
| gac | gag | ctc | acc | gca | ggc | ata | ccg | ctg | gat | gcc | ttt | gtg | ctc | ttc | 6939 |
| Asp | Glu | Leu | Thr | Ala | Gly | Ile | Pro | Leu | Asp | Ala | Phe | Val | Leu | Phe | |
| 2300 | | | | 2305 | | | | | 2310 | | | | | | |

| | | | | | | | | | | | | |
|---|---|---|---|---|---|---|---|---|---|---|---|---|
| tcc | tcc | atc | gtc | ggg | gtg | tgg | ggc | aac | ggc | ggc | cag | ggc | ggc | tat | 6984 |
| Ser | Ser | Ile | Val | Gly | Val | Trp | Gly | Asn | Gly | Gly | Gln | Gly | Gly | Tyr | |
| 2315 | | | | 2320 | | | | | 2325 | | | | | | |

| | | | | | | | | | | | | |
|---|---|---|---|---|---|---|---|---|---|---|---|---|
| gcg | gcg | gcc | aac | gcc | gcg | ctc | gat | gcc | ctg | gcg | cac | cgg | cgc | cgg | 7029 |
| Ala | Ala | Ala | Asn | Ala | Ala | Leu | Asp | Ala | Leu | Ala | His | Arg | Arg | Arg | |
| 2330 | | | | 2335 | | | | | 2340 | | | | | | |

| | | | | | | | | | | | | |
|---|---|---|---|---|---|---|---|---|---|---|---|---|
| gcc | cgg | gga | cag | cgt | gcc | acg | tcg | att | gcc | tgg | ggg | ccg | tgg | gcc | 7074 |
| Ala | Arg | Gly | Gln | Arg | Ala | Thr | Ser | Ile | Ala | Trp | Gly | Pro | Trp | Ala | |
| 2345 | | | | 2350 | | | | | 2355 | | | | | | |

| | | | | | | | | | | | | |
|---|---|---|---|---|---|---|---|---|---|---|---|---|
| ggc | gcc | gga | atg | gcg | gcc | ggc | gca | ggc | tcg | aag | gcc | ttc | cag | cgg | 7119 |
| Gly | Ala | Gly | Met | Ala | Ala | Gly | Ala | Gly | Ser | Lys | Ala | Phe | Gln | Arg | |
| 2360 | | | | 2365 | | | | | 2370 | | | | | | |

| | | | | | | | | | | | | |
|---|---|---|---|---|---|---|---|---|---|---|---|---|
| gat | ggc | atc | cag | gct | ctg | gat | ccc | gag | cgt | gca | ctc | aat | gtg | ctg | 7164 |
| Asp | Gly | Ile | Gln | Ala | Leu | Asp | Pro | Glu | Arg | Ala | Leu | Asn | Val | Leu | |
| 2375 | | | | 2380 | | | | | 2385 | | | | | | |

| | | | | | | | | | | | | |
|---|---|---|---|---|---|---|---|---|---|---|---|---|
| gac | gac | gtg | gtt | cgc | gcc | gac | gag | acg | tct | gtg | gcc | gcc | gag | ccc | 7209 |
| Asp | Asp | Val | Val | Arg | Ala | Asp | Glu | Thr | Ser | Val | Ala | Ala | Glu | Pro | |
| 2390 | | | | 2395 | | | | | 2400 | | | | | | |

| | | | | | | | | | | | | |
|---|---|---|---|---|---|---|---|---|---|---|---|---|
| tct | ttg | atc | gtc | gcc | gat | gtg | gac | tgg | agc | acg | ttc | gtc | ggg | cgc | 7254 |
| Ser | Leu | Ile | Val | Ala | Asp | Val | Asp | Trp | Ser | Thr | Phe | Val | Gly | Arg | |
| 2405 | | | | 2410 | | | | | 2415 | | | | | | |

| | | | | | | | | | | | | |
|---|---|---|---|---|---|---|---|---|---|---|---|---|
| tcc | gtc | gcc | cga | cgc | acc | tgg | gcg | ctt | ttc | gac | ggt | gtt | ccg | gcc | 7299 |
| Ser | Val | Ala | Arg | Arg | Thr | Trp | Ala | Leu | Phe | Asp | Gly | Val | Pro | Ala | |
| 2420 | | | | 2425 | | | | | 2430 | | | | | | |

| | | | | | | | | | | | | |
|---|---|---|---|---|---|---|---|---|---|---|---|---|
| gcc | tgc | tcc | gcg | cgt | tcc | gcc | cag | gcc | gca | cag | ggc | cgt | tcc | gcg | 7344 |
| Ala | Cys | Ser | Ala | Arg | Ser | Ala | Gln | Ala | Ala | Gln | Gly | Arg | Ser | Ala | |
| 2435 | | | | 2440 | | | | | 2445 | | | | | | |

| | | | | | | | | | | | | |
|---|---|---|---|---|---|---|---|---|---|---|---|---|
| cac | gcc | ccg | gga | gag | cgg | ccg | cac | cac | ggc | ggc | att | ggt | ggg | agc | 7389 |
| His | Ala | Pro | Gly | Glu | Arg | Pro | His | His | Gly | Gly | Ile | Gly | Gly | Ser | |
| 2450 | | | | 2455 | | | | | 2460 | | | | | | |

| | | | | | | | | | | | | |
|---|---|---|---|---|---|---|---|---|---|---|---|---|
| gga | gac | gga | gcg | gac | gag | gac | cgc | ccc | tgg | ctc | tct | gcc | ggc | ccc | 7434 |
| Gly | Asp | Gly | Ala | Asp | Glu | Asp | Arg | Pro | Trp | Leu | Ser | Ala | Gly | Pro | |
| 2465 | | | | 2470 | | | | | 2475 | | | | | | |

| | | | | | | | | | | | | |
|---|---|---|---|---|---|---|---|---|---|---|---|---|
| tcc | tcg | ccg | gaa | cgg | cgg | cgg | gca | ctg | ctc | gac | ttg | gtg | cgc | tcc | 7479 |
| Ser | Ser | Pro | Glu | Arg | Arg | Arg | Ala | Leu | Leu | Asp | Leu | Val | Arg | Ser | |
| 2480 | | | | 2485 | | | | | 2490 | | | | | | |

| | | | | | | | | | | | | |
|---|---|---|---|---|---|---|---|---|---|---|---|---|
| gag | gcc | gcc | gag | atc | ctg | cgt | cac | ggt | tcg | gct | gcc | gcg | gtc | gac | 7524 |
| Glu | Ala | Ala | Glu | Ile | Leu | Arg | His | Gly | Ser | Ala | Ala | Ala | Val | Asp | |
| 2495 | | | | 2500 | | | | | 2505 | | | | | | |

| | | | | | | | | | | | | |
|---|---|---|---|---|---|---|---|---|---|---|---|---|
| ccg | gag | acc | gcg | ttc | cgg | gcc | gcc | ggg | ttc | gac | tcc | ctc | acc | gtg | 7569 |
| Pro | Glu | Thr | Ala | Phe | Arg | Ala | Ala | Gly | Phe | Asp | Ser | Leu | Thr | Val | |
| 2510 | | | | 2515 | | | | | 2520 | | | | | | |

| | | | | | | | | | | | | |
|---|---|---|---|---|---|---|---|---|---|---|---|---|
| ctc | gaa | ctg | cgt | aat | cgt | ctg | acc | gcc | gcc | atc | ggg | ctg | aac | ctg | 7614 |
| Leu | Glu | Leu | Arg | Asn | Arg | Leu | Thr | Ala | Ala | Ile | Gly | Leu | Asn | Leu | |
| 2525 | | | | 2530 | | | | | 2535 | | | | | | |

| | | | | | | | | | | | | |
|---|---|---|---|---|---|---|---|---|---|---|---|---|
| ccg | agc | acc | ctg | ctg | ttc | gac | tat | ccg | aac | ccg | aac | gcc | ctg | gcc | 7659 |
| Pro | Ser | Thr | Leu | Leu | Phe | Asp | Tyr | Pro | Asn | Pro | Asn | Ala | Leu | Ala | |
| 2540 | | | | 2545 | | | | | 2550 | | | | | | |

| | | | | | | | | | | | | |
|---|---|---|---|---|---|---|---|---|---|---|---|---|
| gac | cat | ctg | cac | gac | gaa | ttg | ttc | ggt | gct | gac | agc | gaa | gca | ccg | 7704 |
| Asp | His | Leu | His | Asp | Glu | Leu | Phe | Gly | Ala | Asp | Ser | Glu | Ala | Pro | |
| 2555 | | | | 2560 | | | | | 2565 | | | | | | |

| | | | | | | | | | | | | |
|---|---|---|---|---|---|---|---|---|---|---|---|---|
| ctc | gcc | gcg | aac | acg | ccc | acc | cgg | gcc | tcg | gcc | gac | gac | cgc | gag | 7749 |
| Leu | Ala | Ala | Asn | Thr | Pro | Thr | Arg | Ala | Ser | Ala | Asp | Asp | Arg | Glu | |
| 2570 | | | | 2575 | | | | | 2580 | | | | | | |

| | | | | | | | | | | | | |
|---|---|---|---|---|---|---|---|---|---|---|---|---|
| ccg | att | gcg | gtc | gtt | ggt | atg | gcc | tgt | cgt | tat | ccg | ggt ggg gtg | 7794 |
| Pro | Ile | Ala | Val | Val | Gly | Met | Ala | Cys | Arg | Tyr | Pro | Gly Gly Val |
| | 2585 | | | | 2590 | | | | | 2595 | | |
| gcg | gcg | ccg | gag | gaa | ctg | tgg | gac | ctg | gtg | gcc | gga | ggc ggg cat | 7839 |
| Ala | Ala | Pro | Glu | Glu | Leu | Trp | Asp | Leu | Val | Ala | Gly | Gly Gly His |
| | 2600 | | | | 2605 | | | | | 2610 | | |
| gcg | atc | tcc | ccg | ttg | cct | gcc | aac | cga | ggt | tgg | gac | ctt gag ggg | 7884 |
| Ala | Ile | Ser | Pro | Leu | Pro | Ala | Asn | Arg | Gly | Trp | Asp | Leu Glu Gly |
| | 2615 | | | | 2620 | | | | | 2625 | | |
| ctc | tac | gac | ccg | gag | ccg | ggc | gtg | ccg | ggt | aag | agc | tat gtg cgt | 7929 |
| Leu | Tyr | Asp | Pro | Glu | Pro | Gly | Val | Pro | Gly | Lys | Ser | Tyr Val Arg |
| | 2630 | | | | 2635 | | | | | 2640 | | |
| gag | ggg | ggt | ttt | ctg | cac | ggg | gcg | gcc | gag | ttc | gat | gcg gag ttc | 7974 |
| Glu | Gly | Gly | Phe | Leu | His | Gly | Ala | Ala | Glu | Phe | Asp | Ala Glu Phe |
| | 2645 | | | | 2650 | | | | | 2655 | | |
| ttc | ggt | gtt | tcg | ccg | cgt | gag | gcg | gcg | gcg | atg | gat | ccg cag cag | 8019 |
| Phe | Gly | Val | Ser | Pro | Arg | Glu | Ala | Ala | Ala | Met | Asp | Pro Gln Gln |
| | 2660 | | | | 2665 | | | | | 2670 | | |
| cgg | ttg | ttg | ttg | gag | acg | tcg | tgg | gag | gcg | ttg | gag | cgg gcc ggg | 8064 |
| Arg | Leu | Leu | Leu | Glu | Thr | Ser | Trp | Glu | Ala | Leu | Glu | Arg Ala Gly |
| | 2675 | | | | 2680 | | | | | 2685 | | |
| atc | gtg | ccg | gct | gcg | ctg | cgc | ggc | acc | cgc | acc | gga | gtc ttc acc | 8109 |
| Ile | Val | Pro | Ala | Ala | Leu | Arg | Gly | Thr | Arg | Thr | Gly | Val Phe Thr |
| | 2690 | | | | 2695 | | | | | 2700 | | |
| ggc | atc | tcc | cag | cag | gac | tac | gcc | gcc | cag | ttg | ggg | gac gcg gcc | 8154 |
| Gly | Ile | Ser | Gln | Gln | Asp | Tyr | Ala | Ala | Gln | Leu | Gly | Asp Ala Ala |
| | 2705 | | | | 2710 | | | | | 2715 | | |
| gag | acc | tac | ggc | ggc | cat | gtg | ctc | acc | gga | aac | ctc | gga agt gtg | 8199 |
| Glu | Thr | Tyr | Gly | Gly | His | Val | Leu | Thr | Gly | Asn | Leu | Gly Ser Val |
| | 2720 | | | | 2725 | | | | | 2730 | | |
| gtc | tcc | ggc | cgg | gtt | gct | tac | tcc | ttg | ggt | ttg | gag | ggg ccg gcg | 8244 |
| Val | Ser | Gly | Arg | Val | Ala | Tyr | Ser | Leu | Gly | Leu | Glu | Gly Pro Ala |
| | 2735 | | | | 2740 | | | | | 2745 | | |
| ctc | acg | gtg | gat | acc | gcg | tgt | tcg | tcg | tcg | ttg | gtg | gcg ttg cat | 8289 |
| Leu | Thr | Val | Asp | Thr | Ala | Cys | Ser | Ser | Ser | Leu | Val | Ala Leu His |
| | 2750 | | | | 2755 | | | | | 2760 | | |
| ctg | gcg | gtg | cag | tcg | ttg | cgg | cgg | ggt | gag | tgc | gat | atg gcg ttg | 8334 |
| Leu | Ala | Val | Gln | Ser | Leu | Arg | Arg | Gly | Glu | Cys | Asp | Met Ala Leu |
| | 2765 | | | | 2770 | | | | | 2775 | | |
| gcc | ggt | ggt | gtg | acg | gtg | atg | gcg | acg | ccg | acg | gtg | ttt gtg gag | 8379 |
| Ala | Gly | Gly | Val | Thr | Val | Met | Ala | Thr | Pro | Thr | Val | Phe Val Glu |
| | 2780 | | | | 2785 | | | | | 2790 | | |
| ttt | tcc | cgg | cag | cgt | ggg | ttg | gcg | tcg | gat | ggg | cgg | tgc aag gcg | 8424 |
| Phe | Ser | Arg | Gln | Arg | Gly | Leu | Ala | Ser | Asp | Gly | Arg | Cys Lys Ala |
| | 2795 | | | | 2800 | | | | | 2805 | | |
| ttt | gcg | gag | ggt | gct | gat | ggt | act | gct | tgg | ggt | gag | ggt gtt ggt | 8469 |
| Phe | Ala | Glu | Gly | Ala | Asp | Gly | Thr | Ala | Trp | Gly | Glu | Gly Val Gly |
| | 2810 | | | | 2815 | | | | | 2820 | | |
| gtg | ctg | ttg | gtg | gag | cgg | ctg | tcc | gat | gcc | cgt | cgc | ctt ggt cac | 8514 |
| Val | Leu | Leu | Val | Glu | Arg | Leu | Ser | Asp | Ala | Arg | Arg | Leu Gly His |
| | 2825 | | | | 2830 | | | | | 2835 | | |
| tcg | gtg | ttg | gcg | gtg | gtg | cgg | ggg | agt | gcg | gtt | aat | cag gac ggt | 8559 |
| Ser | Val | Leu | Ala | Val | Val | Arg | Gly | Ser | Ala | Val | Asn | Gln Asp Gly |
| | 2840 | | | | 2845 | | | | | 2850 | | |
| gcc | agt | aat | ggt | ttg | acg | gcg | ccc | agt | ggt | ccg | gct | cag cag agg | 8604 |
| Ala | Ser | Asn | Gly | Leu | Thr | Ala | Pro | Ser | Gly | Pro | Ala | Gln Gln Arg |
| | 2855 | | | | 2860 | | | | | 2865 | | |
| gtg | atc | cgt | gag | gcg | ttg | gcg | gat | gcc | ggg | ttg | ggg | tcg ggt gat | 8649 |
| Val | Ile | Arg | Glu | Ala | Leu | Ala | Asp | Ala | Gly | Leu | Gly | Ser Gly Asp |
| | 2870 | | | | 2875 | | | | | 2880 | | |

-continued

| | |
|---|---|
| gtg gat gtg gtg gag gcg cat ggt acg ggt acg gcg ttg ggt gat<br>Val Asp Val Val Glu Ala His Gly Thr Gly Thr Ala Leu Gly Asp<br>2885                          2890                          2895 | 8694 |
| ccg atc gag gct ggt gcg ttg ctg gcc acg tat ggg cgt gag cgg<br>Pro Ile Glu Ala Gly Ala Leu Leu Ala Thr Tyr Gly Arg Glu Arg<br>2900                          2905                          2910 | 8739 |
| gtg ggt gat ccg ttg tgg ttg ggg tcg ctg aag tcc aac atc ggg<br>Val Gly Asp Pro Leu Trp Leu Gly Ser Leu Lys Ser Asn Ile Gly<br>2915                          2920                          2925 | 8784 |
| cac act cag gcc gcc gcg ggt gtg ggt ggt gtc atc aag atg gtg<br>His Thr Gln Ala Ala Ala Gly Val Gly Gly Val Ile Lys Met Val<br>2930                          2935                          2940 | 8829 |
| gag gcg ctg cgt cat ggc acg ttg cct cgc act ctc cac gtc gat<br>Glu Ala Leu Arg His Gly Thr Leu Pro Arg Thr Leu His Val Asp<br>2945                          2950                          2955 | 8874 |
| gct ccc tct tcg aag gtc gag tgg ggt tcg ggt gcg gtg gag ctg<br>Ala Pro Ser Ser Lys Val Glu Trp Gly Ser Gly Ala Val Glu Leu<br>2960                          2965                          2970 | 8919 |
| ttg acc gag gct cga gcc tgg ccc cgg cgg gcg gat cgc aag cgc<br>Leu Thr Glu Ala Arg Ala Trp Pro Arg Arg Ala Asp Arg Lys Arg<br>2975                          2980                          2985 | 8964 |
| cgt gcg gcc gtc tcc gcc ttc ggc gtc agc ggc acc aac gct cat<br>Arg Ala Ala Val Ser Ala Phe Gly Val Ser Gly Thr Asn Ala His<br>2990                          2995                          3000 | 9009 |
| gtc gtc atc gag gaa ccg ccc gcc gag gtg tcg gcc gag tcg ctg<br>Val Val Ile Glu Glu Pro Pro Ala Glu Val Ser Ala Glu Ser Leu<br>3005                          3010                          3015 | 9054 |
| gtc gag ttg cct gct ggt gct ggt gct ggt gct ggt gct ggt gct<br>Val Glu Leu Pro Ala Gly Ala Gly Ala Gly Ala Gly Ala Gly Ala<br>3020                          3025                          3030 | 9099 |
| ggt gct ggt gct ggt gct ggg gtg tct tcg gtt gtg gcg tgg tcg<br>Gly Ala Gly Ala Gly Ala Gly Val Ser Ser Val Val Ala Trp Ser<br>3035                          3040                          3045 | 9144 |
| ttg tcg gct cgt tcg ggt gag gcg ttg cgg gcg cag gcg gtg cgg<br>Leu Ser Ala Arg Ser Gly Glu Ala Leu Arg Ala Gln Ala Val Arg<br>3050                          3055                          3060 | 9189 |
| ttg cgt gag cat gtg gag cgt gtt ggg gct gat ccg gtt gat gtt<br>Leu Arg Glu His Val Glu Arg Val Gly Ala Asp Pro Val Asp Val<br>3065                          3070                          3075 | 9234 |
| gcc ttt tcg ttg gcg gtg acg cgt gcg tcg ttc ggt gag cgt gcg<br>Ala Phe Ser Leu Ala Val Thr Arg Ala Ser Phe Gly Glu Arg Ala<br>3080                          3085                          3090 | 9279 |
| gtg gtc gtt ggt ggt gac cgt gcg gag ttg ttg gcg ggg ctg ggg<br>Val Val Val Gly Gly Asp Arg Ala Glu Leu Leu Ala Gly Leu Gly<br>3095                          3100                          3105 | 9324 |
| gct gtt gct gct ggg gat gcg ctg tcg ggc gtg gtg cgt ggt tcg<br>Ala Val Ala Ala Gly Asp Ala Leu Ser Gly Val Val Arg Gly Ser<br>3110                          3115                          3120 | 9369 |
| gcg gtg cgg ggg cga aag gtt gcg gct ttg ttt acg ggt cag ggt<br>Ala Val Arg Gly Arg Lys Val Ala Ala Leu Phe Thr Gly Gln Gly<br>3125                          3130                          3135 | 9414 |
| gcg cag tgg gtt ggt atg ggg cgt gag ttg tat ggg ttg gat ggg<br>Ala Gln Trp Val Gly Met Gly Arg Glu Leu Tyr Gly Leu Asp Gly<br>3140                          3145                          3150 | 9459 |
| gtg ttt gct gcg gcg ttg gat gag gtt ttg ggt gtg gtg ggg gag<br>Val Phe Ala Ala Ala Leu Asp Glu Val Leu Gly Val Val Gly Glu<br>3155                          3160                          3165 | 9504 |
| gtg ggt ggt tgg tct ttg cgt gag gtg atg ttt ggt gag ggt ggt<br>Val Gly Gly Trp Ser Leu Arg Glu Val Met Phe Gly Glu Gly Gly<br>3170                          3175                          3180 | 9549 |

| | | | | | | | | | | | | | | |
|---|---|---|---|---|---|---|---|---|---|---|---|---|---|---|
| ggt | gtt | ggg | gtg | ggg | ttg | ttg | gat | ggt | acg | gag | ttt | gcg | cag | cct | 9594 |
| Gly | Val | Gly | Val | Gly | Leu | Leu | Asp | Gly | Thr | Glu | Phe | Ala | Gln | Pro | |
| 3185 | | | | | 3190 | | | | | 3195 | | | | | |
| gct | ttg | ttt | gcg | ttg | gag | gtg | gcg | ttg | ttt | cgg | gct | gtg | gag | gct | 9639 |
| Ala | Leu | Phe | Ala | Leu | Glu | Val | Ala | Leu | Phe | Arg | Ala | Val | Glu | Ala | |
| 3200 | | | | | 3205 | | | | | 3210 | | | | | |
| cgg | ggg | gtg | cgg | gct | tcg | gtg | gtg | ttg | ggg | cat | tcg | gtg | ggg | gag | 9684 |
| Arg | Gly | Val | Arg | Ala | Ser | Val | Val | Leu | Gly | His | Ser | Val | Gly | Glu | |
| 3215 | | | | | 3220 | | | | | 3225 | | | | | |
| gtt | gct | gct | gcg | tgt | gtg | gcg | ggg | gtg | ttt | tcg | ctt | gcg | gat | gcg | 9729 |
| Val | Ala | Ala | Ala | Cys | Val | Ala | Gly | Val | Phe | Ser | Leu | Ala | Asp | Ala | |
| 3230 | | | | | 3235 | | | | | 3240 | | | | | |
| gcg | cgg | ttg | gtg | gtg | gcg | cgt | ggt | cgg | ttg | atg | ggt | ggg | ttg | cct | 9774 |
| Ala | Arg | Leu | Val | Val | Ala | Arg | Gly | Arg | Leu | Met | Gly | Gly | Leu | Pro | |
| 3245 | | | | | 3250 | | | | | 3255 | | | | | |
| gtg | ggt | ggg | ggg | atg | ttg | tcg | gtt | cgt | gcg | tct | gag | gcc | gaa | ctt | 9819 |
| Val | Gly | Gly | Gly | Met | Leu | Ser | Val | Arg | Ala | Ser | Glu | Ala | Glu | Leu | |
| 3260 | | | | | 3265 | | | | | 3270 | | | | | |
| gct | gat | gtt | gtg | gct | ggg | ttg | ggt | ggt | cgg | gtg | tcg | gtg | gct | gcg | 9864 |
| Ala | Asp | Val | Val | Ala | Gly | Leu | Gly | Gly | Arg | Val | Ser | Val | Ala | Ala | |
| 3275 | | | | | 3280 | | | | | 3285 | | | | | |
| gtc | aat | ggt | ccg | gcg | tcg | gtg | gtg | ttg | tct | ggt | gag | tgt | ggt | gcg | 9909 |
| Val | Asn | Gly | Pro | Ala | Ser | Val | Val | Leu | Ser | Gly | Glu | Cys | Gly | Ala | |
| 3290 | | | | | 3295 | | | | | 3300 | | | | | |
| ttg | gat | gtt | gtt | gcg | gcg | cgg | ttg | ggt | ggg | cgt | ggg | gtg | gag | tgc | 9954 |
| Leu | Asp | Val | Val | Ala | Ala | Arg | Leu | Gly | Gly | Arg | Gly | Val | Glu | Cys | |
| 3305 | | | | | 3310 | | | | | 3315 | | | | | |
| aag | cgg | ttg | gtg | gtg | tcg | cat | gcg | ttt | cat | tcg | gcg | ttg | atg | gag | 9999 |
| Lys | Arg | Leu | Val | Val | Ser | His | Ala | Phe | His | Ser | Ala | Leu | Met | Glu | |
| 3320 | | | | | 3325 | | | | | 3330 | | | | | |
| ccg | atg | ttg | gag | gag | ttt | cgt | ggg | gtt | gct | gag | agt | gtg | gag | tat | 10044 |
| Pro | Met | Leu | Glu | Glu | Phe | Arg | Gly | Val | Ala | Glu | Ser | Val | Glu | Tyr | |
| 3335 | | | | | 3340 | | | | | 3345 | | | | | |
| cgg | cgg | ccg | tgt | gtg | ccg | gtg | gtg | tcg | aat | gtg | acg | ggt | ggg | gtg | 10089 |
| Arg | Arg | Pro | Cys | Val | Pro | Val | Val | Ser | Asn | Val | Thr | Gly | Gly | Val | |
| 3350 | | | | | 3355 | | | | | 3360 | | | | | |
| gtt | ggg | ttt | gat | gag | ttg | ggt | tgt | gcc | gag | tat | tgg | gtg | cgg | cat | 10134 |
| Val | Gly | Phe | Asp | Glu | Leu | Gly | Cys | Ala | Glu | Tyr | Trp | Val | Arg | His | |
| 3365 | | | | | 3370 | | | | | 3375 | | | | | |
| gcg | cgg | gag | gcg | gtg | cgt | ttc | gct | gag | ggg | ata | cgg | gct | gct | cgt | 10179 |
| Ala | Arg | Glu | Ala | Val | Arg | Phe | Ala | Glu | Gly | Ile | Arg | Ala | Ala | Arg | |
| 3380 | | | | | 3385 | | | | | 3390 | | | | | |
| gct | ctt | ggt | gtg | gat | acg | ttc | ctg | gag | gtg | ggt | ccg | cat | gcg | gtt | 10224 |
| Ala | Leu | Gly | Val | Asp | Thr | Phe | Leu | Glu | Val | Gly | Pro | His | Ala | Val | |
| 3395 | | | | | 3400 | | | | | 3405 | | | | | |
| ttg | acg | gcg | atg | gct | ggt | cag | tgt | ctt | gat | gga | gag | gag | gct | gac | 10269 |
| Leu | Thr | Ala | Met | Ala | Gly | Gln | Cys | Leu | Asp | Gly | Glu | Glu | Ala | Asp | |
| 3410 | | | | | 3415 | | | | | 3420 | | | | | |
| ttg | gcg | ttt | gtg | ccg | gtc | ctg | cgg | cgt | gat | cgg | ccg | gca | ttg | cag | 10314 |
| Leu | Ala | Phe | Val | Pro | Val | Leu | Arg | Arg | Asp | Arg | Pro | Ala | Leu | Gln | |
| 3425 | | | | | 3430 | | | | | 3435 | | | | | |
| acc | ttc | acc | acc | gca | ctc | gcc | act | ctg | cac | acc | cgt | gat | gcc | gaa | 10359 |
| Thr | Phe | Thr | Thr | Ala | Leu | Ala | Thr | Leu | His | Thr | Arg | Asp | Ala | Glu | |
| 3440 | | | | | 3445 | | | | | 3450 | | | | | |
| ctc | gac | gcc | gtg | gcg | ctc | cat | tca | ggc | agc | gat | gcc | cgg | cgg | atc | 10404 |
| Leu | Asp | Ala | Val | Ala | Leu | His | Ser | Gly | Ser | Asp | Ala | Arg | Arg | Ile | |
| 3455 | | | | | 3460 | | | | | 3465 | | | | | |
| gac | ctg | ccc | acc | tac | ccc | ttc | caa | cgc | cgt | agc | tac | tgg | gcg | acc | 10449 |
| Asp | Leu | Pro | Thr | Tyr | Pro | Phe | Gln | Arg | Arg | Ser | Tyr | Trp | Ala | Thr | |
| 3470 | | | | | 3475 | | | | | 3480 | | | | | |

| | |
|---|---|
| ggt tcg gtg cct ggt gcc acc ggc acc tcg gcc gcg gcc cgc ttc<br>Gly Ser Val Pro Gly Ala Thr Gly Thr Ser Ala Ala Ala Arg Phe<br>3485 3490 3495 | 10494 |
| ggg ctc gta tgg aag gac cac ccg ttc ctc agc ggc gcg acg ccg<br>Gly Leu Val Trp Lys Asp His Pro Phe Leu Ser Gly Ala Thr Pro<br>3500 3505 3510 | 10539 |
| ata gcc ggc tcc gat tcg ctg ctc ctc acc ggc agg gtg gcg cct<br>Ile Ala Gly Ser Asp Ser Leu Leu Leu Thr Gly Arg Val Ala Pro<br>3515 3520 3525 | 10584 |
| tcc gca tac ccg tgg ctg gcc gat cac gcc att tcc ggc acg gtg<br>Ser Ala Tyr Pro Trp Leu Ala Asp His Ala Ile Ser Gly Thr Val<br>3530 3535 3540 | 10629 |
| ctg ctc cct ggg acg gcg atc gcc gac ctg ctg ctg cgg gcc gcc<br>Leu Leu Pro Gly Thr Ala Ile Ala Asp Leu Leu Leu Arg Ala Ala<br>3545 3550 3555 | 10674 |
| gac gag gtg ggc gcg ggc ggt gtc gag gaa ttc atg ctc cac gcg<br>Asp Glu Val Gly Ala Gly Gly Val Glu Glu Phe Met Leu His Ala<br>3560 3565 3570 | 10719 |
| ccc ctg ctc ctc ccc gaa cag ggc gga ctt cag ctc cag gtg ctg<br>Pro Leu Leu Leu Pro Glu Gln Gly Gly Leu Gln Leu Gln Val Leu<br>3575 3580 3585 | 10764 |
| gtc gag gcg gcc gat gaa cga ggc tgt cgc acc gtc tcg ctc gcc<br>Val Glu Ala Ala Asp Glu Arg Gly Cys Arg Thr Val Ser Leu Ala<br>3590 3595 3600 | 10809 |
| gca cgt ccc gag aat ccg ggg cgc gat ggc gag gcg ccg gag tgg<br>Ala Arg Pro Glu Asn Pro Gly Arg Asp Gly Glu Ala Pro Glu Trp<br>3605 3610 3615 | 10854 |
| acc agg cac gcg gag ggt gtg ctc gcg ccc gaa ggc ccg atc gca<br>Thr Arg His Ala Glu Gly Val Leu Ala Pro Glu Gly Pro Ile Ala<br>3620 3625 3630 | 10899 |
| ccg gag acc gca tgg gcc gtt ggg atc tgg ccg ccg ccc ggg gct<br>Pro Glu Thr Ala Trp Ala Val Gly Ile Trp Pro Pro Pro Gly Ala<br>3635 3640 3645 | 10944 |
| gag ccg gtc gac gtc gag gag ctg tac gag ggg ttc gcc gcg gac<br>Glu Pro Val Asp Val Glu Glu Leu Tyr Glu Gly Phe Ala Ala Asp<br>3650 3655 3660 | 10989 |
| ggc tac ggc tac ggc ccg gcc ttc acc gga ctg tcc ggg gtg tgg<br>Gly Tyr Gly Tyr Gly Pro Ala Phe Thr Gly Leu Ser Gly Val Trp<br>3665 3670 3675 | 11034 |
| cgc cgt ggt gag gag ctc ttc gcc gag gtg cag ctg ccc gac ggg<br>Arg Arg Gly Glu Glu Leu Phe Ala Glu Val Gln Leu Pro Asp Gly<br>3680 3685 3690 | 11079 |
| gtg gcg aac ggg gat aat ttc ggc att cat ccg gcc ctc ttc gac<br>Val Ala Asn Gly Asp Asn Phe Gly Ile His Pro Ala Leu Phe Asp<br>3695 3700 3705 | 11124 |
| gcg gct ctc cat cca tgg cgt gcc ggc ggg ctg gtg ccc gac acg<br>Ala Ala Leu His Pro Trp Arg Ala Gly Gly Leu Val Pro Asp Thr<br>3710 3715 3720 | 11169 |
| ggc ggc acg acg ctg gtg ccg ttc tcc tgg cag ggc att ggt ctc<br>Gly Gly Thr Thr Leu Val Pro Phe Ser Trp Gln Gly Ile Gly Leu<br>3725 3730 3735 | 11214 |
| cac gcc acc gga gcc gag aca ctg cgg gtc cgg ctg gcg acg gcg<br>His Ala Thr Gly Ala Glu Thr Leu Arg Val Arg Leu Ala Thr Ala<br>3740 3745 3750 | 11259 |
| ggt gac ggt gcc gac gcc gcc ttc tcg gtg cag gcc gcc gac ccg<br>Gly Asp Gly Ala Asp Ala Ala Phe Ser Val Gln Ala Ala Asp Pro<br>3755 3760 3765 | 11304 |
| gcc ggc cgg ccc gtc ctc acc ctg gac gcg cta ctg ctt cgc ccg<br>Ala Gly Arg Pro Val Leu Thr Leu Asp Ala Leu Leu Leu Arg Pro<br>3770 3775 3780 | 11349 |

-continued

| | | | | | | | | | | | | | |
|---|---|---|---|---|---|---|---|---|---|---|---|---|---|
| gtg | gcc | ctg | ggt | acg | gac | aac | gcg | tcg | gcg | tcg | ggg | ctg ctg tac | 11394 |
| Val | Ala | Leu | Gly | Thr | Asp | Asn | Ala | Ser | Ala | Ser | Gly | Leu Leu Tyr | |
| 3785 | | | | | 3790 | | | | | 3795 | | | |
| cac | gtc | gac | tgg | cag | ccg | gtg | ccg | cgg | cag | gca | gtt | gcc ccc ggc | 11439 |
| His | Val | Asp | Trp | Gln | Pro | Val | Pro | Arg | Gln | Ala | Val | Ala Pro Gly | |
| 3800 | | | | | 3805 | | | | | 3810 | | | |
| tcc | cgt | ggc | tgg | acg | gtt | ctc | ggg | ccc | gcc | gcg | agc | gaa acg gcg | 11484 |
| Ser | Arg | Gly | Trp | Thr | Val | Leu | Gly | Pro | Ala | Ala | Ser | Glu Thr Ala | |
| 3815 | | | | | 3820 | | | | | 3825 | | | |
| acg | gtg | gag | gtg | gca | cag | gag | gag | agc | gcg | acc | cta | cga gcc ctg | 11529 |
| Thr | Val | Glu | Val | Ala | Gln | Glu | Glu | Ser | Ala | Thr | Leu | Arg Ala Leu | |
| 3830 | | | | | 3835 | | | | | 3840 | | | |
| ccc | ggc | gcg | cag | ccc | gct | gtc | cac | gcc | gac | ctc | acc | gct ctg cgc | 11574 |
| Pro | Gly | Ala | Gln | Pro | Ala | Val | His | Ala | Asp | Leu | Thr | Ala Leu Arg | |
| 3845 | | | | | 3850 | | | | | 3855 | | | |
| gcc | gcc | ctg | gcc | gcc | gga | acc | gcc | gtt | ccc | ggg | ctg | gta gtg gtg | 11619 |
| Ala | Ala | Leu | Ala | Ala | Gly | Thr | Ala | Val | Pro | Gly | Leu | Val Val Val | |
| 3860 | | | | | 3865 | | | | | 3870 | | | |
| ccg | ccc | acc | ggc | acc | cac | ctc | gtc | gag | ccg | ggc | gcg | ggt acg ggc | 11664 |
| Pro | Pro | Thr | Gly | Thr | His | Leu | Val | Glu | Pro | Gly | Ala | Gly Thr Gly | |
| 3875 | | | | | 3880 | | | | | 3885 | | | |
| ggg | ggc | gcg | gag | acg | ggt | gcc | gca | ggc | tgg | ggc | gac | gac ccc gtg | 11709 |
| Gly | Gly | Ala | Glu | Thr | Gly | Ala | Ala | Gly | Trp | Gly | Asp | Asp Pro Val | |
| 3890 | | | | | 3895 | | | | | 3900 | | | |
| cgc | gcc | gcc | ctc | ggg | cgc | ggc | ctg | gcc | ctg | gta | cgg | gag tgg acc | 11754 |
| Arg | Ala | Ala | Leu | Gly | Arg | Gly | Leu | Ala | Leu | Val | Arg | Glu Trp Thr | |
| 3905 | | | | | 3910 | | | | | 3915 | | | |
| gag | gac | gaa | cgc | ctg | gtg | ggc | gcc | cag | ctt | gcc | gtc | ctc acc cgg | 11799 |
| Glu | Asp | Glu | Arg | Leu | Val | Gly | Ala | Gln | Leu | Ala | Val | Leu Thr Arg | |
| 3920 | | | | | 3925 | | | | | 3930 | | | |
| ggg | gcg | gtc | gag | gcc | cgg | ccc | ggc | gac | gtg | ccg | gat | ctg gcg ggt | 11844 |
| Gly | Ala | Val | Glu | Ala | Arg | Pro | Gly | Asp | Val | Pro | Asp | Leu Ala Gly | |
| 3935 | | | | | 3940 | | | | | 3945 | | | |
| gca | gcc | ttg | tgg | ggg | ctg | ctc | cgc | tcc | gcg | cag | tcg | gag tac ccc | 11889 |
| Ala | Ala | Leu | Trp | Gly | Leu | Leu | Arg | Ser | Ala | Gln | Ser | Glu Tyr Pro | |
| 3950 | | | | | 3955 | | | | | 3960 | | | |
| gac | cgc | ttc | acc | ctc | gtc | gac | ctg | gat | gac | tcc | ccc | gag tcc tgg | 11934 |
| Asp | Arg | Phe | Thr | Leu | Val | Asp | Leu | Asp | Asp | Ser | Pro | Glu Ser Trp | |
| 3965 | | | | | 3970 | | | | | 3975 | | | |
| gct | gcc | ctg | ccc | cag | gct | ctg | gcg | tcg | gga | gag | ccg | caa ctc gcc | 11979 |
| Ala | Ala | Leu | Pro | Gln | Ala | Leu | Ala | Ser | Gly | Glu | Pro | Gln Leu Ala | |
| 3980 | | | | | 3985 | | | | | 3990 | | | |
| ttg | cgc | gcc | ggg | acc | gta | ctc | gct | ccg | gct | ctc | gtg | ccg atc gcc | 12024 |
| Leu | Arg | Ala | Gly | Thr | Val | Leu | Ala | Pro | Ala | Leu | Val | Pro Ile Ala | |
| 3995 | | | | | 4000 | | | | | 4005 | | | |
| gac | cct | gcg | acg | gcc | gcg | acc | tcg | gcc | gtg | gcc | tcg | atg gcg agt | 12069 |
| Asp | Pro | Ala | Thr | Ala | Ala | Thr | Ser | Ala | Val | Ala | Ser | Met Ala Ser | |
| 4010 | | | | | 4015 | | | | | 4020 | | | |
| ggc | gcg | tcg | aca | gcg | acc | gat | gtt | ccc | gct | gcg | gac | gcc gca ttc | 12114 |
| Gly | Ala | Ser | Thr | Ala | Thr | Asp | Val | Pro | Ala | Ala | Asp | Ala Ala Phe | |
| 4025 | | | | | 4030 | | | | | 4035 | | | |
| gac | ccc | gac | ggg | acc | gta | ctg | atc | acc | ggc | gcc | acc | ggc gcc ctg | 12159 |
| Asp | Pro | Asp | Gly | Thr | Val | Leu | Ile | Thr | Gly | Ala | Thr | Gly Ala Leu | |
| 4040 | | | | | 4045 | | | | | 4050 | | | |
| ggg | cgg | cgg | gtg | gtc | ccg | cac | ctg | gca | cgt | cag | cac | ggc gtg cgg | 12204 |
| Gly | Arg | Arg | Val | Val | Pro | His | Leu | Ala | Arg | Gln | His | Gly Val Arg | |
| 4055 | | | | | 4060 | | | | | 4065 | | | |
| cat | atg | ctc | ctg | gtc | agc | agg | cgc | ggc | ccg | gac | gcc | ccc gaa gcc | 12249 |
| His | Met | Leu | Leu | Val | Ser | Arg | Arg | Gly | Pro | Asp | Ala | Pro Glu Ala | |
| 4070 | | | | | 4075 | | | | | 4080 | | | |

```
gcc ctc ctg gag cgg gag ctc gcc gac ctg cag gtc acc gcg acc     12294
Ala Leu Leu Glu Arg Glu Leu Ala Asp Leu Gln Val Thr Ala Thr
4085            4090                4095 ttc gcg atg tgc gac ctc gcc gac ccc gcg gac atc cgg aag gtc     12339
Phe Ala Met Cys Asp Leu Ala Asp Pro Ala Asp Ile Arg Lys Val
4100            4105                4110 atc tcc gcg gtg ccg ccg gcg cac ccg ctg acc ggt gtc gtg cac     12384
Ile Ser Ala Val Pro Pro Ala His Pro Leu Thr Gly Val Val His
4115            4120                4125 acc gcc ggc atg ctg gac gac gga gcc ctc gcc ggc ctg acg ccg     12429
Thr Ala Gly Met Leu Asp Asp Gly Ala Leu Ala Gly Leu Thr Pro
4130            4135                4140 gcg cgg ctc gat acc gtc ctc cgg ccg aaa gcc gac gcc gta cgg     12474
Ala Arg Leu Asp Thr Val Leu Arg Pro Lys Ala Asp Ala Val Arg
4145            4150                4155 aac ctg cac gag gcc act ctc gac cag ccg ttg cgc gcg ttc gtc     12519
Asn Leu His Glu Ala Thr Leu Asp Gln Pro Leu Arg Ala Phe Val
4160            4165                4170 ctg ttc tct gca gcg gcc ggg ctc ctg ggc cgc ccg ggg cag ggc     12564
Leu Phe Ser Ala Ala Ala Gly Leu Leu Gly Arg Pro Gly Gln Gly
4175            4180                4185 tcc tac gcg gcg gcc aac gcg gtc ctc gac gcg ttt gcg cgg gac     12609
Ser Tyr Ala Ala Ala Asn Ala Val Leu Asp Ala Phe Ala Arg Asp
4190            4195                4200 cgt cgt gcg gcc ggg ctg cct gct gtg tcc ctg gcc tgg gga ctg     12654
Arg Arg Ala Ala Gly Leu Pro Ala Val Ser Leu Ala Trp Gly Leu
4205            4210                4215 tgg gac gaa cgg gca ggc atg gcc ggc ggc ctg gac gac gtg gca     12699
Trp Asp Glu Arg Ala Gly Met Ala Gly Gly Leu Asp Asp Val Ala
4220            4225                4230 ctc cgt cgg ctg cgc cgc gag ggc atc gcg gcc atg ccg ccc gag     12744
Leu Arg Arg Leu Arg Arg Glu Gly Ile Ala Ala Met Pro Pro Glu
4235            4240                4245 caa gcc ctc gac ctg ctc gac ctg gcc ctg acc acg cac cgg gac     12789
Gln Ala Leu Asp Leu Leu Asp Leu Ala Leu Thr Thr His Arg Asp
4250            4255                4260 ggg ccc gcg gtc ctc gtc ccg ctc cta ctc gac ggg gcc gcc ctg     12834
Gly Pro Ala Val Leu Val Pro Leu Leu Leu Asp Gly Ala Ala Leu
4265            4270                4275 cgc cga acg gcc aag gag cac ggc gcg acc gcg gtg cca ccg ttg     12879
Arg Arg Thr Ala Lys Glu His Gly Ala Thr Ala Val Pro Pro Leu
4280            4285                4290 ttg cgc ggc ctg ctc ccc gcg gcc ctg cgc cgc ggg agc agc ggc     12924
Leu Arg Gly Leu Leu Pro Ala Ala Leu Arg Arg Gly Ser Ser Gly
4295            4300                4305 acc ggt acc gcg gca acg gcc gcc aac cgg cgg ggc aag ggc gcg     12969
Thr Gly Thr Ala Ala Thr Ala Ala Asn Arg Arg Gly Lys Gly Ala
4310            4315                4320 gag cct gtc gcc gga cgc gtc gcg cgg atc gtg gcg ctc ctg gca     13014
Glu Pro Val Ala Gly Arg Val Ala Arg Ile Val Ala Leu Leu Ala
4325            4330                4335 gat gag agg tcc gcg gcc ctg ctg gac ctg gtc acc gag cag gtc     13059
Asp Glu Arg Ser Ala Ala Leu Leu Asp Leu Val Thr Glu Gln Val
4340            4345                4350 gcc gag gta ctc ggt cac gcg tcg gcc gcc gaa gtc gac ccc gaa     13104
Ala Glu Val Leu Gly His Ala Ser Ala Ala Glu Val Asp Pro Glu
4355            4360                4365 cgt ccc ttc cgg gac atc ggc ttc gac tcc ctg gcg gcg gtg gag     13149
Arg Pro Phe Arg Asp Ile Gly Phe Asp Ser Leu Ala Ala Val Glu
4370            4375                4380
```

-continued

| | | |
|---|---|---|
| ctg cgc aac cgc ctc ggc cgc ctg gtc gac ctg cgg ctg ccg acc<br>Leu Arg Asn Arg Leu Gly Arg Leu Val Asp Leu Arg Leu Pro Thr<br>4385                           4390                           4395 | 13194 |
| aca ctc gcc ttc gac cgc ccc acg ccg aag gac gtg gcc gag tgg<br>Thr Leu Ala Phe Asp Arg Pro Thr Pro Lys Asp Val Ala Glu Trp<br>4400                         4405                          4410 | 13239 |
| ctc gac ggg gag ttg ccc cgc ccc gcc ggt tcg tca gcc gat tcc<br>Leu Asp Gly Glu Leu Pro Arg Pro Ala Gly Ser Ser Ala Asp Ser<br>4415                         4420                         4425 | 13284 |
| tcc gcg ctg gag ggg atc gac gaa ctc gcc cgg gcc gtc gcc ctg<br>Ser Ala Leu Glu Gly Ile Asp Glu Leu Ala Arg Ala Val Ala Leu<br>4430                         4435                       4440 | 13329 |
| ctg ggc ccg gac gac gcc cgg cga gcc gag gta cgg cag cgg ctc<br>Leu Gly Pro Asp Asp Ala Arg Arg Ala Glu Val Arg Gln Arg Leu<br>4445                         4450                       4455 | 13374 |
| act ggg ctg ctg gcc gag ctc gac acc ccc ggc cac ggc act gcc<br>Thr Gly Leu Leu Ala Glu Leu Asp Thr Pro Gly His Gly Thr Ala<br>4460                         4465                       4470 | 13419 |
| ggc ccc cga gac cgc acc gcc ccc gcc gat gcc gag agc acc ccg<br>Gly Pro Arg Asp Arg Thr Ala Pro Ala Asp Ala Glu Ser Thr Pro<br>4475                         4480                       4485 | 13464 |
| gcg act gtg gcg ggc cgg ctt gac gag gcg act gac gac gag atc<br>Ala Thr Val Ala Gly Arg Leu Asp Glu Ala Thr Asp Asp Glu Ile<br>4490                         4495                       4500 | 13509 |
| ttc gcc ttc ctg gac gag cag ctg tga<br>Phe Ala Phe Leu Asp Glu Gln Leu<br>4505                         4510 | 13536 |

<210> SEQ ID NO 4
<211> LENGTH: 4511
<212> TYPE: PRT
<213> ORGANISM: Streptomyces mycarofaciens

<400> SEQUENCE: 4

Met Leu Val Ser Gly Asp Leu Val Thr Ser Arg Ile Asp Asp Arg Ser
1               5                 10                15

Asp Ala Ile Ala Val Val Gly Met Ser Cys Arg Phe Pro Gly Ala Pro
              20                    25                    30

Gly Val Glu Glu Phe Trp Lys Leu Leu Thr Asp Gly Thr Glu Ala Val
                  35                40                    45

Ser Arg Ala Ala Asp Gly Arg Arg Gly Met Ile Glu Ala Val Gly
        50                    55                    60

Asp Phe Asp Ala Thr Phe Phe Gly Met Ser Pro Arg Glu Ala Ala Glu
65                  70                  75                    80

Thr Asp Pro Gln Gln Arg Leu Leu Leu Glu Leu Gly Trp Glu Ala Leu
                  85                90                    95

Glu Asp Ala Gly Ile Val Pro Gly Ser Leu Arg Gly Glu Ala Val Gly
              100                   105                  110

Ile Phe Val Gly Ala Met His Asn Asp Tyr Ala Thr Leu Leu His Arg
             115                   120                  125

Ala Gly Ala Pro Ala Gly Ala His Thr Ala Thr Gly Leu Gln Pro Ala
        130                    135                  140

Met Leu Ala Asn Arg Leu Ser Tyr Val Leu Gly Thr Arg Gly Pro Ser
145              150                155                160

Leu Ala Val Asp Thr Ala Gln Ser Ser Ser Leu Val Ala Val Ala Leu
                 165                170                175

Ala Val Glu Ser Leu Arg Ala Gly Thr Ser Arg Ile Ala Ile Ala Gly
             180                   185                  190

```
Gly Val Asn Leu Ile Leu Ala Asp Glu Gly Ser Ala Thr Met Glu Arg
        195                 200                 205

Leu Gly Ala Leu Ser Pro Asp Gly Arg Cys Tyr Thr Phe Asp Ala Arg
    210                 215                 220

Ala Asn Gly Tyr Val Arg Gly Glu Gly Gly Ala Val Val Leu Lys
225                 230                 235                 240

Pro Leu Ala Asp Ala Leu Ala Asp Gly Asp Pro Val Tyr Cys Val Val
                245                 250                 255

Arg Ser Ala Ala Thr Gly Asn Asp Gly Gly Pro Gly Leu Thr Ser
            260                 265                 270

Pro Asp His Glu Gly Gln Glu Ala Val Leu Arg Ala Ala Cys Ala Gln
        275                 280                 285

Ala Gly Val Asp Pro Ala Lys Val Arg Phe Val Glu Leu His Gly Thr
    290                 295                 300

Gly Thr Pro Val Gly Asp Pro Val Glu Ala Arg Ala Leu Gly Ala Val
305                 310                 315                 320

His Gly Ser Gly Arg Pro Ala Asp Ala Pro Leu Leu Val Gly Ser Val
                325                 330                 335

Lys Thr Asn Ile Gly His Leu Glu Gly Ala Ala Gly Ile Ala Gly Leu
            340                 345                 350

Val Lys Ala Ala Leu Cys Leu Arg Asn Arg Thr Leu Pro Gly Ser Leu
    355                 360                 365

Asn Phe Val Thr Pro His Pro Ala Ile Pro Leu Asp Arg Leu Arg Leu
370                 375                 380

Lys Val Gln Thr Thr Pro Thr Thr Leu His Pro Asp Pro Asp Gly Ser
385                 390                 395                 400

Pro Leu Leu Ala Gly Val Ser Ser Phe Gly Ile Gly Gly Thr Asn Cys
                405                 410                 415

His Val Val Leu Glu His Leu Pro Glu Pro Ala Pro Thr Thr Arg Glu
            420                 425                 430

Ala Leu Pro Ala Pro His Leu Val Pro Pro Leu Leu Leu Ser Ala Arg
    435                 440                 445

Ser His Pro Ala Leu Leu Ala Gln Ala Ala Arg Leu Arg Asp His Leu
    450                 455                 460

Ser Arg Thr Ala Ala Asp Pro Gln Asp Val Ala Tyr Ser Leu Ala Thr
465                 470                 475                 480

Thr Arg Ser Leu Phe Glu His Arg Ala Ala Leu Pro Cys Gly Asn Arg
                485                 490                 495

Glu Glu Leu Val Ala Ala Leu Asp Ala Leu Ala His Gly Arg Ile Thr
            500                 505                 510

Ala Gly Val Arg Val Asp Ser Ala Val Ser Gly Gly Thr Ala Val Leu
    515                 520                 525

Phe Thr Gly Gln Gly Ala Gln Trp Val Gly Met Gly Arg Glu Leu Tyr
    530                 535                 540

Gly Leu Asp Gly Val Phe Ala Ala Ala Leu Asp Glu Val Leu Gly Val
545                 550                 555                 560

Val Gly Glu Val Gly Gly Trp Ser Leu Arg Glu Val Met Phe Gly Glu
                565                 570                 575

Gly Gly Gly Val Gly Val Gly Leu Leu Asp Gly Thr Glu Phe Ala Gln
            580                 585                 590

Pro Ala Leu Phe Ala Leu Glu Val Ala Leu Phe Arg Ala Val Glu Ala
    595                 600                 605

Arg Gly Val Arg Ala Ser Val Val Leu Gly His Ser Val Gly Glu Val
```

```
                610             615             620
Ala Ala Ala Cys Val Ala Gly Val Phe Ser Leu Ala Asp Ala Ala Arg
625             630             635             640

Leu Val Val Ala Arg Gly Arg Leu Met Gly Ala Leu Pro Val Gly Gly
                645             650             655

Gly Met Leu Ser Val Arg Ala Ser Glu Ala Glu Leu Val Asp Val Val
                660             665             670

Ala Gly Leu Gly Gly Arg Val Ser Val Ala Ala Val Asn Gly Pro Ala
                675             680             685

Ser Val Val Leu Ser Gly Glu Cys Gly Ala Leu Asp Val Val Ala Ala
        690             695             700

Arg Leu Gly Gly Arg Gly Val Glu Cys Lys Arg Leu Val Val Ser His
705             710             715             720

Ala Phe His Ser Ala Leu Met Asp Pro Met Leu Glu Glu Phe Arg Gly
                725             730             735

Val Ala Glu Ser Val Glu Tyr Arg Arg Pro Cys Val Pro Val Val Ser
                740             745             750

Asn Val Thr Gly Gly Val Val Gly Phe Asp Glu Leu Gly Cys Ala Glu
                755             760             765

Tyr Trp Val Arg His Ala Arg Glu Ala Val Arg Phe Ala Glu Gly Ile
770             775             780

Arg Ala Ala Arg Ala Leu Gly Val Asp Thr Phe Leu Glu Val Gly Pro
785             790             795             800

His Ala Val Leu Thr Ala Met Ala Gly Gln Cys Leu Asp Ala Glu Glu
                805             810             815

Ala Asp Leu Ala Phe Val Pro Val Leu Arg Arg Asp Arg Pro Ala Leu
        820             825             830

Gln Thr Phe Thr Thr Ala Leu Ala Thr Leu His Thr Arg Asp Ala Glu
        835             840             845

Leu Asp Ala Val Ala Leu His Ser Gly Ser Asp Ala Arg Arg Ile Asp
        850             855             860

Leu Pro Thr Tyr Pro Phe Gln Arg Arg Thr His Trp Ser Pro Ala Leu
865             870             875             880

Ser His Gly His Ala Ala Gly Val Val Arg Ala Ser Thr Ala Thr Glu
                885             890             895

Ile Arg Gly Asn Asp Glu Ile Pro Glu Ser Ala Glu Ala Leu Leu Arg
                900             905             910

Asp Pro Ala Asp Gly Ser Leu Ala Ser Pro Glu Pro Ala Thr Pro
        915             920             925

Asp Gln Leu Val Arg Leu Val Arg Glu Thr Thr Ala Ala Val Leu Gly
        930             935             940

His Asp Asp Pro Asp Glu Ile Val Leu Asp Arg Thr Phe Thr Ser Gln
945             950             955             960

Gly Leu Glu Ser Val Thr Ala Val Glu Leu Arg Asp Leu Leu Asn Arg
                965             970             975

Ala Thr Gly Leu Thr Leu Ala Ala Thr Leu Val Tyr Asp Leu Pro Thr
        980             985             990

Pro Arg Ala Val Ala Asp Tyr Leu Ser Ala Ala Met Leu Ala Thr Asp
        995             1000             1005

Asp Ala  Asn Ser Ser Ala His  Gln Thr Thr Ala  Ala Thr Thr
        1010             1015             1020

Arg Ser  Gly Ala Arg Asn Asp  Asp Pro Ile Ala Ile  Val Gly Val
        1025             1030             1035
```

```
Gly Ser His Phe Pro Gly Gly Val Asp Ser Arg Ala Gly Leu Trp
        1040                1045                1050

Asp Leu Leu Ala Ser Gly Thr Asp Ala Ile Ser Ser Phe Pro Thr
    1055                1060                1065

Asp Arg Gly Trp Asp Leu Asn Glu Leu Tyr Asp Pro Glu Pro Gly
    1070                1075                1080

Ile Pro Gly Lys Thr Tyr Val Arg Gln Gly Gly Phe Leu His Gln
    1085                1090                1095

Ala Ala Glu Phe Asp Ala Glu Phe Phe Gly Ile Ser Pro Arg Glu
    1100                1105                1110

Ala Thr Ala Met Asp Pro Gln Gln Arg Leu Leu Leu Glu Thr Ser
    1115                1120                1125

Trp Glu Ala Leu Glu Asp Ala Gly Val Cys Pro Glu Ser Leu Arg
    1130                1135                1140

Gly Thr Asn Thr Gly Val Phe Ile Gly Ala Val Ala Pro Glu Tyr
    1145                1150                1155

Gly Pro Arg Leu His Glu Gly Ala Asp Gly Tyr Glu Gly Tyr Leu
    1160                1165                1170

Leu Thr Gly Thr Thr Ala Ser Val Ala Ser Gly Arg Ile Ala Tyr
    1175                1180                1185

Thr Phe Gly Thr Arg Gly Pro Ala Leu Thr Val Asp Thr Ala Cys
    1190                1195                1200

Ser Ser Ser Leu Val Ala Leu His Leu Ala Val Gln Ser Leu Arg
    1205                1210                1215

Arg Gly Glu Cys Asp Met Ala Leu Ala Gly Gly Ala Thr Val Met
    1220                1225                1230

Ser Gly Pro Gly Met Phe Val Glu Phe Ser Arg Gln Arg Gly Leu
    1235                1240                1245

Ala Ser Asp Gly Arg Cys Lys Ala Phe Ser Ala Asp Ala Asp Gly
    1250                1255                1260

Thr Ala Trp Ser Glu Gly Val Ala Val Leu Ala Leu Glu Arg Leu
    1265                1270                1275

Ser Asp Ala Arg Arg Ala Gly His Arg Val Leu Ala Leu Val Arg
    1280                1285                1290

Gly Ser Ala Val Asn Gln Asp Gly Ala Ser Asn Gly Leu Thr Ala
    1295                1300                1305

Pro Ser Gly Pro Ala Gln Glu Ser Val Ile Arg Glu Ala Leu Ala
    1310                1315                1320

Asp Ala Gly Leu Gly Pro Gly Asp Val Asp Val Val Glu Ala His
    1325                1330                1335

Gly Thr Gly Thr Ala Leu Gly Asp Pro Ile Glu Ala Gly Ala Leu
    1340                1345                1350

Leu Ala Thr Tyr Gly Cys Glu Arg Val Gly Asp Pro Leu Trp Leu
    1355                1360                1365

Gly Ser Leu Lys Ser Asn Ile Gly His Thr Gln Ala Ala Ala Gly
    1370                1375                1380

Val Ala Gly Val Ile Lys Met Val Glu Ala Leu Arg His Gly Thr
    1385                1390                1395

Leu Pro Arg Thr Leu His Ala Asp Arg Pro Ser Thr His Val Asp
    1400                1405                1410

Trp Ser Ser Gly Gly Val Glu Leu Leu Thr Glu Ala Arg Pro Trp
    1415                1420                1425

Pro Glu Arg Glu Gly Arg Pro Arg Arg Ala Ala Val Ser Ala Phe
    1430                1435                1440
```

```
Gly Val Ser Gly Thr Asn Ala His Leu Val Ile Glu Glu Pro Pro
    1445                1450                1455

Val Glu Leu Pro Ala Gly Ala Gly Ala Gly Ala Gly Ala
    1460                1465                1470

Gly Val Ser Ser Val Val Ala Trp Pro Leu Ser Ala Arg Ser Gly
    1475                1480                1485

Glu Ala Leu Arg Ala Gln Ala Val Arg Leu Arg Glu His Val Glu
    1490                1495                1500

Arg Val Gly Ala Asp Pro Val Asp Val Ala Phe Ser Leu Ala Val
    1505                1510                1515

Thr Arg Ala Ser Phe Gly Glu Arg Ala Val Val Val Gly Gly Asp
    1520                1525                1530

Arg Ala Glu Leu Leu Ala Gly Leu Asp Ala Leu Ala Gly Gly Arg
    1535                1540                1545

Arg Gly Pro Gly Val Val Arg Gly Ser Ala Val Ser Gly Gly Thr
    1550                1555                1560

Ala Val Leu Phe Thr Gly Gln Gly Ala Gln Trp Val Gly Met Gly
    1565                1570                1575

Arg Glu Leu Tyr Gly Leu Asp Gly Val Phe Ala Ala Ala Leu Asp
    1580                1585                1590

Glu Val Leu Gly Val Val Gly Glu Val Gly Gly Trp Ser Leu Arg
    1595                1600                1605

Glu Val Met Phe Gly Glu Gly Gly Gly Val Gly Val Gly Leu Leu
    1610                1615                1620

Asp Gly Thr Glu Phe Ala Gln Pro Ala Leu Phe Ala Leu Glu Val
    1625                1630                1635

Ala Leu Phe Arg Ala Val Glu Ala Arg Gly Val Arg Ala Ser Val
    1640                1645                1650

Val Leu Gly His Ser Val Gly Glu Val Ala Ala Ala Cys Val Ala
    1655                1660                1665

Gly Val Phe Ser Leu Ala Asp Ala Ala Arg Leu Val Val Ala Arg
    1670                1675                1680

Gly Arg Leu Met Gly Gly Leu Pro Val Gly Gly Gly Met Leu Ser
    1685                1690                1695

Val Arg Ala Ser Glu Ala Glu Leu Ala Asp Val Val Ala Gly Leu
    1700                1705                1710

Gly Gly Arg Val Ser Val Ala Ala Val Asn Gly Pro Ala Ser Val
    1715                1720                1725

Val Leu Ser Gly Glu Cys Gly Ala Leu Asp Val Val Ala Ala Arg
    1730                1735                1740

Leu Gly Gly Arg Gly Val Glu Cys Lys Arg Leu Val Val Ser His
    1745                1750                1755

Ala Phe His Ser Ala Leu Met Glu Pro Met Leu Glu Glu Phe Arg
    1760                1765                1770

Gly Val Ala Glu Ser Val Glu Tyr Arg Arg Pro Cys Val Pro Val
    1775                1780                1785

Val Ser Asn Val Thr Gly Gly Val Val Gly Phe Asp Glu Leu Gly
    1790                1795                1800

Cys Ala Glu Tyr Trp Val Arg His Ala Arg Glu Ala Val Arg Phe
    1805                1810                1815

Ala Glu Gly Ile Arg Ala Ala Arg Ala Leu Gly Val Asp Thr Phe
    1820                1825                1830

Leu Glu Val Gly Pro His Ala Val Leu Thr Ala Met Ala Gly Gln
```

```
                  1835                1840                1845

Cys Leu Asp Gly Glu Glu Ala Asp Leu Ala Phe Val Pro Val Leu
        1850                1855                1860

Arg Arg Asp Arg Pro Ala Ser Gln Thr Phe Thr Thr Ala Leu Ala
        1865                1870                1875

Thr Leu Cys Val Arg Gly Thr Glu Val Asp Trp Ala Thr Pro His
        1880                1885                1890

Arg Lys Ser Gly Ala Gln Arg Ile Asp Leu Pro Thr Tyr Pro Phe
        1895                1900                1905

Gln Arg Ala Arg Tyr Trp Leu Asp Pro Ala Pro Ala Met Ala Leu
        1910                1915                1920

Thr Thr Val Ala Ala Ser Ser Ala Glu Ala Ala Ala Thr Ala Thr
        1925                1930                1935

Glu Gly Thr Ala Leu Glu Thr Ala Gly Leu Arg Tyr Arg Ile Ala
        1940                1945                1950

Trp Gln Ala Ala Ala Thr Asp Arg Gly Thr Ser Arg Ser Ala Gly
        1955                1960                1965

His Val Val Leu Leu Thr Ser Asp Asp Ala Thr Glu Ser Gly
        1970                1975                1980

Leu Ala Ala Ala Ile Thr Arg Glu Leu Ala Val Arg Gly Ala Glu
        1985                1990                1995

Val Arg Thr Ala Ile Leu Pro Val Gly Thr Asp Arg Glu Thr Ala
        2000                2005                2010

Ala Asp Leu Leu Arg Thr Ser Gly Asp Gly Ala Ala Arg Ser Thr
        2015                2020                2025

His Val Leu Trp Leu Ala Pro Ala Glu Pro Asp Thr Ala Asp Ala
        2030                2035                2040

Val Ala Leu Ile Gln Ala Leu Gly Glu Ala Gly His Asp Ala Pro
        2045                2050                2055

Leu Trp Ile Ala Thr Arg Asp Ala Val Ala Val Gln Pro Gly Glu
        2060                2065                2070

Lys Leu Ser Val Ala Gly Ala Gln Leu Trp Gly Leu Gly Gln Val
        2075                2080                2085

Ala Ala Leu Glu Leu Phe Gln Arg Trp Gly Gly Leu Val Asp Leu
        2090                2095                2100

Pro Glu Asn Pro Ser Pro Ala Ala Val Arg Ala Phe Val Gly Ala
        2105                2110                2115

Leu Phe Ala Glu Gly Asp Asp Asn Gln Ile Ala Val Arg Pro Ser
        2120                2125                2130

Gly Val Tyr Val Arg Arg Val Ala Pro Ala Pro Ala Pro Ala Pro
        2135                2140                2145

Ala Leu Ile Gly Gln Ala Ala Gln Asp Asp Arg Ser Gly Pro Ser
        2150                2155                2160

Asp Gly Leu Asp Gly Asn Asn Gly Thr Ala Pro Val Asn Trp His
        2165                2170                2175

Pro Ser Gly Thr Val Leu Ile Thr Gly Gly Thr Gly Ala Leu Gly
        2180                2185                2190

Ala Gln Val Ala Arg Arg Leu Ala Arg Ala Gly Ala Pro His Leu
        2195                2200                2205

Leu Leu Val Ser Arg Arg Gly Pro Asp Gly Pro Gly Thr Gly Glu
        2210                2215                2220

Leu Val Gly Glu Leu Thr Ala His Gly Thr Glu Val Thr Val Thr
        2225                2230                2235
```

```
Ala Cys Asp Ala Ala Asp Arg Asp Ala Leu Ala Glu Leu Leu Ala
2240                2245                2250

Ser Ile Pro Glu Asp Arg Pro Leu Thr Ala Val Leu His Ala Ala
2255                2260                2265

Gly Val Leu Asp Asp Gly Val Leu Asp Ala Leu Thr Pro Asp Arg
2270                2275                2280

Leu Asp Ala Val Leu Arg Ala Lys Val Thr Val Ala Arg His Leu
2285                2290                2295

Asp Glu Leu Thr Ala Gly Ile Pro Leu Asp Ala Phe Val Leu Phe
2300                2305                2310

Ser Ser Ile Val Gly Val Trp Gly Asn Gly Gly Gln Gly Gly Tyr
2315                2320                2325

Ala Ala Ala Asn Ala Ala Leu Asp Ala Leu Ala His Arg Arg Arg
2330                2335                2340

Ala Arg Gly Gln Arg Ala Thr Ser Ile Ala Trp Gly Pro Trp Ala
2345                2350                2355

Gly Ala Gly Met Ala Ala Gly Ala Gly Ser Lys Ala Phe Gln Arg
2360                2365                2370

Asp Gly Ile Gln Ala Leu Asp Pro Glu Arg Ala Leu Asn Val Leu
2375                2380                2385

Asp Asp Val Val Arg Ala Asp Glu Thr Ser Val Ala Ala Glu Pro
2390                2395                2400

Ser Leu Ile Val Ala Asp Val Asp Trp Ser Thr Phe Val Gly Arg
2405                2410                2415

Ser Val Ala Arg Arg Thr Trp Ala Leu Phe Asp Gly Val Pro Ala
2420                2425                2430

Ala Cys Ser Ala Arg Ser Ala Gln Ala Ala Gln Gly Arg Ser Ala
2435                2440                2445

His Ala Pro Gly Glu Arg Pro His His Gly Gly Ile Gly Gly Ser
2450                2455                2460

Gly Asp Gly Ala Asp Glu Asp Arg Pro Trp Leu Ser Ala Gly Pro
2465                2470                2475

Ser Ser Pro Glu Arg Arg Arg Ala Leu Leu Asp Leu Val Arg Ser
2480                2485                2490

Glu Ala Ala Glu Ile Leu Arg His Gly Ser Ala Ala Ala Val Asp
2495                2500                2505

Pro Glu Thr Ala Phe Arg Ala Ala Gly Phe Asp Ser Leu Thr Val
2510                2515                2520

Leu Glu Leu Arg Asn Arg Leu Thr Ala Ala Ile Gly Leu Asn Leu
2525                2530                2535

Pro Ser Thr Leu Leu Phe Asp Tyr Pro Asn Pro Asn Ala Leu Ala
2540                2545                2550

Asp His Leu His Asp Glu Leu Phe Gly Ala Asp Ser Glu Ala Pro
2555                2560                2565

Leu Ala Ala Asn Thr Pro Thr Arg Ala Ser Ala Asp Asp Arg Glu
2570                2575                2580

Pro Ile Ala Val Val Gly Met Ala Cys Arg Tyr Pro Gly Gly Val
2585                2590                2595

Ala Ala Pro Glu Glu Leu Trp Asp Leu Val Ala Gly Gly His
2600                2605                2610

Ala Ile Ser Pro Leu Pro Ala Asn Arg Gly Trp Asp Leu Glu Gly
2615                2620                2625

Leu Tyr Asp Pro Glu Pro Gly Val Pro Gly Lys Ser Tyr Val Arg
2630                2635                2640
```

-continued

Glu Gly Gly Phe Leu His Gly Ala Ala Glu Phe Asp Ala Glu Phe
2645             2650             2655

Phe Gly Val Ser Pro Arg Glu Ala Ala Ala Met Asp Pro Gln Gln
2660             2665             2670

Arg Leu Leu Leu Glu Thr Ser Trp Glu Ala Leu Glu Arg Ala Gly
2675             2680             2685

Ile Val Pro Ala Ala Leu Arg Gly Thr Arg Thr Gly Val Phe Thr
2690             2695             2700

Gly Ile Ser Gln Gln Asp Tyr Ala Ala Gln Leu Gly Asp Ala Ala
2705             2710             2715

Glu Thr Tyr Gly Gly His Val Leu Thr Gly Asn Leu Gly Ser Val
2720             2725             2730

Val Ser Gly Arg Val Ala Tyr Ser Leu Gly Leu Glu Gly Pro Ala
2735             2740             2745

Leu Thr Val Asp Thr Ala Cys Ser Ser Ser Leu Val Ala Leu His
2750             2755             2760

Leu Ala Val Gln Ser Leu Arg Arg Gly Glu Cys Asp Met Ala Leu
2765             2770             2775

Ala Gly Gly Val Thr Val Met Ala Thr Pro Thr Val Phe Val Glu
2780             2785             2790

Phe Ser Arg Gln Arg Gly Leu Ala Ser Asp Gly Arg Cys Lys Ala
2795             2800             2805

Phe Ala Glu Gly Ala Asp Gly Thr Ala Trp Gly Glu Gly Val Gly
2810             2815             2820

Val Leu Leu Val Glu Arg Leu Ser Asp Ala Arg Arg Leu Gly His
2825             2830             2835

Ser Val Leu Ala Val Val Arg Gly Ser Ala Val Asn Gln Asp Gly
2840             2845             2850

Ala Ser Asn Gly Leu Thr Ala Pro Ser Gly Pro Ala Gln Gln Arg
2855             2860             2865

Val Ile Arg Glu Ala Leu Ala Asp Ala Gly Leu Gly Ser Gly Asp
2870             2875             2880

Val Asp Val Val Glu Ala His Gly Thr Gly Thr Ala Leu Gly Asp
2885             2890             2895

Pro Ile Glu Ala Gly Ala Leu Leu Ala Thr Tyr Gly Arg Glu Arg
2900             2905             2910

Val Gly Asp Pro Leu Trp Leu Gly Ser Leu Lys Ser Asn Ile Gly
2915             2920             2925

His Thr Gln Ala Ala Ala Gly Val Gly Gly Val Ile Lys Met Val
2930             2935             2940

Glu Ala Leu Arg His Gly Thr Leu Pro Arg Thr Leu His Val Asp
2945             2950             2955

Ala Pro Ser Ser Lys Val Glu Trp Gly Ser Gly Ala Val Glu Leu
2960             2965             2970

Leu Thr Glu Ala Arg Ala Trp Pro Arg Arg Ala Asp Arg Lys Arg
2975             2980             2985

Arg Ala Ala Val Ser Ala Phe Gly Val Ser Gly Thr Asn Ala His
2990             2995             3000

Val Val Ile Glu Glu Pro Pro Ala Glu Val Ser Ala Glu Ser Leu
3005             3010             3015

Val Glu Leu Pro Ala Gly Ala Gly Ala Gly Ala Gly Ala Gly Ala
3020             3025             3030

Gly Ala Gly Ala Gly Ala Gly Val Ser Ser Val Val Ala Trp Ser

-continued

```
            3035                3040                3045

Leu Ser Ala Arg Ser Gly Glu Ala Leu Arg Ala Gln Ala Val Arg
        3050                3055                3060

Leu Arg Glu His Val Glu Arg Val Gly Ala Asp Pro Val Asp Val
    3065                3070                3075

Ala Phe Ser Leu Ala Val Thr Arg Ala Ser Phe Gly Glu Arg Ala
    3080                3085                3090

Val Val Val Gly Gly Asp Arg Ala Glu Leu Leu Ala Gly Leu Gly
    3095                3100                3105

Ala Val Ala Ala Gly Asp Ala Leu Ser Gly Val Val Arg Gly Ser
    3110                3115                3120

Ala Val Arg Gly Arg Lys Val Ala Ala Leu Phe Thr Gly Gln Gly
    3125                3130                3135

Ala Gln Trp Val Gly Met Gly Arg Glu Leu Tyr Gly Leu Asp Gly
    3140                3145                3150

Val Phe Ala Ala Ala Leu Asp Glu Val Leu Gly Val Val Gly Glu
    3155                3160                3165

Val Gly Gly Trp Ser Leu Arg Glu Val Met Phe Gly Glu Gly Gly
    3170                3175                3180

Gly Val Gly Val Gly Leu Leu Asp Gly Thr Glu Phe Ala Gln Pro
    3185                3190                3195

Ala Leu Phe Ala Leu Glu Val Ala Leu Phe Arg Ala Val Glu Ala
    3200                3205                3210

Arg Gly Val Arg Ala Ser Val Val Leu Gly His Ser Val Gly Glu
    3215                3220                3225

Val Ala Ala Ala Cys Val Ala Gly Val Phe Ser Leu Ala Asp Ala
    3230                3235                3240

Ala Arg Leu Val Val Ala Arg Gly Arg Leu Met Gly Gly Leu Pro
    3245                3250                3255

Val Gly Gly Gly Met Leu Ser Val Arg Ala Ser Glu Ala Glu Leu
    3260                3265                3270

Ala Asp Val Val Ala Gly Leu Gly Gly Arg Val Ser Val Ala Ala
    3275                3280                3285

Val Asn Gly Pro Ala Ser Val Val Leu Ser Gly Glu Cys Gly Ala
    3290                3295                3300

Leu Asp Val Val Ala Ala Arg Leu Gly Gly Arg Gly Val Glu Cys
    3305                3310                3315

Lys Arg Leu Val Val Ser His Ala Phe His Ser Ala Leu Met Glu
    3320                3325                3330

Pro Met Leu Glu Glu Phe Arg Gly Val Ala Glu Ser Val Glu Tyr
    3335                3340                3345

Arg Arg Pro Cys Val Pro Val Val Ser Asn Val Thr Gly Gly Val
    3350                3355                3360

Val Gly Phe Asp Glu Leu Gly Cys Ala Glu Tyr Trp Val Arg His
    3365                3370                3375

Ala Arg Glu Ala Val Arg Phe Ala Glu Gly Ile Arg Ala Ala Arg
    3380                3385                3390

Ala Leu Gly Val Asp Thr Phe Leu Glu Val Gly Pro His Ala Val
    3395                3400                3405

Leu Thr Ala Met Ala Gly Gln Cys Leu Asp Gly Glu Glu Ala Asp
    3410                3415                3420

Leu Ala Phe Val Pro Val Leu Arg Arg Asp Arg Pro Ala Leu Gln
    3425                3430                3435
```

```
Thr Phe Thr Thr Ala Leu Ala Thr Leu His Thr Arg Asp Ala Glu
3440                3445                3450

Leu Asp Ala Val Ala Leu His Ser Gly Ser Asp Ala Arg Arg Ile
3455                3460                3465

Asp Leu Pro Thr Tyr Pro Phe Gln Arg Arg Ser Tyr Trp Ala Thr
3470                3475                3480

Gly Ser Val Pro Gly Ala Thr Gly Thr Ser Ala Ala Ala Arg Phe
3485                3490                3495

Gly Leu Val Trp Lys Asp His Pro Phe Leu Ser Gly Ala Thr Pro
3500                3505                3510

Ile Ala Gly Ser Asp Ser Leu Leu Thr Gly Arg Val Ala Pro
3515                3520                3525

Ser Ala Tyr Pro Trp Leu Ala Asp His Ala Ile Ser Gly Thr Val
3530                3535                3540

Leu Leu Pro Gly Thr Ala Ile Ala Asp Leu Leu Leu Arg Ala Ala
3545                3550                3555

Asp Glu Val Gly Ala Gly Val Glu Glu Phe Met Leu His Ala
3560                3565                3570

Pro Leu Leu Leu Pro Glu Gln Gly Gly Leu Gln Leu Gln Val Leu
3575                3580                3585

Val Glu Ala Ala Asp Glu Arg Gly Cys Arg Thr Val Ser Leu Ala
3590                3595                3600

Ala Arg Pro Glu Asn Pro Gly Arg Asp Gly Glu Ala Pro Glu Trp
3605                3610                3615

Thr Arg His Ala Glu Gly Val Leu Ala Pro Glu Gly Pro Ile Ala
3620                3625                3630

Pro Glu Thr Ala Trp Ala Val Gly Ile Trp Pro Pro Gly Ala
3635                3640                3645

Glu Pro Val Asp Val Glu Glu Leu Tyr Glu Gly Phe Ala Ala Asp
3650                3655                3660

Gly Tyr Gly Tyr Gly Pro Ala Phe Thr Gly Leu Ser Gly Val Trp
3665                3670                3675

Arg Arg Gly Glu Glu Leu Phe Ala Glu Val Gln Leu Pro Asp Gly
3680                3685                3690

Val Ala Asn Gly Asp Asn Phe Gly Ile His Pro Ala Leu Phe Asp
3695                3700                3705

Ala Ala Leu His Pro Trp Arg Ala Gly Gly Leu Val Pro Asp Thr
3710                3715                3720

Gly Gly Thr Thr Leu Val Pro Phe Ser Trp Gln Gly Ile Gly Leu
3725                3730                3735

His Ala Thr Gly Ala Glu Thr Leu Arg Val Arg Leu Ala Thr Ala
3740                3745                3750

Gly Asp Gly Ala Asp Ala Ala Phe Ser Val Gln Ala Ala Asp Pro
3755                3760                3765

Ala Gly Arg Pro Val Leu Thr Leu Asp Ala Leu Leu Leu Arg Pro
3770                3775                3780

Val Ala Leu Gly Thr Asp Asn Ala Ser Ala Ser Gly Leu Leu Tyr
3785                3790                3795

His Val Asp Trp Gln Pro Val Pro Arg Gln Ala Val Ala Pro Gly
3800                3805                3810

Ser Arg Gly Trp Thr Val Leu Gly Pro Ala Ala Ser Glu Thr Ala
3815                3820                3825

Thr Val Glu Val Ala Gln Glu Glu Ser Ala Thr Leu Arg Ala Leu
3830                3835                3840
```

Pro Gly Ala Gln Pro Ala Val His Ala Asp Leu Thr Ala Leu Arg
    3845              3850              3855

Ala Ala Leu Ala Ala Gly Thr Ala Val Pro Gly Leu Val Val Val
    3860              3865              3870

Pro Pro Thr Gly Thr His Leu Val Glu Pro Gly Ala Gly Thr Gly
    3875              3880              3885

Gly Gly Ala Glu Thr Gly Ala Ala Gly Trp Gly Asp Asp Pro Val
    3890              3895              3900

Arg Ala Ala Leu Gly Arg Gly Leu Ala Leu Val Arg Glu Trp Thr
    3905              3910              3915

Glu Asp Glu Arg Leu Val Gly Ala Gln Leu Ala Val Leu Thr Arg
    3920              3925              3930

Gly Ala Val Glu Ala Arg Pro Gly Asp Val Pro Asp Leu Ala Gly
    3935              3940              3945

Ala Ala Leu Trp Gly Leu Leu Arg Ser Ala Gln Ser Glu Tyr Pro
    3950              3955              3960

Asp Arg Phe Thr Leu Val Asp Leu Asp Asp Ser Pro Glu Ser Trp
    3965              3970              3975

Ala Ala Leu Pro Gln Ala Leu Ala Ser Gly Glu Pro Gln Leu Ala
    3980              3985              3990

Leu Arg Ala Gly Thr Val Leu Ala Pro Ala Leu Val Pro Ile Ala
    3995              4000              4005

Asp Pro Ala Thr Ala Ala Thr Ser Ala Val Ala Ser Met Ala Ser
    4010              4015              4020

Gly Ala Ser Thr Ala Thr Asp Val Pro Ala Ala Asp Ala Ala Phe
    4025              4030              4035

Asp Pro Asp Gly Thr Val Leu Ile Thr Gly Ala Thr Gly Ala Leu
    4040              4045              4050

Gly Arg Arg Val Val Pro His Leu Ala Arg Gln His Gly Val Arg
    4055              4060              4065

His Met Leu Leu Val Ser Arg Arg Gly Pro Asp Ala Pro Glu Ala
    4070              4075              4080

Ala Leu Leu Glu Arg Glu Leu Ala Asp Leu Gln Val Thr Ala Thr
    4085              4090              4095

Phe Ala Met Cys Asp Leu Ala Asp Pro Ala Asp Ile Arg Lys Val
    4100              4105              4110

Ile Ser Ala Val Pro Pro Ala His Pro Leu Thr Gly Val Val His
    4115              4120              4125

Thr Ala Gly Met Leu Asp Asp Gly Ala Leu Ala Gly Leu Thr Pro
    4130              4135              4140

Ala Arg Leu Asp Thr Val Leu Arg Pro Lys Ala Asp Ala Val Arg
    4145              4150              4155

Asn Leu His Glu Ala Thr Leu Asp Gln Pro Leu Arg Ala Phe Val
    4160              4165              4170

Leu Phe Ser Ala Ala Ala Gly Leu Leu Gly Arg Pro Gly Gln Gly
    4175              4180              4185

Ser Tyr Ala Ala Ala Asn Ala Val Leu Asp Ala Phe Ala Arg Asp
    4190              4195              4200

Arg Arg Ala Ala Gly Leu Pro Ala Val Ser Leu Ala Trp Gly Leu
    4205              4210              4215

Trp Asp Glu Arg Ala Gly Met Ala Gly Gly Leu Asp Asp Val Ala
    4220              4225              4230

Leu Arg Arg Leu Arg Arg Glu Gly Ile Ala Ala Met Pro Pro Glu

| | | | | | | | | | | |
|---|---|---|---|---|---|---|---|---|---|---|
| | | 4235 | | | 4240 | | | 4245 | | |

Gln Ala Leu Asp Leu Leu Asp Leu Ala Leu Thr Thr His Arg Asp
            4250                4255                4260

Gly Pro Ala Val Leu Val Pro Leu Leu Leu Asp Gly Ala Ala Leu
        4265                4270                4275

Arg Arg Thr Ala Lys Glu His Gly Ala Thr Ala Val Pro Pro Leu
    4280                4285                4290

Leu Arg Gly Leu Leu Pro Ala Ala Leu Arg Arg Gly Ser Ser Gly
4295                4300                4305

Thr Gly Thr Ala Ala Thr Ala Ala Asn Arg Arg Gly Lys Gly Ala
4310                4315                4320

Glu Pro Val Ala Gly Arg Val Ala Arg Ile Val Ala Leu Leu Ala
4325                4330                4335

Asp Glu Arg Ser Ala Ala Leu Leu Asp Leu Val Thr Glu Gln Val
4340                4345                4350

Ala Glu Val Leu Gly His Ala Ser Ala Ala Glu Val Asp Pro Glu
4355                4360                4365

Arg Pro Phe Arg Asp Ile Gly Phe Asp Ser Leu Ala Ala Val Glu
4370                4375                4380

Leu Arg Asn Arg Leu Gly Arg Leu Val Asp Leu Arg Leu Pro Thr
4385                4390                4395

Thr Leu Ala Phe Asp Arg Pro Thr Pro Lys Asp Val Ala Glu Trp
4400                4405                4410

Leu Asp Gly Glu Leu Pro Arg Pro Ala Gly Ser Ser Ala Asp Ser
4415                4420                4425

Ser Ala Leu Glu Gly Ile Asp Glu Leu Ala Arg Ala Val Ala Leu
4430                4435                4440

Leu Gly Pro Asp Asp Ala Arg Arg Ala Glu Val Arg Gln Arg Leu
4445                4450                4455

Thr Gly Leu Leu Ala Glu Leu Asp Thr Pro Gly His Gly Thr Ala
4460                4465                4470

Gly Pro Arg Asp Arg Thr Ala Pro Ala Asp Ala Glu Ser Thr Pro
4475                4480                4485

Ala Thr Val Ala Gly Arg Leu Asp Glu Ala Thr Asp Asp Glu Ile
4490                4495                4500

Phe Ala Phe Leu Asp Glu Gln Leu
4505                4510

<210> SEQ ID NO 5
<211> LENGTH: 5835
<212> TYPE: DNA
<213> ORGANISM: Streptomyces mycarofaciens
<220> FEATURE:
<221> NAME/KEY: CDS
<222> LOCATION: (1)..(5832)

<400> SEQUENCE: 5

| | | | | | | | | | | | | | | | |
|---|---|---|---|---|---|---|---|---|---|---|---|---|---|---|---|
| atg | acc | gcc | gag | aac | gac | aag | atc | cgc | agc | tat | ctg | aag | cgt | gcc | acc | 48 |
| Met | Thr | Ala | Glu | Asn | Asp | Lys | Ile | Arg | Ser | Tyr | Leu | Lys | Arg | Ala | Thr | |
| 1 | | | | 5 | | | | | 10 | | | | | 15 | | |

| | | | | | | | | | | | | | | | |
|---|---|---|---|---|---|---|---|---|---|---|---|---|---|---|---|
| gcc | gaa | ctg | cac | aag | acc | aag | tcc | cgc | ctg | gcc | gag | gtc | gag | tcg | gcg | 96 |
| Ala | Glu | Leu | His | Lys | Thr | Lys | Ser | Arg | Leu | Ala | Glu | Val | Glu | Ser | Ala | |
| | | | 20 | | | | | 25 | | | | | 30 | | | |

| | | | | | | | | | | | | | | | |
|---|---|---|---|---|---|---|---|---|---|---|---|---|---|---|---|
| agc | cgg | gag | ccg | att | gcg | gtc | gtt | ggt | atg | gct | tgt | cgt | tat | ccg | ggt | 144 |
| Ser | Arg | Glu | Pro | Ile | Ala | Val | Val | Gly | Met | Ala | Cys | Arg | Tyr | Pro | Gly | |
| | | 35 | | | | | 40 | | | | | 45 | | | | |

| | | | | | | | | | | | | | | | |
|---|---|---|---|---|---|---|---|---|---|---|---|---|---|---|---|
| ggg | gtg | gcg | gcg | ccg | gag | gat | ttg | tgg | gat | ctg | gtg | gtc | gcg | ggt | acg | 192 |

```
Gly Val Ala Ala Pro Glu Asp Leu Trp Asp Leu Val Ala Gly Thr
         50                  55                  60 gac gcg atc tcc ccg ttc ccc gcc gac cgt ggc tgg gac gtc gag ggg      240
Asp Ala Ile Ser Pro Phe Pro Ala Asp Arg Gly Trp Asp Val Glu Gly
 65                  70                  75                  80 ctg tat gac ccg gac ccc gat gcg gtg ggt cgc agc tat gtg cgt gag      288
Leu Tyr Asp Pro Asp Pro Asp Ala Val Gly Arg Ser Tyr Val Arg Glu
                 85                  90                  95 ggg ggt ttt ctg cac ggg gcg gcc gag ttc gat gcg gag ttc ttc ggt      336
Gly Gly Phe Leu His Gly Ala Ala Glu Phe Asp Ala Glu Phe Phe Gly
            100                 105                 110 gtt tcg ccg cgt gag gcg gcg gcg atg gat ccg cag cag cgg ttg ttg      384
Val Ser Pro Arg Glu Ala Ala Ala Met Asp Pro Gln Gln Arg Leu Leu
        115                 120                 125 ttg gag acg tcg tgg gag gcg ttg gag cgg gcc ggg atc gtg ccg gct      432
Leu Glu Thr Ser Trp Glu Ala Leu Glu Arg Ala Gly Ile Val Pro Ala
130                 135                 140 gcg ctg cgc ggc acc cgc acc gga gtc ttc acc ggc gtg atg tat gac      480
Ala Leu Arg Gly Thr Arg Thr Gly Val Phe Thr Gly Val Met Tyr Asp
145                 150                 155                 160 gac tac gga tcg cag ttc gat tcc gca ccg ccg gag tac gag ggc tac      528
Asp Tyr Gly Ser Gln Phe Asp Ser Ala Pro Pro Glu Tyr Glu Gly Tyr
                165                 170                 175 ctc gtg aat ggc agc gcg ggc agc atc gca tcc ggc cgg gtt gct tac      576
Leu Val Asn Gly Ser Ala Gly Ser Ile Ala Ser Gly Arg Val Ala Tyr
            180                 185                 190 tcc ttg ggt ttg gag ggg ccg gcg ctc acg gtg gat acc gcg tgt tcg      624
Ser Leu Gly Leu Glu Gly Pro Ala Leu Thr Val Asp Thr Ala Cys Ser
        195                 200                 205 tcg tcg ttg gtg gcg ttg cat ctg gcg gtg cag tcg ttg cgg cgg ggt      672
Ser Ser Leu Val Ala Leu His Leu Ala Val Gln Ser Leu Arg Arg Gly
210                 215                 220 gag tgc gat atg gcg ttg gcc ggt ggt gtg acg gtg atg gcg acg ccg      720
Glu Cys Asp Met Ala Leu Ala Gly Gly Val Thr Val Met Ala Thr Pro
225                 230                 235                 240 acg gtg ttt gtg gag ttt tcc cgg cag cgt ggg ttg gct ccc gac ggg      768
Thr Val Phe Val Glu Phe Ser Arg Gln Arg Gly Leu Ala Pro Asp Gly
                245                 250                 255 cgg tgc aag gcg ttt gcg gag ggt gct gat ggt act gct tgg ggt gag      816
Arg Cys Lys Ala Phe Ala Glu Gly Ala Asp Gly Thr Ala Trp Gly Glu
            260                 265                 270 ggt gtt ggt gtg ctg ttg gtg gag cgg ctg tcc gat gcc cgt cgc ctt      864
Gly Val Gly Val Leu Leu Val Glu Arg Leu Ser Asp Ala Arg Arg Leu
        275                 280                 285 ggt cac tcg gtg ttg gcg gtg gtg cgg ggg agt gcg gtt aat cag gac      912
Gly His Ser Val Leu Ala Val Val Arg Gly Ser Ala Val Asn Gln Asp
290                 295                 300 ggt gcc agt aat ggt ttg acg gcg ccc agt ggt ccg gct cag cag agg      960
Gly Ala Ser Asn Gly Leu Thr Ala Pro Ser Gly Pro Ala Gln Gln Arg
305                 310                 315                 320 gtg atc cgt gag gcg ttg gcg gat gcc ggg ttg ggg tcg ggt gat gtg     1008
Val Ile Arg Glu Ala Leu Ala Asp Ala Gly Leu Gly Ser Gly Asp Val
                325                 330                 335 gat gtg gtg gag gcg cat ggt acg ggt acg gcg ttg ggt gat ccg atc     1056
Asp Val Val Glu Ala His Gly Thr Gly Thr Ala Leu Gly Asp Pro Ile
            340                 345                 350 gag gct ggt gcg ttg ctg gcc acg tat ggg cgt gag cgg gtg ggt gat     1104
Glu Ala Gly Ala Leu Leu Ala Thr Tyr Gly Arg Glu Arg Val Gly Asp
        355                 360                 365 ccg ttg tgg ttg ggg tcg ctg aag tcc aac atc ggg cac act cag gcc     1152
```

|  |  |  |  |  |  |  |  |  |  |  |  |  |  |  |
|---|---|---|---|---|---|---|---|---|---|---|---|---|---|---|
| Pro | Leu | Trp | Leu | Gly | Ser | Leu | Lys | Ser | Asn | Ile | Gly | His | Thr | Gln | Ala |
|  | 370 |  |  |  | 375 |  |  |  |  | 380 |  |  |  |  |  |

```
gcc gcg ggt gtg ggt ggt gtc atc aag atg gtg gag gcg ctg cgt cat    1200
Ala Ala Gly Val Gly Gly Val Ile Lys Met Val Glu Ala Leu Arg His
385             390                 395                 400 ggc acg ttg cct cgc act ctc cac gtc gat gct ccc tct tcg aag gtc    1248
Gly Thr Leu Pro Arg Thr Leu His Val Asp Ala Pro Ser Ser Lys Val
                405                 410                 415 gag tgg ggt tgg ggc gcg gtg gag ctg ttg acc gag gct cga gcc tgg    1296
Glu Trp Gly Trp Gly Ala Val Glu Leu Leu Thr Glu Ala Arg Ala Trp
            420                 425                 430 ccc cgg cgg gcg gat cgc aag cgc cgt gcg gcc gtc tcc gcc ttc ggc    1344
Pro Arg Arg Ala Asp Arg Lys Arg Arg Ala Ala Val Ser Ala Phe Gly
        435                 440                 445 gtc agc ggc acc aac gct cat gtc gtc atc gag gaa ccg ccc gcc gag    1392
Val Ser Gly Thr Asn Ala His Val Val Ile Glu Glu Pro Pro Ala Glu
    450                 455                 460 gtg tcg gcc gag tcg ctg gtc gag ttg cct gct ggt gct ggt gct ggt    1440
Val Ser Ala Glu Ser Leu Val Glu Leu Pro Ala Gly Ala Gly Ala Gly
465                 470                 475                 480 gct ggt gct ggt gct ggt gct ggg gtg tct tcg gtt gtg gcg tgg tcg    1488
Ala Gly Ala Gly Ala Gly Ala Gly Val Ser Ser Val Val Ala Trp Ser
                485                 490                 495 ttg tcg gct cgt tcg ggt gag gcg ttg cgg gcg cag gcg gtg cgg ttg    1536
Leu Ser Ala Arg Ser Gly Glu Ala Leu Arg Ala Gln Ala Val Arg Leu
            500                 505                 510 cgt gag cat gtg gag cgt gtt ggg gct gat ccg gtt gat gtt gcc ttt    1584
Arg Glu His Val Glu Arg Val Gly Ala Asp Pro Val Asp Val Ala Phe
        515                 520                 525 tcg ttg gcg gtg acg cgt gcg tcg ttc ggt gag cgt gcg gtg gtc gtt    1632
Ser Leu Ala Val Thr Arg Ala Ser Phe Gly Glu Arg Ala Val Val Val
    530                 535                 540 ggt ggt gac cgt gcg gag ttg ttg gcg ggg ctg ggg gct gtt gct gct    1680
Gly Gly Asp Arg Ala Glu Leu Leu Ala Gly Leu Gly Ala Val Ala Ala
545                 550                 555                 560 ggg gat gcg ctg tcg ggc gtg gtg cgc ggt tcg gcg gtg cgg ggg cga    1728
Gly Asp Ala Leu Ser Gly Val Val Arg Gly Ser Ala Val Arg Gly Arg
                565                 570                 575 aag gtt gcg gct ttg ttt acg ggt cag ggt gcg cag tgg gtt ggt atg    1776
Lys Val Ala Ala Leu Phe Thr Gly Gln Gly Ala Gln Trp Val Gly Met
            580                 585                 590 ggg cgt gag ttg tat ggg ttg gat ggg gtg ttt gct gcg gcg ttg gat    1824
Gly Arg Glu Leu Tyr Gly Leu Asp Gly Val Phe Ala Ala Ala Leu Asp
        595                 600                 605 gag gtt ttg ggt gtg gtg ggg gag gtg ggt ggt tgg tct ttg cgt gag    1872
Glu Val Leu Gly Val Val Gly Glu Val Gly Gly Trp Ser Leu Arg Glu
    610                 615                 620 gtg atg ttt ggt gag ggt ggt gtt ggg gtg ggg ttg ttg gat ggt        1920
Val Met Phe Gly Glu Gly Gly Val Gly Val Gly Leu Leu Asp Gly
625                 630                 635                 640 acg gag ttt gcg cag cct gct ttg ttt gcg ttg gag gtg gcg ttg ttt    1968
Thr Glu Phe Ala Gln Pro Ala Leu Phe Ala Leu Glu Val Ala Leu Phe
                645                 650                 655 cgg gct gtg gag gct cgg ggg gtg cgg gct tcg gtg gtg ttg ggg cat    2016
Arg Ala Val Glu Ala Arg Gly Val Arg Ala Ser Val Val Leu Gly His
            660                 665                 670 tcg gtg ggg gag gtt gct gct gcg tgt gtg gcg ggg gtg ttt tcg ctt    2064
Ser Val Gly Glu Val Ala Ala Ala Cys Val Ala Gly Val Phe Ser Leu
        675                 680                 685 gcg gat gcg gcg cgg ttg gtg gtg gcg cgt ggt cgg ttg atg ggt ggg    2112
```

-continued

```
                Ala Asp Ala Ala Arg Leu Val Val Ala Arg Gly Arg Leu Met Gly Gly
                            690                 695                 700 ttg cct gtg ggt ggg ggg atg ttg tcg gtt cgt gcg tct gag gcc gaa       2160
Leu Pro Val Gly Gly Gly Met Leu Ser Val Arg Ala Ser Glu Ala Glu
705                 710                 715                 720 ctt gct gat gtt gtg gct ggg ttg ggt ggt cgg gtg tcg gtg gct gcg       2208
Leu Ala Asp Val Val Ala Gly Leu Gly Gly Arg Val Ser Val Ala Ala
                725                 730                 735 gtc aat ggt ccg gcg tcg gtg gtg ttg tct ggt gag tgt ggt gcg ttg       2256
Val Asn Gly Pro Ala Ser Val Val Leu Ser Gly Glu Cys Gly Ala Leu
            740                 745                 750 gat gtt gtt gcg gcg cgg ttg ggt ggg cgt ggg gtg gag tgc aag cgg       2304
Asp Val Val Ala Ala Arg Leu Gly Gly Arg Gly Val Glu Cys Lys Arg
        755                 760                 765 ttg gtg gtg tcg cat gcg ttt cat tcg gcg ttg atg gag ccg atg ttg       2352
Leu Val Val Ser His Ala Phe His Ser Ala Leu Met Glu Pro Met Leu
    770                 775                 780 gag gag ttt cgt ggg gtt gct gag agt gtg gag tat cgg cgg ccg tgt       2400
Glu Glu Phe Arg Gly Val Ala Glu Ser Val Glu Tyr Arg Arg Pro Cys
785                 790                 795                 800 gtg ccg gtg gtg tcg aat gtg acg ggt ggg gtg gtt ggg ttt gat gag       2448
Val Pro Val Val Ser Asn Val Thr Gly Gly Val Val Gly Phe Asp Glu
                805                 810                 815 ttg ggt tgt gcc gag tat tgg gtg cgg cat gcg cgg gag gcg gtg cgt       2496
Leu Gly Cys Ala Glu Tyr Trp Val Arg His Ala Arg Glu Ala Val Arg
            820                 825                 830 ttc gct gag ggg ata cgg gct gct cgt gct ctt ggt gtg gat acg ttc       2544
Phe Ala Glu Gly Ile Arg Ala Ala Arg Ala Leu Gly Val Asp Thr Phe
        835                 840                 845 ctg gag gtg ggt ccg cat gcg gtt ttg acg gcg atg gct ggt cag tgt       2592
Leu Glu Val Gly Pro His Ala Val Leu Thr Ala Met Ala Gly Gln Cys
    850                 855                 860 ctt gat gga gag gag gct gac ttg gcg ttt gtg ccg gtc ctg cgg cgt       2640
Leu Asp Gly Glu Glu Ala Asp Leu Ala Phe Val Pro Val Leu Arg Arg
865                 870                 875                 880 gat cgg ccg gca tcg cag acc ttc acc acc gca ctc gcc act ctg cac       2688
Asp Arg Pro Ala Ser Gln Thr Phe Thr Thr Ala Leu Ala Thr Leu His
                885                 890                 895 acc cgg ggc cta ccg gta ccg ccg acg ccc tcg atg cct gcc gcc cgg       2736
Thr Arg Gly Leu Pro Val Pro Pro Thr Pro Ser Met Pro Ala Ala Arg
            900                 905                 910 cgg atc gac ctg ccc acc tac ccc ttc caa cgg aac cgc tac tgg ctg       2784
Arg Ile Asp Leu Pro Thr Tyr Pro Phe Gln Arg Asn Arg Tyr Trp Leu
        915                 920                 925 gcg gcc ccg ccg cgg ccc acg acc ggc ggg gtg tcg gca gcc ggt cag       2832
Ala Ala Pro Pro Arg Pro Thr Thr Gly Gly Val Ser Ala Ala Gly Gln
    930                 935                 940 cgt gcg gtg gag cat ccg ctg ctc gcc gcc gcc gtg gaa ctc ccg ggc       2880
Arg Ala Val Glu His Pro Leu Leu Ala Ala Ala Val Glu Leu Pro Gly
945                 950                 955                 960 gcc ggc acc gag gtg tgg acc ggc cgg atc tcc gcc gcg gac ctc ccc       2928
Ala Gly Thr Glu Val Trp Thr Gly Arg Ile Ser Ala Ala Asp Leu Pro
                965                 970                 975 tgg ctc gcc gac cac ctg gtg tgg gac cgc gga gtg gtc ccc ggg gct       2976
Trp Leu Ala Asp His Leu Val Trp Asp Arg Gly Val Val Pro Gly Ala
            980                 985                 990 gcc ctg ctg gag ttg gtg ctc cag  gtg gga agc cgg atc  gga ctg ccc     3024
Ala Leu Leu Glu Leu Val Leu Gln  Val Gly Ser Arg Ile  Gly Leu Pro
        995                 1000                 1005 cgc gtt  gcc gaa ctg acc ttt  gag acc gcg ctg gcc  tgg gcc acg        3069
```

```
Arg Val Ala Glu Leu Thr Phe Glu Thr Ala Leu Ala Trp Ala Thr
    1010                1015                1020 gac acc ccg ctc cag atc cgg gtc gtc gtg gac gct cct gcc tcc      3114
Asp Thr Pro Leu Gln Ile Arg Val Val Val Asp Ala Pro Ala Ser
    1025                1030                1035 gtc ccc gac ggg gcc cgt gag gtg agc ctt tac tcc cgg ccc gaa      3159
Val Pro Asp Gly Ala Arg Glu Val Ser Leu Tyr Ser Arg Pro Glu
    1040                1045                1050 ccc gtc gcc cgc acc ccg cac ccc gct gga tcc ccg cac ctg gcg      3204
Pro Val Ala Arg Thr Pro His Pro Ala Gly Ser Pro His Leu Ala
    1055                1060                1065 gcg gag cac ggc gac aac ggc tgg acc cgg cac gct tcc ggc gtg      3249
Ala Glu His Gly Asp Asn Gly Trp Thr Arg His Ala Ser Gly Val
    1070                1075                1080 ctc gct ccg gcc gcc gac cat tcc cac gac tcc gac cca gcc gca      3294
Leu Ala Pro Ala Ala Asp His Ser His Asp Ser Asp Pro Ala Ala
    1085                1090                1095 ccc agc acc ttc gcc gaa ctc acc ggt gcc tgg ccg ccc gcc ggc      3339
Pro Ser Thr Phe Ala Glu Leu Thr Gly Ala Trp Pro Pro Ala Gly
    1100                1105                1110 gcc gag cct ctc gac atc gcc gag cag tac tcg ctc ttc gca gcg      3384
Ala Glu Pro Leu Asp Ile Ala Glu Gln Tyr Ser Leu Phe Ala Ala
    1115                1120                1125 gtc gga gtg cgc tac gaa ggc gcc ttc cgt ggg ctg cgc gcg gcg      3429
Val Gly Val Arg Tyr Glu Gly Ala Phe Arg Gly Leu Arg Ala Ala
    1130                1135                1140 tgg cgc cgc ggc gac gag atc ttc gcc gaa gtg cgg tta ccc gat      3474
Trp Arg Arg Gly Asp Glu Ile Phe Ala Glu Val Arg Leu Pro Asp
    1145                1150                1155 gtg cac gcc gcc gac gcc acc cgc tac ggg gtg cat ccc gcc ctg      3519
Val His Ala Ala Asp Ala Thr Arg Tyr Gly Val His Pro Ala Leu
    1160                1165                1170 ctc gac gcg gcc ctg cac ccc atc gcg ctg ctc gac ccg ttg ggc      3564
Leu Asp Ala Ala Leu His Pro Ile Ala Leu Leu Asp Pro Leu Gly
    1175                1180                1185 gac ggc gga cac ggc ctg ctg ccg ttc tcc tgg acc gac gtt cag      3609
Asp Gly Gly His Gly Leu Leu Pro Phe Ser Trp Thr Asp Val Gln
    1190                1195                1200 cac tac ggt tcc ggc gga cac gca ctc cgg gta cgg gtg gct gcc      3654
His Tyr Gly Ser Gly Gly His Ala Leu Arg Val Arg Val Ala Ala
    1205                1210                1215 gcc gac ggc gga gcg gtg tcg atc tcc gtg gtg gac cgc gag ggt      3699
Ala Asp Gly Gly Ala Val Ser Ile Ser Val Val Asp Arg Glu Gly
    1220                1225                1230 gcc cct gtc ctc gcc gcc cgc tcc ctg gcg ctg cgc cgc atc gcc      3744
Ala Pro Val Leu Ala Ala Arg Ser Leu Ala Leu Arg Arg Ile Ala
    1235                1240                1245 gcg gac cgg ctg ccc gcc gcc ccc gcc gct ccc ctg tac cgc atg      3789
Ala Asp Arg Leu Pro Ala Ala Pro Ala Ala Pro Leu Tyr Arg Met
    1250                1255                1260 gac tgg ttg ccg cta ccc gag cga gtg ccc gcc gcc acg gcc gcg      3834
Asp Trp Leu Pro Leu Pro Glu Arg Val Pro Ala Ala Thr Ala Ala
    1265                1270                1275 cgc tgg gcc gtc gtc ggg ccg gcg gcc gaa gtc acc gcg gcc ggg      3879
Arg Trp Ala Val Val Gly Pro Ala Ala Glu Val Thr Ala Ala Gly
    1280                1285                1290 ctg cgc gcc gtc ggc gtc gat gcc cgt gcc cac gtg tcc ccc ctc      3924
Leu Arg Ala Val Gly Val Asp Ala Arg Ala His Val Ser Pro Leu
    1295                1300                1305 ggc gag ccg ctg ccg ccg gag gcc ggt acg gac gcc gaa gtg tgc      3969
```

-continued

| | | | | | | | | | | |
|---|---|---|---|---|---|---|---|---|---|---|
| Gly | Glu | Pro | Leu | Pro | Pro | Glu | Ala | Gly | Thr | Asp | Ala | Glu | Val | Cys |
| | 1310 | | | | 1315 | | | | 1320 | |

```
ctc ctc gac ctg acc gcg gtc gat ggc acg gcg ccc cac ggc ggg      4014
Leu Leu Asp Leu Thr Ala Val Asp Gly Thr Ala Pro His Gly Gly
    1325                1330                1335 ctc ctg gac gag gtg cgc gcg acg gtg cgc cgg gcg ctg gaa gcc      4059
Leu Leu Asp Glu Val Arg Ala Thr Val Arg Arg Ala Leu Glu Ala
1340                1345                1350 gta cag acc ccg ctc gcc ggc act gat ccc ctg acg gac gcg cgt      4104
Val Gln Thr Pro Leu Ala Gly Thr Asp Pro Leu Thr Asp Ala Arg
    1355                1360                1365 acg ggc act cct acc ggc ggg ccg cgg ctc gtc gtc ctc acc cgg      4149
Thr Gly Thr Pro Thr Gly Gly Pro Arg Leu Val Val Leu Thr Arg
    1370                1375                1380 gga gcg gcc ggt ccg gag ggt ggc gcg gcc gat ccg gcg ggc gcc      4194
Gly Ala Ala Gly Pro Glu Gly Gly Ala Ala Asp Pro Ala Gly Ala
1385                1390                1395 gcc gtc tgg ggg ctg atc cgg gtc gcc cag acc gag cag ccc ggc      4239
Ala Val Trp Gly Leu Ile Arg Val Ala Gln Thr Glu Gln Pro Gly
    1400                1405                1410 cgc ttc acc ctg gtc gac atc gac agg gcg aag acg tcg ctg cgg      4284
Arg Phe Thr Leu Val Asp Ile Asp Arg Ala Lys Thr Ser Leu Arg
    1415                1420                1425 acc ctg gcc ggg ctg ccg gcc gcg gac gcc gct cag atc gcg gtg      4329
Thr Leu Ala Gly Leu Pro Ala Ala Asp Ala Ala Gln Ile Ala Val
1430                1435                1440 cgc gac gga cgg gcc acc gtc ccc cgc ctc gta cgg gtg gtc gac      4374
Arg Asp Gly Arg Ala Thr Val Pro Arg Leu Val Arg Val Val Asp
    1445                1450                1455 acc gac agc acc ggt gcc ggg gag ctg gtc gag atg ctg gac ccc      4419
Thr Asp Ser Thr Gly Ala Gly Glu Leu Val Glu Met Leu Asp Pro
1460                1465                1470 aac ggc act gtg ctg atc acc gga ggt acc gga gca ctg gcc gca      4464
Asn Gly Thr Val Leu Ile Thr Gly Gly Thr Gly Ala Leu Ala Ala
    1475                1480                1485 gag acc gca cgg cac ctg gtg gaa cga cac aag gca ggt cgg ctt      4509
Glu Thr Ala Arg His Leu Val Glu Arg His Lys Ala Gly Arg Leu
    1490                1495                1500 ctg ctc gtc agc agg cgc ggt gcg gag gcg ccg ggt gcc gcc gaa      4554
Leu Leu Val Ser Arg Arg Gly Ala Glu Ala Pro Gly Ala Ala Glu
1505                1510                1515 ctg gtg gcg gaa ctc gcc gcc ttg ggc gcc gag gtc acc gtc cgg      4599
Leu Val Ala Glu Leu Ala Ala Leu Gly Ala Glu Val Thr Val Arg
    1520                1525                1530 gcc tgt gac gtc gct gac cgc gac gcg ctg cgc cgc ctg ctc ggt      4644
Ala Cys Asp Val Ala Asp Arg Asp Ala Leu Arg Arg Leu Leu Gly
1535                1540                1545 gag ttg ccc gcc gag cac ccc ctg agc tgt gtg gtg cac acc gcc      4689
Glu Leu Pro Ala Glu His Pro Leu Ser Cys Val Val His Thr Ala
    1550                1555                1560 ggt gtg ctc gat gac ggg gtg ctc tcc gcc cag acg acc gag cgg      4734
Gly Val Leu Asp Asp Gly Val Leu Ser Ala Gln Thr Thr Glu Arg
    1565                1570                1575 atc gac gcc gtg ctg cgt ccc aag gtc gac gcc gcc gtc cac ctg      4779
Ile Asp Ala Val Leu Arg Pro Lys Val Asp Ala Ala Val His Leu
1580                1585                1590 gat cag ctg acc cgt gaa ctc ggg ccg gtg cca ttg gtg ttg tac      4824
Asp Gln Leu Thr Arg Glu Leu Gly Pro Val Pro Leu Val Leu Tyr
    1595                1600                1605 tcc tcg gtc tct gcc tct ctt ggc agc gcc ggc cag gcc ggg tac      4869
Ser Ser Val Ser Ala Ser Leu Gly Ser Ala Gly Gln Ala Gly Tyr
```

```
Ser Ser Val Ser Ala Ser Leu Gly Ser Ala Gly Gln Ala Gly Tyr
    1610             1615             1620 gcc gcg gcc aac gcg ttc ctg gac gcg ttg gcc gcc cgc cgg cgc      4914
Ala Ala Ala Asn Ala Phe Leu Asp Ala Leu Ala Ala Arg Arg Arg
1625             1630             1635 gcc gac ggg cac cct gcg ctg tcg ctc ggc tgg ggc tgg tgg gcc      4959
Ala Asp Gly His Pro Ala Leu Ser Leu Gly Trp Gly Trp Trp Ala
1640             1645             1650 ggt gcg ggc atg gcc acc ggt ctg gag ggc gcc gac gcc gcg cgc      5004
Gly Ala Gly Met Ala Thr Gly Leu Glu Gly Ala Asp Ala Ala Arg
1655             1660             1665 atc cgg cgc tcc ggc atc gtc ccg ctc gac cct gcg gac gcg ctg      5049
Ile Arg Arg Ser Gly Ile Val Pro Leu Asp Pro Ala Asp Ala Leu
1670             1675             1680 gag ctg ctc gac cgg gcg ctg gcc cgg ccc gag ccg gcg ctg ctg      5094
Glu Leu Leu Asp Arg Ala Leu Ala Arg Pro Glu Pro Ala Leu Leu
1685             1690             1695 ccg gta cgg ctc gac ctg ccc gcc ctg cgc gct gcg gcc cgc gcc      5139
Pro Val Arg Leu Asp Leu Pro Ala Leu Arg Ala Ala Ala Arg Ala
1700             1705             1710 acc gcg cca ccg gag gtg ctg cgc gag ctc gcc ggt gtc ccg gcc      5184
Thr Ala Pro Pro Glu Val Leu Arg Glu Leu Ala Gly Val Pro Ala
1715             1720             1725 gat tcc ggg gcc gcg ctg ggt gcc ggg gga cgg gtc ggc aac ggc      5229
Asp Ser Gly Ala Ala Leu Gly Ala Gly Gly Arg Val Gly Asn Gly
1730             1735             1740 caa cgg ccc gac ccg gcc agc ccg gcc gag gca ctg gcg gcc cgg      5274
Gln Arg Pro Asp Pro Ala Ser Pro Ala Glu Ala Leu Ala Ala Arg
1745             1750             1755 ctc gcg ccg cgc tcc gca gcc gag cgc acg gcc ctc ctg ctc gac      5319
Leu Ala Pro Arg Ser Ala Ala Glu Arg Thr Ala Leu Leu Leu Asp
1760             1765             1770 ctg gtg cgt gcc gag gtc gcg gcg gtg ctg ggc cac gga gac ccc      5364
Leu Val Arg Ala Glu Val Ala Ala Val Leu Gly His Gly Asp Pro
1775             1780             1785 gcc gcg gtg ggc gcc ggc cgg tcc ttc aag gac gcc gga ttc gac      5409
Ala Ala Val Gly Ala Gly Arg Ser Phe Lys Asp Ala Gly Phe Asp
1790             1795             1800 tcc ctc acc gcc gtc gac ctc cgc aac cgg ctg aac gcg cgc act      5454
Ser Leu Thr Ala Val Asp Leu Arg Asn Arg Leu Asn Ala Arg Thr
1805             1810             1815 ggg ctg cga ctg ccc gcg acg ctc gtg ttc gac cac ccc aca ccg      5499
Gly Leu Arg Leu Pro Ala Thr Leu Val Phe Asp His Pro Thr Pro
1820             1825             1830 ttg tcc ctc gcc gag ctg ctg cgc gcc gac ctg gag gcg gcc ggc      5544
Leu Ser Leu Ala Glu Leu Leu Arg Ala Asp Leu Glu Ala Ala Gly
1835             1840             1845 ctg gtg ggg gcc acc ggt ccg gcg acg ggc gaa cca acc ggc ccc      5589
Leu Val Gly Ala Thr Gly Pro Ala Thr Gly Glu Pro Thr Gly Pro
1850             1855             1860 gag gac ctg tcc agc gtg ctg gac cgg ttg gag tcc agc ctc acc      5634
Glu Asp Leu Ser Ser Val Leu Asp Arg Leu Glu Ser Ser Leu Thr
1865             1870             1875 gcg acc gac aac ggc gac gcc cgc tcg gcc gcc gcg cgg cgg ttg      5679
Ala Thr Asp Asn Gly Asp Ala Arg Ser Ala Ala Ala Arg Arg Leu
1880             1885             1890 tgc agt ctg ctg gcc atg ctc acc gct ggc tcg ggc gag cat ccg      5724
Cys Ser Leu Leu Ala Met Leu Thr Ala Gly Ser Gly Glu His Pro
1895             1900             1905 ggg cag ggc tcc ggc gaa agc ccc cgg ggt tcc ggc gat gcg gtg      5769
```

```
                                        -continued
Gly Gln Gly Ser Gly Glu Ser Pro Arg Gly Ser Gly Asp Ala Val
        1910            1915            1920 ctc gac cgc ctc caa tcg gcc tcc gac gac gac ttg ttc gac ctt    5814
Leu Asp Arg Leu Gln Ser Ala Ser Asp Asp Asp Leu Phe Asp Leu
    1925            1930            1935 ttc gac agc gat ttc cag tga                                    5835
Phe Asp Ser Asp Phe Gln
    1940

<210> SEQ ID NO 6
<211> LENGTH: 1944
<212> TYPE: PRT
<213> ORGANISM: Streptomyces mycarofaciens

<400> SEQUENCE: 6

Met Thr Ala Glu Asn Asp Lys Ile Arg Ser Tyr Leu Lys Arg Ala Thr
1               5                   10                  15

Ala Glu Leu His Lys Thr Lys Ser Arg Leu Ala Glu Val Glu Ser Ala
            20                  25                  30

Ser Arg Glu Pro Ile Ala Val Val Gly Met Ala Cys Arg Tyr Pro Gly
        35                  40                  45

Gly Val Ala Ala Pro Glu Asp Leu Trp Asp Leu Val Val Ala Gly Thr
    50                  55                  60

Asp Ala Ile Ser Pro Phe Pro Ala Asp Arg Gly Trp Asp Val Glu Gly
65                  70                  75                  80

Leu Tyr Asp Pro Asp Pro Asp Ala Val Gly Arg Ser Tyr Val Arg Glu
                85                  90                  95

Gly Gly Phe Leu His Gly Ala Ala Glu Phe Asp Ala Glu Phe Phe Gly
            100                 105                 110

Val Ser Pro Arg Glu Ala Ala Ala Met Asp Pro Gln Gln Arg Leu Leu
        115                 120                 125

Leu Glu Thr Ser Trp Glu Ala Leu Glu Arg Ala Gly Ile Val Pro Ala
    130                 135                 140

Ala Leu Arg Gly Thr Arg Thr Gly Val Phe Thr Gly Val Met Tyr Asp
145                 150                 155                 160

Asp Tyr Gly Ser Gln Phe Asp Ser Ala Pro Pro Glu Tyr Glu Gly Tyr
                165                 170                 175

Leu Val Asn Gly Ser Ala Gly Ser Ile Ala Ser Gly Arg Val Ala Tyr
            180                 185                 190

Ser Leu Gly Leu Glu Gly Pro Ala Leu Thr Val Asp Thr Ala Cys Ser
        195                 200                 205

Ser Ser Leu Val Ala Leu His Leu Ala Val Gln Ser Leu Arg Arg Gly
    210                 215                 220

Glu Cys Asp Met Ala Leu Ala Gly Gly Val Thr Val Met Ala Thr Pro
225                 230                 235                 240

Thr Val Phe Val Glu Phe Ser Arg Gln Arg Gly Leu Ala Pro Asp Gly
                245                 250                 255

Arg Cys Lys Ala Phe Ala Glu Gly Ala Asp Gly Thr Ala Trp Gly Glu
            260                 265                 270

Gly Val Gly Val Leu Leu Val Glu Arg Leu Ser Asp Ala Arg Arg Leu
        275                 280                 285

Gly His Ser Val Leu Ala Val Arg Gly Ser Ala Val Asn Gln Asp
    290                 295                 300

Gly Ala Ser Asn Gly Leu Thr Ala Pro Ser Gly Pro Ala Gln Gln Arg
305                 310                 315                 320

Val Ile Arg Glu Ala Leu Ala Asp Ala Gly Leu Gly Ser Gly Asp Val
```

-continued

```
                325                 330                 335
Asp Val Val Glu Ala His Gly Thr Gly Thr Ala Leu Gly Asp Pro Ile
                    340                 345                 350
Glu Ala Gly Ala Leu Leu Ala Thr Tyr Gly Arg Glu Arg Val Gly Asp
                355                 360                 365
Pro Leu Trp Leu Gly Ser Leu Lys Ser Asn Ile Gly His Thr Gln Ala
370                 375                 380
Ala Ala Gly Val Gly Gly Val Ile Lys Met Val Glu Ala Leu Arg His
385                 390                 395                 400
Gly Thr Leu Pro Arg Thr Leu His Val Asp Ala Pro Ser Ser Lys Val
                    405                 410                 415
Glu Trp Gly Trp Gly Ala Val Glu Leu Leu Thr Glu Ala Arg Ala Trp
                420                 425                 430
Pro Arg Arg Ala Asp Arg Lys Arg Ala Ala Val Ser Ala Phe Gly
            435                 440                 445
Val Ser Gly Thr Asn Ala His Val Val Ile Glu Glu Pro Pro Ala Glu
450                 455                 460
Val Ser Ala Glu Ser Leu Val Glu Leu Pro Ala Gly Ala Gly Ala Gly
465                 470                 475                 480
Ala Gly Ala Gly Ala Gly Ala Gly Val Ser Val Ala Trp Ser
                    485                 490                 495
Leu Ser Ala Arg Ser Gly Glu Ala Leu Arg Ala Gln Ala Val Arg Leu
                500                 505                 510
Arg Glu His Val Glu Arg Val Gly Ala Asp Pro Val Asp Val Ala Phe
            515                 520                 525
Ser Leu Ala Val Thr Arg Ala Ser Phe Gly Glu Arg Ala Val Val Val
            530                 535                 540
Gly Gly Asp Arg Ala Glu Leu Leu Ala Gly Leu Gly Ala Val Ala Ala
545                 550                 555                 560
Gly Asp Ala Leu Ser Gly Val Val Arg Gly Ser Ala Val Arg Gly Arg
                    565                 570                 575
Lys Val Ala Ala Leu Phe Thr Gly Gln Gly Ala Gln Trp Val Gly Met
                580                 585                 590
Gly Arg Glu Leu Tyr Gly Leu Asp Gly Val Phe Ala Ala Ala Leu Asp
            595                 600                 605
Glu Val Leu Gly Val Val Gly Glu Val Gly Gly Trp Ser Leu Arg Glu
            610                 615                 620
Val Met Phe Gly Glu Gly Gly Val Gly Val Gly Leu Leu Asp Gly
625                 630                 635                 640
Thr Glu Phe Ala Gln Pro Ala Leu Phe Ala Leu Glu Val Ala Leu Phe
                    645                 650                 655
Arg Ala Val Glu Ala Arg Gly Val Arg Ala Ser Val Val Leu Gly His
                660                 665                 670
Ser Val Gly Glu Val Ala Ala Cys Val Ala Gly Val Phe Ser Leu
            675                 680                 685
Ala Asp Ala Ala Arg Leu Val Val Ala Arg Gly Arg Leu Met Gly Gly
690                 695                 700
Leu Pro Val Gly Gly Met Leu Ser Val Arg Ala Ser Glu Ala Glu
705                 710                 715                 720
Leu Ala Asp Val Val Ala Gly Leu Gly Gly Arg Val Ser Val Ala Ala
                    725                 730                 735
Val Asn Gly Pro Ala Ser Val Val Leu Ser Gly Glu Cys Gly Ala Leu
                740                 745                 750
```

-continued

Asp Val Val Ala Ala Arg Leu Gly Gly Arg Gly Val Glu Cys Lys Arg
    755                 760                 765

Leu Val Val Ser His Ala Phe His Ser Ala Leu Met Glu Pro Met Leu
    770                 775                 780

Glu Glu Phe Arg Gly Val Ala Glu Ser Val Glu Tyr Arg Arg Pro Cys
785                 790                 795                 800

Val Pro Val Val Ser Asn Val Thr Gly Val Val Gly Phe Asp Glu
                805                 810                 815

Leu Gly Cys Ala Glu Tyr Trp Val Arg His Ala Arg Glu Ala Val Arg
                820                 825                 830

Phe Ala Glu Gly Ile Arg Ala Ala Arg Ala Leu Gly Val Asp Thr Phe
                835                 840                 845

Leu Glu Val Gly Pro His Ala Val Leu Thr Ala Met Ala Gly Gln Cys
    850                 855                 860

Leu Asp Gly Glu Glu Ala Asp Leu Ala Phe Val Pro Val Leu Arg Arg
865                 870                 875                 880

Asp Arg Pro Ala Ser Gln Thr Phe Thr Thr Ala Leu Ala Thr Leu His
                885                 890                 895

Thr Arg Gly Leu Pro Val Pro Pro Thr Pro Ser Met Pro Ala Ala Arg
                900                 905                 910

Arg Ile Asp Leu Pro Thr Tyr Pro Phe Gln Arg Asn Arg Tyr Trp Leu
                915                 920                 925

Ala Ala Pro Pro Arg Pro Thr Thr Gly Gly Val Ser Ala Ala Gly Gln
930                 935                 940

Arg Ala Val Glu His Pro Leu Leu Ala Ala Ala Val Glu Leu Pro Gly
945                 950                 955                 960

Ala Gly Thr Glu Val Trp Thr Gly Arg Ile Ser Ala Ala Asp Leu Pro
                965                 970                 975

Trp Leu Ala Asp His Leu Val Trp Asp Arg Gly Val Val Pro Gly Ala
                980                 985                 990

Ala Leu Leu Glu Leu Val Leu Gln Val Gly Ser Arg Ile Gly Leu Pro
    995                 1000                1005

Arg Val Ala Glu Leu Thr Phe Glu Thr Ala Leu Ala Trp Ala Thr
    1010                1015                1020

Asp Thr Pro Leu Gln Ile Arg Val Val Asp Ala Pro Ala Ser
    1025                1030                1035

Val Pro Asp Gly Ala Arg Glu Val Ser Leu Tyr Ser Arg Pro Glu
    1040                1045                1050

Pro Val Ala Arg Thr Pro His Pro Ala Gly Ser Pro His Leu Ala
    1055                1060                1065

Ala Glu His Gly Asp Asn Gly Trp Thr Arg His Ala Ser Gly Val
    1070                1075                1080

Leu Ala Pro Ala Ala Asp His Ser His Asp Ser Asp Pro Ala Ala
    1085                1090                1095

Pro Ser Thr Phe Ala Glu Leu Thr Gly Ala Trp Pro Pro Ala Gly
    1100                1105                1110

Ala Glu Pro Leu Asp Ile Ala Glu Gln Tyr Ser Leu Phe Ala Ala
    1115                1120                1125

Val Gly Val Arg Tyr Glu Gly Ala Phe Arg Gly Leu Arg Ala Ala
    1130                1135                1140

Trp Arg Arg Gly Asp Glu Ile Phe Ala Glu Val Arg Leu Pro Asp
    1145                1150                1155

Val His Ala Ala Asp Ala Thr Arg Tyr Gly Val His Pro Ala Leu
    1160                1165                1170

```
Leu Asp Ala Ala Leu His Pro Ile Ala Leu Leu Asp Pro Leu Gly
    1175                1180                1185

Asp Gly Gly His Gly Leu Leu Pro Phe Ser Trp Thr Asp Val Gln
    1190                1195                1200

His Tyr Gly Ser Gly Gly His Ala Leu Arg Val Arg Val Ala Ala
    1205                1210                1215

Ala Asp Gly Gly Ala Val Ser Ile Ser Val Val Asp Arg Glu Gly
    1220                1225                1230

Ala Pro Val Leu Ala Ala Arg Ser Leu Ala Leu Arg Arg Ile Ala
    1235                1240                1245

Ala Asp Arg Leu Pro Ala Ala Pro Ala Ala Pro Leu Tyr Arg Met
    1250                1255                1260

Asp Trp Leu Pro Leu Pro Glu Arg Val Pro Ala Ala Thr Ala Ala
    1265                1270                1275

Arg Trp Ala Val Val Gly Pro Ala Ala Glu Val Thr Ala Ala Gly
    1280                1285                1290

Leu Arg Ala Val Gly Val Asp Ala Arg Ala His Val Ser Pro Leu
    1295                1300                1305

Gly Glu Pro Leu Pro Pro Glu Ala Gly Thr Asp Ala Glu Val Cys
    1310                1315                1320

Leu Leu Asp Leu Thr Ala Val Asp Gly Thr Ala Pro His Gly Gly
    1325                1330                1335

Leu Leu Asp Glu Val Arg Ala Thr Val Arg Arg Ala Leu Glu Ala
    1340                1345                1350

Val Gln Thr Pro Leu Ala Gly Thr Asp Pro Leu Thr Asp Ala Arg
    1355                1360                1365

Thr Gly Thr Pro Thr Gly Gly Pro Arg Leu Val Val Leu Thr Arg
    1370                1375                1380

Gly Ala Ala Gly Pro Glu Gly Gly Ala Ala Asp Pro Ala Gly Ala
    1385                1390                1395

Ala Val Trp Gly Leu Ile Arg Val Ala Gln Thr Glu Gln Pro Gly
    1400                1405                1410

Arg Phe Thr Leu Val Asp Ile Asp Arg Ala Lys Thr Ser Leu Arg
    1415                1420                1425

Thr Leu Ala Gly Leu Pro Ala Ala Asp Ala Ala Gln Ile Ala Val
    1430                1435                1440

Arg Asp Gly Arg Ala Thr Val Pro Arg Leu Val Arg Val Val Asp
    1445                1450                1455

Thr Asp Ser Thr Gly Ala Gly Glu Leu Val Glu Met Leu Asp Pro
    1460                1465                1470

Asn Gly Thr Val Leu Ile Thr Gly Gly Thr Gly Ala Leu Ala Ala
    1475                1480                1485

Glu Thr Ala Arg His Leu Val Glu Arg His Lys Ala Gly Arg Leu
    1490                1495                1500

Leu Leu Val Ser Arg Arg Gly Ala Glu Ala Pro Gly Ala Ala Glu
    1505                1510                1515

Leu Val Ala Glu Leu Ala Ala Leu Gly Ala Glu Val Thr Val Arg
    1520                1525                1530

Ala Cys Asp Val Ala Asp Arg Asp Ala Leu Arg Arg Leu Leu Gly
    1535                1540                1545

Glu Leu Pro Ala Glu His Pro Leu Ser Cys Val Val His Thr Ala
    1550                1555                1560

Gly Val Leu Asp Asp Gly Val Leu Ser Ala Gln Thr Thr Glu Arg
```

```
             1565                1570                1575

Ile Asp Ala Val Leu Arg Pro Lys Val Asp Ala Val His Leu
    1580                1585                1590

Asp Gln Leu Thr Arg Glu Leu Gly Pro Val Pro Leu Val Leu Tyr
    1595                1600                1605

Ser Ser Val Ser Ala Ser Leu Gly Ser Ala Gly Gln Ala Gly Tyr
    1610                1615                1620

Ala Ala Ala Asn Ala Phe Leu Asp Ala Leu Ala Ala Arg Arg Arg
    1625                1630                1635

Ala Asp Gly His Pro Ala Leu Ser Leu Gly Trp Gly Trp Trp Ala
    1640                1645                1650

Gly Ala Gly Met Ala Thr Gly Leu Glu Gly Ala Asp Ala Ala Arg
    1655                1660                1665

Ile Arg Arg Ser Gly Ile Val Pro Leu Asp Pro Ala Asp Ala Leu
    1670                1675                1680

Glu Leu Leu Asp Arg Ala Leu Ala Arg Pro Glu Pro Ala Leu Leu
    1685                1690                1695

Pro Val Arg Leu Asp Leu Pro Ala Leu Arg Ala Ala Arg Ala
    1700                1705                1710

Thr Ala Pro Pro Glu Val Leu Arg Glu Leu Ala Gly Val Pro Ala
    1715                1720                1725

Asp Ser Gly Ala Ala Leu Gly Ala Gly Gly Arg Val Gly Asn Gly
    1730                1735                1740

Gln Arg Pro Asp Pro Ala Ser Pro Ala Glu Ala Leu Ala Ala Arg
    1745                1750                1755

Leu Ala Pro Arg Ser Ala Ala Glu Arg Thr Ala Leu Leu Leu Asp
    1760                1765                1770

Leu Val Arg Ala Glu Val Ala Ala Val Leu Gly His Gly Asp Pro
    1775                1780                1785

Ala Ala Val Gly Ala Gly Arg Ser Phe Lys Asp Ala Gly Phe Asp
    1790                1795                1800

Ser Leu Thr Ala Val Asp Leu Arg Asn Arg Leu Asn Ala Arg Thr
    1805                1810                1815

Gly Leu Arg Leu Pro Ala Thr Leu Val Phe Asp His Pro Thr Pro
    1820                1825                1830

Leu Ser Leu Ala Glu Leu Leu Arg Ala Asp Leu Glu Ala Ala Gly
    1835                1840                1845

Leu Val Gly Ala Thr Gly Pro Ala Thr Gly Glu Pro Thr Gly Pro
    1850                1855                1860

Glu Asp Leu Ser Ser Val Leu Asp Arg Leu Glu Ser Ser Leu Thr
    1865                1870                1875

Ala Thr Asp Asn Gly Asp Ala Arg Ser Ala Ala Ala Arg Arg Leu
    1880                1885                1890

Cys Ser Leu Leu Ala Met Leu Thr Ala Gly Ser Gly Glu His Pro
    1895                1900                1905

Gly Gln Gly Ser Gly Glu Ser Pro Arg Gly Ser Gly Asp Ala Val
    1910                1915                1920

Leu Asp Arg Leu Gln Ser Ala Ser Asp Asp Leu Phe Asp Leu
    1925                1930                1935

Phe Asp Ser Asp Phe Gln
    1940

<210> SEQ ID NO 7
<211> LENGTH: 5847
```

```
<212> TYPE: DNA
<213> ORGANISM: Streptomyces mycarofaciens
<220> FEATURE:
<221> NAME/KEY: CDS
<222> LOCATION: (1)..(5844)

<400> SEQUENCE: 7 atg acc gcc gag aac gac aag atc cgc agc tat ctg aag cgt gcc acc       48
Met Thr Ala Glu Asn Asp Lys Ile Arg Ser Tyr Leu Lys Arg Ala Thr
1               5                   10                  15 gcc gaa ctg cac aag acc aag tcc cgc ctg gcc gag gtc gag tcg gcg       96
Ala Glu Leu His Lys Thr Lys Ser Arg Leu Ala Glu Val Glu Ser Ala
            20                  25                  30 agc cgg gag ccg att gcg gtc gtt ggt atg gct tgt cgt tat ccg ggt      144
Ser Arg Glu Pro Ile Ala Val Val Gly Met Ala Cys Arg Tyr Pro Gly
        35                  40                  45 ggg gtg gcg gcg ccg gag gat ttg tgg gat ctg gtg gtc gcg ggt acg      192
Gly Val Ala Ala Pro Glu Asp Leu Trp Asp Leu Val Val Ala Gly Thr
    50                  55                  60 gac gcg atc tcc ccg ttc ccc gcc gac cgt ggc tgg gac gtc gag ggg      240
Asp Ala Ile Ser Pro Phe Pro Ala Asp Arg Gly Trp Asp Val Glu Gly
65                  70                  75                  80 ctg tat gac ccg gac ccc gat gcg gtg ggt cgc agc tat gtg cgt gag      288
Leu Tyr Asp Pro Asp Pro Asp Ala Val Gly Arg Ser Tyr Val Arg Glu
                85                  90                  95 ggg ggt ttt ctg cac ggg gcg gcc gag ttc gat gcg gag ttc ttc ggt      336
Gly Gly Phe Leu His Gly Ala Ala Glu Phe Asp Ala Glu Phe Phe Gly
            100                 105                 110 gtt tcg ccg cgt gag gcg gcg gcg atg gat ccg cag cag cgg ttg ttg      384
Val Ser Pro Arg Glu Ala Ala Ala Met Asp Pro Gln Gln Arg Leu Leu
        115                 120                 125 ttg gag acg tcg tgg gag gcg ttg gag cgg gcc ggg atc gtg ccg gct      432
Leu Glu Thr Ser Trp Glu Ala Leu Glu Arg Ala Gly Ile Val Pro Ala
    130                 135                 140 gcg ctg cgc ggc acc cgc acc gga gtc ttc acc ggc atc tcc cag cag      480
Ala Leu Arg Gly Thr Arg Thr Gly Val Phe Thr Gly Ile Ser Gln Gln
145                 150                 155                 160 gac tac gcc gcc cag ttg ggg gac gcg gcc gag acc tac ggc ggc cat      528
Asp Tyr Ala Ala Gln Leu Gly Asp Ala Ala Glu Thr Tyr Gly Gly His
                165                 170                 175 gtg ctc acc gga aac ctc gga agt gtg gtc tcc ggc cgg gtt gct tac      576
Val Leu Thr Gly Asn Leu Gly Ser Val Val Ser Gly Arg Val Ala Tyr
            180                 185                 190 tcc ttg ggt ttg gag ggg ccg gcg ctc acg gtg gat acc gcg tgt tcg      624
Ser Leu Gly Leu Glu Gly Pro Ala Leu Thr Val Asp Thr Ala Cys Ser
        195                 200                 205 tcg tcg ttg gtg gcg ttg cat ctg gcg gtg cag tcg ttg cgg cgg ggt      672
Ser Ser Leu Val Ala Leu His Leu Ala Val Gln Ser Leu Arg Arg Gly
    210                 215                 220 gag tgc gat atg gcg ttg gcc ggt ggt gtg acg gtg atg gcg acg ccg      720
Glu Cys Asp Met Ala Leu Ala Gly Gly Val Thr Val Met Ala Thr Pro
225                 230                 235                 240 acg gtg ttt gtg gag ttt tcc cgg cag cgt ggg ttg gcg tcg gat ggg      768
Thr Val Phe Val Glu Phe Ser Arg Gln Arg Gly Leu Ala Ser Asp Gly
                245                 250                 255 cgg tgc aag gcg ttt gcg gag ggt gct gat ggt act gct tgg ggt gag      816
Arg Cys Lys Ala Phe Ala Glu Gly Ala Asp Gly Thr Ala Trp Gly Glu
            260                 265                 270 ggt gtt ggt gtg ctg ttg gtg gag cgg ctg tcc gat gcc cgt cgc ctt      864
Gly Val Gly Val Leu Leu Val Glu Arg Leu Ser Asp Ala Arg Arg Leu
        275                 280                 285
```

-continued

| | | |
|---|---|---|
| ggt cac tcg gtg ttg gcg gtg gtg cgg ggg agt gcg gtt aat cag gac<br>Gly His Ser Val Leu Ala Val Val Arg Gly Ser Ala Val Asn Gln Asp<br>290                      295                        300 | 912 | |
| ggt gcc agt aat ggt ttg acg gcg ccc agt ggt ccg gct cag cag agg<br>Gly Ala Ser Asn Gly Leu Thr Ala Pro Ser Gly Pro Ala Gln Gln Arg<br>305                      310                        315                    320 | 960 | |
| gtg atc cgt gag gcg ttg gcg gat gcc ggg ttg ggg tcg ggt gat gtg<br>Val Ile Arg Glu Ala Leu Ala Asp Ala Gly Leu Gly Ser Gly Asp Val<br>                325                        330                        335 | 1008 | |
| gat gtg gtg gag gcg cat ggt acg ggt acg gcg ttg ggt gat ccg atc<br>Asp Val Val Glu Ala His Gly Thr Gly Thr Ala Leu Gly Asp Pro Ile<br>                     340                        345                        350 | 1056 | |
| gag gct ggt gcg ttg ctg gcc acg tat ggg cgt gag cgg gtg ggt gat<br>Glu Ala Gly Ala Leu Leu Ala Thr Tyr Gly Arg Glu Arg Val Gly Asp<br>                355                        360                        365 | 1104 | |
| ccg ttg tgg ttg ggg tcg ctg aag tcc aac atc ggg cac act cag gcc<br>Pro Leu Trp Leu Gly Ser Leu Lys Ser Asn Ile Gly His Thr Gln Ala<br>370                      375                        380 | 1152 | |
| gcc gcg ggt gtg ggt ggt gtc atc aag atg gtg gag gcg ctg cgt cat<br>Ala Ala Gly Val Gly Gly Val Ile Lys Met Val Glu Ala Leu Arg His<br>385                      390                        395                    400 | 1200 | |
| ggc acg ttg cct cgc act ctc cac gtc gat gct ccc tct tcg aag gtc<br>Gly Thr Leu Pro Arg Thr Leu His Val Asp Ala Pro Ser Ser Lys Val<br>                     405                        410                        415 | 1248 | |
| gag tgg ggt tcg ggt gcg gtg gag ctg ttg acc gag gct cga gcc tgg<br>Glu Trp Gly Ser Gly Ala Val Glu Leu Leu Thr Glu Ala Arg Ala Trp<br>                420                        425                        430 | 1296 | |
| ccc cgg cgg gcg gat cgc aag cgc cgt gcg gcc gtc tcc gcc ttc ggc<br>Pro Arg Arg Ala Asp Arg Lys Arg Arg Ala Ala Val Ser Ala Phe Gly<br>                     435                        440                        445 | 1344 | |
| gtc agc ggc acc aac gct cat gtc gtc atc gag gaa ccg ccc gcc gag<br>Val Ser Gly Thr Asn Ala His Val Val Ile Glu Glu Pro Pro Ala Glu<br>450                      455                        460 | 1392 | |
| gtg tcg gcc gag tcg ctg gtc gag ttg cct gct ggt gct ggt gct ggt<br>Val Ser Ala Glu Ser Leu Val Glu Leu Pro Ala Gly Ala Gly Ala Gly<br>465                      470                        475                    480 | 1440 | |
| gct ggt gct ggt gct ggt gct ggt gct ggg gtg tct tcg gtt<br>Ala Gly Ala Gly Ala Gly Ala Gly Ala Gly Val Ser Ser Val<br>                     485                        490                    495 | 1488 | |
| gtg gcg tgg tcg ttg tcg gct cgt tcg ggt gag gcg ttg cgg gcg cag<br>Val Ala Trp Ser Leu Ser Ala Arg Ser Gly Glu Ala Leu Arg Ala Gln<br>                500                        505                        510 | 1536 | |
| gcg gtg cgg ttg cgt gag cat gtg gag cgt gtt ggg gct gat ccg gtt<br>Ala Val Arg Leu Arg Glu His Val Glu Arg Val Gly Ala Asp Pro Val<br>                     515                        520                        525 | 1584 | |
| gat gtt gcc ttt tcg ttg gcg gtg acg cgt gcg tcg ttc ggt gag cgt<br>Asp Val Ala Phe Ser Leu Ala Val Thr Arg Ala Ser Phe Gly Glu Arg<br>530                      535                        540 | 1632 | |
| gcg gtg gtc gtt ggt ggt gac cgt gcg gag ttg ttg gcg ggg ctg ggg<br>Ala Val Val Val Gly Gly Asp Arg Ala Glu Leu Leu Ala Gly Leu Gly<br>545                      550                        555                    560 | 1680 | |
| gct gtt gct gct ggg gat gcg ctg tcg ggc gtg gtg cgt ggt tcg gcg<br>Ala Val Ala Ala Gly Asp Ala Leu Ser Gly Val Val Arg Gly Ser Ala<br>                     565                        570                        575 | 1728 | |
| gtg cgg ggg cga aag gtt gcg gct ttg ttt acg ggt cag ggt gcg cag<br>Val Arg Gly Arg Lys Val Ala Ala Leu Phe Thr Gly Gln Gly Ala Gln<br>                     580                        585                    590 | 1776 | |
| tgg gtt ggt atg ggg cgt gag ttg tat ggg ttg gat ggg gtg ttt gct<br>Trp Val Gly Met Gly Arg Glu Leu Tyr Gly Leu Asp Gly Val Phe Ala<br>595                      600                        605 | 1824 | |

-continued

| | | |
|---|---|---|
| gcg gcg ttg gat gag gtt ttg ggt gtg gtg ggg gag gtg ggt ggt tgg<br>Ala Ala Leu Asp Glu Val Leu Gly Val Val Gly Glu Val Gly Gly Trp<br>610                      615                    620 | | 1872 |
| tct ttg cgt gag gtg atg ttt ggt gag ggt ggt ggt gtt ggg gtg ggg<br>Ser Leu Arg Glu Val Met Phe Gly Glu Gly Gly Gly Val Gly Val Gly<br>625                      630                    635                    640 | | 1920 |
| ttg ttg gat ggt acg gag ttt gcg cag cct gct ttg ttt gcg ttg gag<br>Leu Leu Asp Gly Thr Glu Phe Ala Gln Pro Ala Leu Phe Ala Leu Glu<br>                  645                    650                    655 | | 1968 |
| gtg gcg ttg ttt cgg gct gtg gag gct cgg ggg gtg cgg gct tcg gtg<br>Val Ala Leu Phe Arg Ala Val Glu Ala Arg Gly Val Arg Ala Ser Val<br>        660                    665                    670 | | 2016 |
| gtg ttg ggg cat tcg gtg ggg gag gtt gct gct gcg tgt gtg gcg ggg<br>Val Leu Gly His Ser Val Gly Glu Val Ala Ala Ala Cys Val Ala Gly<br>    675                    680                    685 | | 2064 |
| gtg ttt tcg ctt gcg gat gcg gcg cgg ttg gtg gtg gcg cgt ggt cgg<br>Val Phe Ser Leu Ala Asp Ala Ala Arg Leu Val Val Ala Arg Gly Arg<br>690                      695                    700 | | 2112 |
| ttg atg ggt ggg ttg cct gtg ggt ggg ggg atg ttg tcg gtt cgt gcg<br>Leu Met Gly Gly Leu Pro Val Gly Gly Gly Met Leu Ser Val Arg Ala<br>705                      710                    715                    720 | | 2160 |
| tct gag gcc gaa ctt gct gat gtt gtg gct ggg ttg ggt ggt cgg gtg<br>Ser Glu Ala Glu Leu Ala Asp Val Val Ala Gly Leu Gly Gly Arg Val<br>                  725                    730                    735 | | 2208 |
| tcg gtg gct gcg gtc aat ggt ccg gcg tcg gtg gtg ttg tct ggt gag<br>Ser Val Ala Ala Val Asn Gly Pro Ala Ser Val Val Leu Ser Gly Glu<br>        740                    745                    750 | | 2256 |
| tgt ggt gcg ttg gat gtt gtt gcg gcg cgg ttg ggt ggg cgt ggg gtg<br>Cys Gly Ala Leu Asp Val Val Ala Ala Arg Leu Gly Gly Arg Gly Val<br>    755                    760                    765 | | 2304 |
| gag tgc aag cgg ttg gtg gtg tcg cat gcg ttt cat tcg gcg ttg atg<br>Glu Cys Lys Arg Leu Val Val Ser His Ala Phe His Ser Ala Leu Met<br>770                      775                    780 | | 2352 |
| gag ccg atg ttg gag gag ttt cgt ggg gtt gct gag agt gtg gag tat<br>Glu Pro Met Leu Glu Glu Phe Arg Gly Val Ala Glu Ser Val Glu Tyr<br>785                      790                    795                    800 | | 2400 |
| cgg cgg ccg tgt gtg ccg gtg gtg tcg aat gtg acg ggt ggg gtg gtt<br>Arg Arg Pro Cys Val Pro Val Val Ser Asn Val Thr Gly Gly Val Val<br>                  805                    810                    815 | | 2448 |
| ggg ttt gat gag ttg ggt tgt gcc gag tat tgg gtg cgg cat gcg cgg<br>Gly Phe Asp Glu Leu Gly Cys Ala Glu Tyr Trp Val Arg His Ala Arg<br>        820                    825                    830 | | 2496 |
| gag gcg gtg cgt ttc gct gag ggg ata cgg gct gct cgt gct ctt ggt<br>Glu Ala Val Arg Phe Ala Glu Gly Ile Arg Ala Ala Arg Ala Leu Gly<br>    835                    840                    845 | | 2544 |
| gtg gat acg ttc ctg gag gtg ggt ccg cat gcg gtt ttg acg gcg atg<br>Val Asp Thr Phe Leu Glu Val Gly Pro His Ala Val Leu Thr Ala Met<br>850                      855                    860 | | 2592 |
| gct ggt cag tgt ctt gat gga gag gag gct gac ttg gcg ttt gtg ccg<br>Ala Gly Gln Cys Leu Asp Gly Glu Glu Ala Asp Leu Ala Phe Val Pro<br>865                      870                    875                    880 | | 2640 |
| gtc ctg cgg cgt gat cgg ccg gca tcg cag acc ttc acc acc gca ctc<br>Val Leu Arg Arg Asp Arg Pro Ala Ser Gln Thr Phe Thr Thr Ala Leu<br>                  885                    890                    895 | | 2688 |
| gcc act ctg cac acc cgg ggc cta ccg gta ccg ccg acg ccc tcg atg<br>Ala Thr Leu His Thr Arg Gly Leu Pro Val Pro Pro Thr Pro Ser Met<br>        900                    905                    910 | | 2736 |
| cct gcc gcc cgg cgg atc gac ctg ccc acc tac ccc ttc caa cgg aac<br>Pro Ala Ala Arg Arg Ile Asp Leu Pro Thr Tyr Pro Phe Gln Arg Asn<br>    915                    920                    925 | | 2784 |

```
                                                           -continued
cgc tac tgg ctg gcg gcc ccg ccg cgg ccc acg acc ggc ggg gtg tcg       2832
Arg Tyr Trp Leu Ala Ala Pro Pro Arg Pro Thr Thr Gly Gly Val Ser
        930                 935                 940 gca gcc ggt cag cgt gcg gtg gag cat ccg ctg ctc gcc gcc gcc gtg       2880
Ala Ala Gly Gln Arg Ala Val Glu His Pro Leu Leu Ala Ala Ala Val
945                 950                 955                 960 gaa ctc ccg ggc gcc ggc acc gag gtg tgg acc ggc cgg atc tcc gcc       2928
Glu Leu Pro Gly Ala Gly Thr Glu Val Trp Thr Gly Arg Ile Ser Ala
                965                 970                 975 gcg gac ctc ccc tgg ctc gcc gac cac ctg gtg tgg gac cgc gga gtg       2976
Ala Asp Leu Pro Trp Leu Ala Asp His Leu Val Trp Asp Arg Gly Val
            980                 985                 990 gtc ccc ggg gct gcc ctg ctg gag ttg gtg ctc cag gtg gga agc cgg       3024
Val Pro Gly Ala Ala Leu Leu Glu Leu Val Leu Gln Val Gly Ser Arg
        995                 1000                1005 atc gga ctg ccc cgc gtt gcc gaa ctg acc ttt gag acc gcg ctg            3069
Ile Gly Leu Pro Arg Val Ala Glu Leu Thr Phe Glu Thr Ala Leu
    1010                1015                1020 gcc tgg gcc acg gac acc ccg ctc cag atc cgg gtc gtc gtg gac            3114
Ala Trp Ala Thr Asp Thr Pro Leu Gln Ile Arg Val Val Val Asp
1025                1030                1035 gct cct gcc tcc gtc ccc gac ggg gcc cgt gag gtg agc ctt tac            3159
Ala Pro Ala Ser Val Pro Asp Gly Ala Arg Glu Val Ser Leu Tyr
    1040                1045                1050 tcc cgg ccc gaa ccc gtc gcc cgc acc ccg cac ccc gct gga tcc            3204
Ser Arg Pro Glu Pro Val Ala Arg Thr Pro His Pro Ala Gly Ser
1055                1060                1065 ccg cac ctg gcg gcg gag cac ggc gac aac ggc tgg acc cgg cac            3249
Pro His Leu Ala Ala Glu His Gly Asp Asn Gly Trp Thr Arg His
    1070                1075                1080 gct tcc ggc gtg ctc gct ccg gcc gcc gac cat tcc cac gac tcc            3294
Ala Ser Gly Val Leu Ala Pro Ala Ala Asp His Ser His Asp Ser
1085                1090                1095 gac cca gcc gca ccc agc acc ttc gcc gaa ctc acc ggt gcc tgg            3339
Asp Pro Ala Ala Pro Ser Thr Phe Ala Glu Leu Thr Gly Ala Trp
    1100                1105                1110 ccg ccc gcc ggc gcc gag cct ctc gac atc gcc gag cag tac tcg            3384
Pro Pro Ala Gly Ala Glu Pro Leu Asp Ile Ala Glu Gln Tyr Ser
1115                1120                1125 ctc ttc gca gcg gtc gga gtg cgc tac gaa ggc gcc ttc cgt ggg            3429
Leu Phe Ala Ala Val Gly Val Arg Tyr Glu Gly Ala Phe Arg Gly
    1130                1135                1140 ctg cgc gcg gcg tgg cgc cgc ggc gac gag atc ttc gcc gaa gtg            3474
Leu Arg Ala Ala Trp Arg Arg Gly Asp Glu Ile Phe Ala Glu Val
1145                1150                1155 cgg tta ccc gat gtg cac gcc gcc gac gcc acc cgc tac ggg gtg            3519
Arg Leu Pro Asp Val His Ala Ala Asp Ala Thr Arg Tyr Gly Val
    1160                1165                1170 cat ccc gcc ctg ctc gac gcg gcc ctg cac ccc atc gcg ctg ctc            3564
His Pro Ala Leu Leu Asp Ala Ala Leu His Pro Ile Ala Leu Leu
1175                1180                1185 gac ccg ttg ggc gac ggc gga cac ggc ctg ctg ccg ttc tcc tgg            3609
Asp Pro Leu Gly Asp Gly Gly His Gly Leu Leu Pro Phe Ser Trp
    1190                1195                1200 acc gac gtt cag cac tac ggt tcc ggc gga cac gca ctc cgg gta            3654
Thr Asp Val Gln His Tyr Gly Ser Gly Gly His Ala Leu Arg Val
1205                1210                1215 cgg gtg gct gcc gcc gac ggc gga gcg gtg tcg atc tcc gtg gtg            3699
Arg Val Ala Ala Ala Asp Gly Gly Ala Val Ser Ile Ser Val Val
    1220                1225                1230
```

```
gac cgc gag ggt gcc cct gtc ctc gcc gcc cgc tcc ctg gcg ctg      3744
Asp Arg Glu Gly Ala Pro Val Leu Ala Ala Arg Ser Leu Ala Leu
    1235                1240                1245 cgc cgc atc gcc gcg gac cgg ctg ccc gcc gcc ccc gcc gct ccc      3789
Arg Arg Ile Ala Ala Asp Arg Leu Pro Ala Ala Pro Ala Ala Pro
    1250                1255                1260 ctg tac cgc atg gac tgg ttg ccg cta ccc gag cga gtg ccc gcc      3834
Leu Tyr Arg Met Asp Trp Leu Pro Leu Pro Glu Arg Val Pro Ala
    1265                1270                1275 gcc acg gcc gcg cgc tgg gcc gtc gtc ggg ccg gcc gcc gaa gtc      3879
Ala Thr Ala Ala Arg Trp Ala Val Val Gly Pro Ala Ala Glu Val
    1280                1285                1290 acc gcg gcc ggg ctg cgc gcc gtc ggc gtc gat gcc cgt gcc cac      3924
Thr Ala Ala Gly Leu Arg Ala Val Gly Val Asp Ala Arg Ala His
    1295                1300                1305 gtg tcc ccc ctc ggc gag ccg ctg ccg ccg gag gcc ggt acg gac      3969
Val Ser Pro Leu Gly Glu Pro Leu Pro Pro Glu Ala Gly Thr Asp
    1310                1315                1320 gcc gaa gtg tgc ctc ctc gac ctg acc gcg gtc gat ggc acg gcg      4014
Ala Glu Val Cys Leu Leu Asp Leu Thr Ala Val Asp Gly Thr Ala
    1325                1330                1335 ccc cac ggc ggg ctc ctg gac gag gtg cgc gcg acg gtg cgc cgg      4059
Pro His Gly Gly Leu Leu Asp Glu Val Arg Ala Thr Val Arg Arg
    1340                1345                1350 gcg ctg gaa gcc gta cag acc ccg ctc gcc ggc act gat ccc ctg      4104
Ala Leu Glu Ala Val Gln Thr Pro Leu Ala Gly Thr Asp Pro Leu
    1355                1360                1365 acg gac gcg cgt acg ggc act cct acc ggc ggg ccg cgg ctc gtc      4149
Thr Asp Ala Arg Thr Gly Thr Pro Thr Gly Gly Pro Arg Leu Val
    1370                1375                1380 gtc ctc acc cgg gga gcg gcc ggt ccg gag ggt ggc gcg gcc gat      4194
Val Leu Thr Arg Gly Ala Ala Gly Pro Glu Gly Gly Ala Ala Asp
    1385                1390                1395 ccg gcg ggc gcc gcc gtc tgg ggg ctg atc cgg gtc gcc cag acc      4239
Pro Ala Gly Ala Ala Val Trp Gly Leu Ile Arg Val Ala Gln Thr
    1400                1405                1410 gag cag ccc ggc cgc ttc acc ctg gtc gac atc gac agg gcg aag      4284
Glu Gln Pro Gly Arg Phe Thr Leu Val Asp Ile Asp Arg Ala Lys
    1415                1420                1425 acg tcg ctg cgg acc ctg gcc ggg ctg ccg gcc gcg gac gcc gct      4329
Thr Ser Leu Arg Thr Leu Ala Gly Leu Pro Ala Ala Asp Ala Ala
    1430                1435                1440 cag atc gcg gtg cgc gac gga cgg gcc acc gtc ccc cgc ctc gta      4374
Gln Ile Ala Val Arg Asp Gly Arg Ala Thr Val Pro Arg Leu Val
    1445                1450                1455 cgg gtg gtc gac acc gac agc acc ggt gcc ggg gag ctg gtc gag      4419
Arg Val Val Asp Thr Asp Ser Thr Gly Ala Gly Glu Leu Val Glu
    1460                1465                1470 atg ctg gac ccc aac ggc act gtg ctg atc acc gga ggt acc gga      4464
Met Leu Asp Pro Asn Gly Thr Val Leu Ile Thr Gly Gly Thr Gly
    1475                1480                1485 gca ctg gcc gca gag acc gca cgg cac ctg gtg gaa cga cac aag      4509
Ala Leu Ala Ala Glu Thr Ala Arg His Leu Val Glu Arg His Lys
    1490                1495                1500 gca ggt cgg ctt ctg ctc gtc agc agg cgc ggt gcg gag gcg ccg      4554
Ala Gly Arg Leu Leu Leu Val Ser Arg Arg Gly Ala Glu Ala Pro
    1505                1510                1515 ggt gcc gcc gaa ctg gtg gcg gaa ctc gcc gcc ttg ggc gcc gag      4599
Gly Ala Ala Glu Leu Val Ala Glu Leu Ala Ala Leu Gly Ala Glu
    1520                1525                1530
```

```
                                                        -continued
gtc acc gtc cgg gcc tgt gac gtc gct gac cgc gac gcg ctg cgc      4644
Val Thr Val Arg Ala Cys Asp Val Ala Asp Arg Asp Ala Leu Arg
    1535                1540                1545 cgc ctg ctc ggt gag ttg ccc gcc gag cac ccc ctg agc tgt gtg      4689
Arg Leu Leu Gly Glu Leu Pro Ala Glu His Pro Leu Ser Cys Val
1550                1555                1560 gtg cac acc gcc ggt gtg ctc gat gac ggg gtg ctc tcc gcc cag      4734
Val His Thr Ala Gly Val Leu Asp Asp Gly Val Leu Ser Ala Gln
1565                1570                1575 acg acc gag cgg atc gac gcc gtg ctc cgt ccc aag gtc gac gcc      4779
Thr Thr Glu Arg Ile Asp Ala Val Leu Arg Pro Lys Val Asp Ala
    1580                1585                1590 gcc gtc cac ctg gat cag ctg acc cgt gaa ctc ggg ccg gtg cca      4824
Ala Val His Leu Asp Gln Leu Thr Arg Glu Leu Gly Pro Val Pro
1595                1600                1605 ttg gtg ttg tac tcc tcg gtc tct gcc tct ctt ggc agc gcc ggc      4869
Leu Val Leu Tyr Ser Ser Val Ser Ala Ser Leu Gly Ser Ala Gly
    1610                1615                1620 cag gcc ggg tac gcc gcg gcc aac gcg ttc ctg gac gcg ttg gcc      4914
Gln Ala Gly Tyr Ala Ala Ala Asn Ala Phe Leu Asp Ala Leu Ala
1625                1630                1635 gcc cgc cgg cgc gcc gac ggg cac cct gcg ctg tcg ctc ggc tgg      4959
Ala Arg Arg Arg Ala Asp Gly His Pro Ala Leu Ser Leu Gly Trp
    1640                1645                1650 ggc tgg tgg gcc ggt gcg ggc atg gcc acc ggt ctg gag ggc gcc      5004
Gly Trp Trp Ala Gly Ala Gly Met Ala Thr Gly Leu Glu Gly Ala
1655                1660                1665 gac gcc gcg cgc atc cgg cgc tcc ggc atc gtc ccg ctc gac cct      5049
Asp Ala Ala Arg Ile Arg Arg Ser Gly Ile Val Pro Leu Asp Pro
    1670                1675                1680 gcg gac gcg ctg gag ctg ctc gac cgg gcg ctg gcc cgg ccc gag      5094
Ala Asp Ala Leu Glu Leu Leu Asp Arg Ala Leu Ala Arg Pro Glu
1685                1690                1695 ccg gcg ctg ctg ccg gta cgg ctc gac ctg ccc gcc ctg cgc gct      5139
Pro Ala Leu Leu Pro Val Arg Leu Asp Leu Pro Ala Leu Arg Ala
    1700                1705                1710 gcg gcc cgc gcc acc gcg cca ccg gag gtg ctg cgc gag ctc gcc      5184
Ala Ala Arg Ala Thr Ala Pro Pro Glu Val Leu Arg Glu Leu Ala
1715                1720                1725 ggt gtc ccg gcc gat tcc ggg gcc gcg ctg ggt gcc ggg gga cgg      5229
Gly Val Pro Ala Asp Ser Gly Ala Ala Leu Gly Ala Gly Gly Arg
    1730                1735                1740 gtc ggc aac ggc caa cgg ccc gac ccg gcc agc ccg gcc gag gca      5274
Val Gly Asn Gly Gln Arg Pro Asp Pro Ala Ser Pro Ala Glu Ala
1745                1750                1755 ctg gcg gcc cgg ctc gcg ccg cgc tcc gca gcc gag cgc acg gcc      5319
Leu Ala Ala Arg Leu Ala Pro Arg Ser Ala Ala Glu Arg Thr Ala
    1760                1765                1770 ctc ctg ctc gac ctg gtg cgt gcc gag gtc gcg gcg gtg ctg ggc      5364
Leu Leu Leu Asp Leu Val Arg Ala Glu Val Ala Ala Val Leu Gly
1775                1780                1785 cac gga gac ccc gcc gcg gtg ggc gcc ggc cgg tcc ttc aag gac      5409
His Gly Asp Pro Ala Ala Val Gly Ala Gly Arg Ser Phe Lys Asp
    1790                1795                1800 gcc gga ttc gac tcc ctc acc gcc gtc gac ctc cgc aac cgg ctg      5454
Ala Gly Phe Asp Ser Leu Thr Ala Val Asp Leu Arg Asn Arg Leu
1805                1810                1815 aac gcg cgc act ggg ctg cga ctg ccc gcg acg ctc gtg ttc gac      5499
Asn Ala Arg Thr Gly Leu Arg Leu Pro Ala Thr Leu Val Phe Asp
    1820                1825                1830
```

```
cac  ccc  aca  ccg  ttg  tcc  ctc  gcc  gag  ctg  ctg  cgc  gcc  gac  ctg        5544
His  Pro  Thr  Pro  Leu  Ser  Leu  Ala  Glu  Leu  Leu  Arg  Ala  Asp  Leu
     1835                1840                     1845 gag  gcg  gcc  ggc  ctg  gtg  ggg  gcc  acc  ggt  ccg  gcg  acg  ggc  gaa        5589
Glu  Ala  Ala  Gly  Leu  Val  Gly  Ala  Thr  Gly  Pro  Ala  Thr  Gly  Glu
     1850                1855                     1860 cca  acc  ggc  ccc  gag  gac  ctg  tcc  agc  gtg  ctg  gac  cgg  ttg  gag        5634
Pro  Thr  Gly  Pro  Glu  Asp  Leu  Ser  Ser  Val  Leu  Asp  Arg  Leu  Glu
     1865                1870                     1875 tcc  agc  ctc  acc  gcg  acc  gac  aac  ggc  gac  gcc  cgc  tcg  gcc  gcc        5679
Ser  Ser  Leu  Thr  Ala  Thr  Asp  Asn  Gly  Asp  Ala  Arg  Ser  Ala  Ala
     1880                1885                     1890 gcg  cgg  cgg  ttg  tgc  agt  ctg  ctg  gcc  atg  ctc  acc  gct  ggc  tcg        5724
Ala  Arg  Arg  Leu  Cys  Ser  Leu  Leu  Ala  Met  Leu  Thr  Ala  Gly  Ser
     1895                1900                     1905 ggc  gag  cat  ccg  ggg  cag  ggc  tcc  ggc  gaa  agc  ccc  cgg  ggt  tcc        5769
Gly  Glu  His  Pro  Gly  Gln  Gly  Ser  Gly  Glu  Ser  Pro  Arg  Gly  Ser
     1910                1915                     1920 ggc  gat  gcg  gtg  ctc  gac  cgc  ctc  caa  tcg  gcc  tcc  gac  gac  gac        5814
Gly  Asp  Ala  Val  Leu  Asp  Arg  Leu  Gln  Ser  Ala  Ser  Asp  Asp  Asp
     1925                1930                     1935 ttg  ttc  gac  ctt  ttc  gac  agc  gat  ttc  cag  tga                             5847
Leu  Phe  Asp  Leu  Phe  Asp  Ser  Asp  Phe  Gln
     1940                1945

<210> SEQ ID NO 8
<211> LENGTH: 1948
<212> TYPE: PRT
<213> ORGANISM: Streptomyces mycarofaciens

<400> SEQUENCE: 8

Met  Thr  Ala  Glu  Asn  Asp  Lys  Ile  Arg  Ser  Tyr  Leu  Lys  Arg  Ala  Thr
1                 5                  10                     15

Ala  Glu  Leu  His  Lys  Thr  Lys  Ser  Arg  Leu  Ala  Glu  Val  Glu  Ser  Ala
            20                  25                     30

Ser  Arg  Glu  Pro  Ile  Ala  Val  Val  Gly  Met  Ala  Cys  Arg  Tyr  Pro  Gly
        35                      40                     45

Gly  Val  Ala  Ala  Pro  Glu  Asp  Leu  Trp  Asp  Leu  Val  Val  Ala  Gly  Thr
    50                      55                     60

Asp  Ala  Ile  Ser  Pro  Phe  Pro  Asp  Arg  Gly  Trp  Asp  Val  Glu  Gly
65                  70                      75                     80

Leu  Tyr  Asp  Pro  Asp  Pro  Asp  Ala  Val  Gly  Arg  Ser  Tyr  Val  Arg  Glu
                85                      90                     95

Gly  Gly  Phe  Leu  His  Gly  Ala  Ala  Glu  Phe  Asp  Ala  Glu  Phe  Phe  Gly
            100                     105                    110

Val  Ser  Pro  Arg  Glu  Ala  Ala  Met  Asp  Pro  Gln  Gln  Arg  Leu  Leu
        115                     120                    125

Leu  Glu  Thr  Ser  Trp  Glu  Ala  Leu  Glu  Arg  Ala  Gly  Ile  Val  Pro  Ala
    130                     135                    140

Ala  Leu  Arg  Gly  Thr  Arg  Thr  Gly  Val  Phe  Thr  Gly  Ile  Ser  Gln  Gln
145                     150                     155                    160

Asp  Tyr  Ala  Ala  Gln  Leu  Gly  Asp  Ala  Ala  Glu  Thr  Tyr  Gly  Gly  His
                165                     170                    175

Val  Leu  Thr  Gly  Asn  Leu  Gly  Ser  Val  Val  Ser  Gly  Arg  Val  Ala  Tyr
            180                     185                    190

Ser  Leu  Gly  Leu  Glu  Gly  Pro  Ala  Leu  Thr  Val  Asp  Thr  Ala  Cys  Ser
        195                     200                    205

Ser  Ser  Leu  Val  Ala  Leu  His  Leu  Ala  Val  Gln  Ser  Leu  Arg  Arg  Gly
```

-continued

```
            210                 215                 220
Glu Cys Asp Met Ala Leu Ala Gly Gly Val Thr Val Met Ala Thr Pro
225                 230                 235                 240

Thr Val Phe Val Glu Phe Ser Arg Gln Arg Gly Leu Ala Ser Asp Gly
                245                 250                 255

Arg Cys Lys Ala Phe Ala Glu Gly Ala Asp Gly Thr Ala Trp Gly Glu
                260                 265                 270

Gly Val Gly Val Leu Leu Val Glu Arg Leu Ser Asp Ala Arg Arg Leu
            275                 280                 285

Gly His Ser Val Leu Ala Val Val Arg Gly Ser Ala Val Asn Gln Asp
        290                 295                 300

Gly Ala Ser Asn Gly Leu Thr Ala Pro Ser Gly Pro Ala Gln Gln Arg
305                 310                 315                 320

Val Ile Arg Glu Ala Leu Ala Asp Ala Gly Leu Ser Gly Asp Val
                325                 330                 335

Asp Val Val Glu Ala His Gly Thr Gly Thr Ala Leu Gly Asp Pro Ile
                340                 345                 350

Glu Ala Gly Ala Leu Leu Ala Thr Tyr Gly Arg Glu Arg Val Gly Asp
            355                 360                 365

Pro Leu Trp Leu Gly Ser Leu Lys Ser Asn Ile Gly His Thr Gln Ala
        370                 375                 380

Ala Gly Val Gly Gly Val Ile Lys Met Val Glu Ala Leu Arg His
385                 390                 395                 400

Gly Thr Leu Pro Arg Thr Leu His Val Asp Ala Pro Ser Ser Lys Val
                405                 410                 415

Glu Trp Gly Ser Gly Ala Val Glu Leu Leu Thr Glu Ala Arg Ala Trp
            420                 425                 430

Pro Arg Arg Ala Asp Arg Lys Arg Ala Ala Val Ser Ala Phe Gly
        435                 440                 445

Val Ser Gly Thr Asn Ala His Val Val Ile Glu Glu Pro Pro Ala Glu
450                 455                 460

Val Ser Ala Glu Ser Leu Val Glu Leu Pro Ala Gly Ala Gly Ala Gly
465                 470                 475                 480

Ala Gly Ala Gly Ala Gly Ala Gly Ala Gly Val Ser Val
                485                 490                 495

Val Ala Trp Ser Leu Ser Ala Arg Ser Gly Glu Ala Leu Arg Ala Gln
            500                 505                 510

Ala Val Arg Leu Arg Glu His Val Glu Arg Val Gly Ala Asp Pro Val
        515                 520                 525

Asp Val Ala Phe Ser Leu Ala Val Thr Arg Ala Ser Phe Gly Glu Arg
530                 535                 540

Ala Val Val Val Gly Gly Asp Arg Ala Glu Leu Leu Ala Gly Leu Gly
545                 550                 555                 560

Ala Val Ala Ala Gly Asp Ala Leu Ser Gly Val Arg Gly Ser Ala
                565                 570                 575

Val Arg Gly Arg Lys Val Ala Ala Leu Phe Thr Gly Gln Gly Ala Gln
            580                 585                 590

Trp Val Gly Met Gly Arg Glu Leu Tyr Gly Leu Asp Gly Val Phe Ala
        595                 600                 605

Ala Ala Leu Asp Glu Val Leu Gly Val Val Gly Val Gly Gly Trp
610                 615                 620

Ser Leu Arg Glu Val Met Phe Gly Glu Gly Gly Val Gly Val Gly
625                 630                 635                 640
```

```
Leu Leu Asp Gly Thr Glu Phe Ala Gln Pro Ala Leu Phe Ala Leu Glu
             645                 650                 655
Val Ala Leu Phe Arg Ala Val Glu Ala Arg Gly Val Arg Ala Ser Val
         660                 665                 670
Val Leu Gly His Ser Val Gly Glu Val Ala Ala Cys Val Ala Gly
     675                 680                 685
Val Phe Ser Leu Ala Asp Ala Ala Arg Leu Val Val Ala Arg Gly Arg
 690                 695                 700
Leu Met Gly Gly Leu Pro Val Gly Gly Met Leu Ser Val Arg Ala
705                 710                 715                 720
Ser Glu Ala Glu Leu Ala Asp Val Val Ala Gly Leu Gly Gly Arg Val
             725                 730                 735
Ser Val Ala Ala Val Asn Gly Pro Ala Ser Val Val Leu Ser Gly Glu
         740                 745                 750
Cys Gly Ala Leu Asp Val Val Ala Ala Arg Leu Gly Gly Arg Gly Val
     755                 760                 765
Glu Cys Lys Arg Leu Val Val Ser His Ala Phe His Ser Ala Leu Met
 770                 775                 780
Glu Pro Met Leu Glu Glu Phe Arg Gly Val Ala Glu Ser Val Glu Tyr
785                 790                 795                 800
Arg Arg Pro Cys Val Pro Val Ser Asn Val Thr Gly Gly Val Val
             805                 810                 815
Gly Phe Asp Glu Leu Gly Cys Ala Glu Tyr Trp Val Arg His Ala Arg
         820                 825                 830
Glu Ala Val Arg Phe Ala Glu Gly Ile Arg Ala Ala Arg Ala Leu Gly
     835                 840                 845
Val Asp Thr Phe Leu Glu Val Gly Pro His Ala Val Leu Thr Ala Met
 850                 855                 860
Ala Gly Gln Cys Leu Asp Gly Glu Ala Asp Leu Ala Phe Val Pro
865                 870                 875                 880
Val Leu Arg Arg Asp Arg Pro Ala Ser Gln Thr Phe Thr Thr Ala Leu
             885                 890                 895
Ala Thr Leu His Thr Arg Gly Leu Pro Val Pro Pro Thr Pro Ser Met
         900                 905                 910
Pro Ala Ala Arg Arg Ile Asp Leu Pro Thr Tyr Pro Phe Gln Arg Asn
     915                 920                 925
Arg Tyr Trp Leu Ala Pro Pro Arg Pro Thr Gly Gly Val Ser
 930                 935                 940
Ala Ala Gly Gln Arg Ala Val Glu His Pro Leu Ala Ala Ala Val
945                 950                 955                 960
Glu Leu Pro Gly Ala Gly Thr Glu Val Trp Thr Gly Arg Ile Ser Ala
             965                 970                 975
Ala Asp Leu Pro Trp Leu Ala Asp His Leu Val Trp Asp Arg Gly Val
         980                 985                 990
Val Pro Gly Ala Ala Leu Leu Glu  Leu Val Leu Gln Val  Gly Ser Arg
     995                 1000                 1005
Ile Gly  Leu Pro Arg Val Ala  Glu Leu Thr Phe Glu  Thr Ala Leu
    1010                 1015                 1020
Ala Trp  Ala Thr Asp Thr Pro  Leu Gln Ile Arg Val  Val Val Asp
    1025                 1030                 1035
Ala Pro  Ala Ser Val Pro Asp  Gly Ala Arg Glu Val  Ser Leu Tyr
    1040                 1045                 1050
Ser Arg  Pro Glu Pro Val Ala  Arg Thr Pro His Pro  Ala Gly Ser
    1055                 1060                 1065
```

| | | | | | | | | | | | |
|---|---|---|---|---|---|---|---|---|---|---|---|
| Pro | His | Leu | Ala | Ala | Glu | His | Gly | Asp | Asn | Gly | Trp | Thr | Arg | His |
| | 1070 | | | | 1075 | | | | 1080 | | |
| Ala | Ser | Gly | Val | Leu | Ala | Pro | Ala | Ala | Asp | His | Ser | His | Asp | Ser |
| | 1085 | | | | 1090 | | | | 1095 | | |
| Asp | Pro | Ala | Ala | Pro | Ser | Thr | Phe | Ala | Glu | Leu | Thr | Gly | Ala | Trp |
| | 1100 | | | | 1105 | | | | 1110 | | |
| Pro | Pro | Ala | Gly | Ala | Glu | Pro | Leu | Asp | Ile | Ala | Glu | Gln | Tyr | Ser |
| | 1115 | | | | 1120 | | | | 1125 | | |
| Leu | Phe | Ala | Ala | Val | Gly | Val | Arg | Tyr | Glu | Gly | Ala | Phe | Arg | Gly |
| | 1130 | | | | 1135 | | | | 1140 | | |
| Leu | Arg | Ala | Ala | Trp | Arg | Arg | Gly | Asp | Glu | Ile | Phe | Ala | Glu | Val |
| | 1145 | | | | 1150 | | | | 1155 | | |
| Arg | Leu | Pro | Asp | Val | His | Ala | Ala | Asp | Ala | Thr | Arg | Tyr | Gly | Val |
| | 1160 | | | | 1165 | | | | 1170 | | |
| His | Pro | Ala | Leu | Leu | Asp | Ala | Ala | Leu | His | Pro | Ile | Ala | Leu | Leu |
| | 1175 | | | | 1180 | | | | 1185 | | |
| Asp | Pro | Leu | Gly | Asp | Gly | Gly | His | Gly | Leu | Leu | Pro | Phe | Ser | Trp |
| | 1190 | | | | 1195 | | | | 1200 | | |
| Thr | Asp | Val | Gln | His | Tyr | Gly | Ser | Gly | Gly | His | Ala | Leu | Arg | Val |
| | 1205 | | | | 1210 | | | | 1215 | | |
| Arg | Val | Ala | Ala | Ala | Asp | Gly | Gly | Ala | Val | Ser | Ile | Ser | Val | Val |
| | 1220 | | | | 1225 | | | | 1230 | | |
| Asp | Arg | Glu | Gly | Ala | Pro | Val | Leu | Ala | Ala | Arg | Ser | Leu | Ala | Leu |
| | 1235 | | | | 1240 | | | | 1245 | | |
| Arg | Arg | Ile | Ala | Ala | Asp | Arg | Leu | Pro | Ala | Ala | Pro | Ala | Ala | Pro |
| | 1250 | | | | 1255 | | | | 1260 | | |
| Leu | Tyr | Arg | Met | Asp | Trp | Leu | Pro | Leu | Pro | Glu | Arg | Val | Pro | Ala |
| | 1265 | | | | 1270 | | | | 1275 | | |
| Ala | Thr | Ala | Ala | Arg | Trp | Ala | Val | Val | Gly | Pro | Ala | Ala | Glu | Val |
| | 1280 | | | | 1285 | | | | 1290 | | |
| Thr | Ala | Ala | Gly | Leu | Arg | Ala | Val | Gly | Val | Asp | Ala | Arg | Ala | His |
| | 1295 | | | | 1300 | | | | 1305 | | |
| Val | Ser | Pro | Leu | Gly | Glu | Pro | Leu | Pro | Pro | Glu | Ala | Gly | Thr | Asp |
| | 1310 | | | | 1315 | | | | 1320 | | |
| Ala | Glu | Val | Cys | Leu | Leu | Asp | Leu | Thr | Ala | Val | Asp | Gly | Thr | Ala |
| | 1325 | | | | 1330 | | | | 1335 | | |
| Pro | His | Gly | Gly | Leu | Leu | Asp | Glu | Val | Arg | Ala | Thr | Val | Arg | Arg |
| | 1340 | | | | 1345 | | | | 1350 | | |
| Ala | Leu | Glu | Ala | Val | Gln | Thr | Pro | Leu | Ala | Gly | Thr | Asp | Pro | Leu |
| | 1355 | | | | 1360 | | | | 1365 | | |
| Thr | Asp | Ala | Arg | Thr | Gly | Thr | Pro | Thr | Gly | Gly | Pro | Arg | Leu | Val |
| | 1370 | | | | 1375 | | | | 1380 | | |
| Val | Leu | Thr | Arg | Gly | Ala | Ala | Gly | Pro | Glu | Gly | Gly | Ala | Ala | Asp |
| | 1385 | | | | 1390 | | | | 1395 | | |
| Pro | Ala | Gly | Ala | Ala | Val | Trp | Gly | Leu | Ile | Arg | Val | Ala | Gln | Thr |
| | 1400 | | | | 1405 | | | | 1410 | | |
| Glu | Gln | Pro | Gly | Arg | Phe | Thr | Leu | Val | Asp | Ile | Asp | Arg | Ala | Lys |
| | 1415 | | | | 1420 | | | | 1425 | | |
| Thr | Ser | Leu | Arg | Thr | Leu | Ala | Gly | Leu | Pro | Ala | Ala | Asp | Ala | Ala |
| | 1430 | | | | 1435 | | | | 1440 | | |
| Gln | Ile | Ala | Val | Arg | Asp | Gly | Arg | Ala | Thr | Val | Pro | Arg | Leu | Val |
| | 1445 | | | | 1450 | | | | 1455 | | |
| Arg | Val | Val | Asp | Thr | Asp | Ser | Thr | Gly | Ala | Gly | Glu | Leu | Val | Glu |

-continued 1460            1465            1470

Met Leu Asp Pro Asn Gly Thr Val Leu Ile Thr Gly Gly Thr Gly
    1475            1480            1485

Ala Leu Ala Ala Glu Thr Ala Arg His Leu Val Glu Arg His Lys
    1490            1495            1500

Ala Gly Arg Leu Leu Leu Val Ser Arg Arg Gly Ala Glu Ala Pro
    1505            1510            1515

Gly Ala Ala Glu Leu Val Ala Glu Leu Ala Ala Leu Gly Ala Glu
    1520            1525            1530

Val Thr Val Arg Ala Cys Asp Val Ala Asp Arg Asp Ala Leu Arg
    1535            1540            1545

Arg Leu Leu Gly Glu Leu Pro Ala Glu His Pro Leu Ser Cys Val
    1550            1555            1560

Val His Thr Ala Gly Val Leu Asp Asp Gly Val Leu Ser Ala Gln
    1565            1570            1575

Thr Thr Glu Arg Ile Asp Ala Val Leu Arg Pro Lys Val Asp Ala
    1580            1585            1590

Ala Val His Leu Asp Gln Leu Thr Arg Glu Leu Gly Pro Val Pro
    1595            1600            1605

Leu Val Leu Tyr Ser Ser Val Ser Ala Ser Leu Gly Ser Ala Gly
    1610            1615            1620

Gln Ala Gly Tyr Ala Ala Ala Asn Ala Phe Leu Asp Ala Leu Ala
    1625            1630            1635

Ala Arg Arg Arg Ala Asp Gly His Pro Ala Leu Ser Leu Gly Trp
    1640            1645            1650

Gly Trp Trp Ala Gly Ala Gly Met Ala Thr Gly Leu Glu Gly Ala
    1655            1660            1665

Asp Ala Ala Arg Ile Arg Arg Ser Gly Ile Val Pro Leu Asp Pro
    1670            1675            1680

Ala Asp Ala Leu Glu Leu Leu Asp Arg Ala Leu Ala Arg Pro Glu
    1685            1690            1695

Pro Ala Leu Leu Pro Val Arg Leu Asp Leu Pro Ala Leu Arg Ala
    1700            1705            1710

Ala Ala Arg Ala Thr Ala Pro Pro Glu Val Leu Arg Glu Leu Ala
    1715            1720            1725

Gly Val Pro Ala Asp Ser Gly Ala Ala Leu Gly Ala Gly Gly Arg
    1730            1735            1740

Val Gly Asn Gly Gln Arg Pro Asp Pro Ala Ser Pro Ala Glu Ala
    1745            1750            1755

Leu Ala Ala Arg Leu Ala Pro Arg Ser Ala Ala Glu Arg Thr Ala
    1760            1765            1770

Leu Leu Leu Asp Leu Val Arg Ala Glu Val Ala Ala Val Leu Gly
    1775            1780            1785

His Gly Asp Pro Ala Ala Val Gly Ala Gly Arg Ser Phe Lys Asp
    1790            1795            1800

Ala Gly Phe Asp Ser Leu Thr Ala Val Asp Leu Arg Asn Arg Leu
    1805            1810            1815

Asn Ala Arg Thr Gly Leu Arg Leu Pro Ala Thr Leu Val Phe Asp
    1820            1825            1830

His Pro Thr Pro Leu Ser Leu Ala Glu Leu Leu Arg Ala Asp Leu
    1835            1840            1845

Glu Ala Ala Gly Leu Val Gly Ala Thr Gly Pro Ala Thr Gly Glu
    1850            1855            1860

-continued

| Pro | Thr | Gly | Pro | Glu | Asp | Leu | Ser | Ser | Val | Leu | Asp | Arg | Leu | Glu |
| | 1865 | | | | 1870 | | | | 1875 | | | | | |

| Ser | Ser | Leu | Thr | Ala | Thr | Asp | Asn | Gly | Asp | Ala | Arg | Ser | Ala | Ala |
| | 1880 | | | | 1885 | | | | 1890 | | | | | |

| Ala | Arg | Arg | Leu | Cys | Ser | Leu | Leu | Ala | Met | Leu | Thr | Ala | Gly | Ser |
| | 1895 | | | | 1900 | | | | 1905 | | | | | |

| Gly | Glu | His | Pro | Gly | Gln | Gly | Ser | Gly | Glu | Ser | Pro | Arg | Gly | Ser |
| | 1910 | | | | 1915 | | | | 1920 | | | | | |

| Gly | Asp | Ala | Val | Leu | Asp | Arg | Leu | Gln | Ser | Ala | Ser | Asp | Asp | Asp |
| | 1925 | | | | 1930 | | | | 1935 | | | | | |

| Leu | Phe | Asp | Leu | Phe | Asp | Ser | Asp | Phe | Gln |
| | 1940 | | | | 1945 | | | | |

<210> SEQ ID NO 9
<211> LENGTH: 20
<212> TYPE: DNA
<213> ORGANISM: Artificial
<220> FEATURE:
<223> OTHER INFORMATION: Synthetic primer

<400> SEQUENCE: 9
gtgatgtatg acgactacgg                                                    20

<210> SEQ ID NO 10
<211> LENGTH: 20
<212> TYPE: DNA
<213> ORGANISM: Artificial
<220> FEATURE:
<223> OTHER INFORMATION: Synthetic primer

<400> SEQUENCE: 10
aaacctcgga agtgtggtct                                                    20

<210> SEQ ID NO 11
<211> LENGTH: 20
<212> TYPE: DNA
<213> ORGANISM: Artificial
<220> FEATURE:
<223> OTHER INFORMATION: Synthetic primer

<400> SEQUENCE: 11
atcgagggcg tcggcggtac                                                    20

<210> SEQ ID NO 12
<211> LENGTH: 426
<212> TYPE: PRT
<213> ORGANISM: Streptomyces mycarofaciens

<400> SEQUENCE: 12

| Glu | Pro | Ile | Ala | Val | Val | Gly | Met | Ala | Cys | Arg | Tyr | Pro | Gly | Gly | Val |
| 1 | | | | 5 | | | | | 10 | | | | | 15 | |

| Ala | Ala | Pro | Glu | Glu | Leu | Trp | Asp | Leu | Val | Ala | Gly | Gly | Gly | His | Ala |
| | | | 20 | | | | | 25 | | | | | 30 | | |

| Ile | Ser | Pro | Leu | Pro | Ala | Asn | Arg | Gly | Trp | Asp | Leu | Glu | Gly | Leu | Tyr |
| | | 35 | | | | | 40 | | | | | 45 | | | |

| Asp | Pro | Glu | Pro | Gly | Val | Pro | Gly | Lys | Ser | Tyr | Val | Arg | Glu | Gly | Gly |
| | 50 | | | | | 55 | | | | | 60 | | | | |

| Phe | Leu | His | Gly | Ala | Ala | Glu | Phe | Asp | Ala | Glu | Phe | Phe | Gly | Val | Ser |
| 65 | | | | | 70 | | | | | 75 | | | | | 80 |

| Pro | Arg | Glu | Ala | Ala | Ala | Met | Asp | Pro | Gln | Gln | Arg | Leu | Leu | Leu | Glu |
| | | | | 85 | | | | | 90 | | | | | 95 | |

Thr Ser Trp Glu Ala Leu Glu Arg Ala Gly Ile Val Pro Ala Ala Leu
        100                 105                 110

Arg Gly Thr Arg Thr Gly Val Phe Thr Gly Ile Ser Gln Gln Asp Tyr
    115                 120                 125

Ala Ala Gln Leu Gly Asp Ala Ala Glu Thr Tyr Gly Gly His Val Leu
130                 135                 140

Thr Gly Asn Leu Gly Ser Val Val Ser Gly Arg Val Ala Tyr Ser Leu
145                 150                 155                 160

Gly Leu Glu Gly Pro Ala Leu Thr Val Asp Thr Ala Cys Ser Ser Ser
                165                 170                 175

Leu Val Ala Leu His Leu Ala Val Gln Ser Leu Arg Arg Gly Glu Cys
            180                 185                 190

Asp Met Ala Leu Ala Gly Gly Val Thr Val Met Ala Thr Pro Thr Val
        195                 200                 205

Phe Val Glu Phe Ser Arg Gln Arg Gly Leu Ala Ser Asp Gly Arg Cys
    210                 215                 220

Lys Ala Phe Ala Glu Gly Ala Asp Gly Thr Ala Trp Gly Glu Gly Val
225                 230                 235                 240

Gly Val Leu Leu Val Glu Arg Leu Ser Asp Ala Arg Leu Gly His
                245                 250                 255

Ser Val Leu Ala Val Val Arg Gly Ser Ala Val Asn Gln Asp Gly Ala
            260                 265                 270

Ser Asn Gly Leu Thr Ala Pro Ser Gly Pro Ala Gln Gln Arg Val Ile
        275                 280                 285

Arg Glu Ala Leu Ala Asp Ala Gly Leu Gly Ser Gly Asp Val Asp Val
    290                 295                 300

Val Glu Ala His Gly Thr Gly Thr Ala Leu Gly Asp Pro Ile Glu Ala
305                 310                 315                 320

Gly Ala Leu Leu Ala Thr Tyr Gly Arg Glu Arg Val Gly Asp Pro Leu
                325                 330                 335

Trp Leu Gly Ser Leu Lys Ser Asn Ile Gly His Thr Gln Ala Ala Ala
            340                 345                 350

Gly Val Gly Gly Val Ile Lys Met Val Glu Ala Leu Arg His Gly Thr
        355                 360                 365

Leu Pro Arg Thr Leu His Val Asp Ala Pro Ser Ser Lys Val Glu Trp
    370                 375                 380

Gly Ser Gly Ala Val Glu Leu Leu Thr Glu Ala Arg Ala Trp Pro Arg
385                 390                 395                 400

Arg Ala Asp Arg Lys Arg Arg Ala Ala Val Ser Ala Phe Gly Val Ser
                405                 410                 415

Gly Thr Asn Ala His Val Val Ile Glu Glu
            420                 425

<210> SEQ ID NO 13
<211> LENGTH: 426
<212> TYPE: PRT
<213> ORGANISM: Streptomyces mycarofaciens

<400> SEQUENCE: 13

Glu Pro Ile Ala Val Val Gly Met Ala Cys Arg Tyr Pro Gly Gly Val
1               5                   10                  15

Ala Ala Pro Glu Asp Leu Trp Asp Leu Val Val Ala Gly Thr Asp Ala
            20                  25                  30

Ile Ser Pro Phe Pro Ala Asp Arg Gly Trp Asp Val Glu Gly Leu Tyr
        35                  40                  45

-continued

Asp Pro Asp Pro Asp Ala Val Gly Arg Ser Tyr Val Arg Glu Gly Gly
         50                  55                  60

Phe Leu His Gly Ala Ala Glu Phe Asp Ala Glu Phe Phe Gly Val Ser
 65                  70                  75                  80

Pro Arg Glu Ala Ala Met Asp Pro Gln Gln Arg Leu Leu Leu Glu
                 85                  90                  95

Thr Ser Trp Glu Ala Leu Glu Arg Ala Gly Ile Val Pro Ala Ala Leu
                100                 105                 110

Arg Gly Thr Arg Thr Gly Val Phe Thr Gly Ile Ser Gln Gln Asp Tyr
            115                 120                 125

Ala Ala Gln Leu Gly Asp Ala Ala Glu Thr Tyr Gly Gly His Val Leu
        130                 135                 140

Thr Gly Asn Leu Gly Ser Val Val Ser Gly Arg Val Ala Tyr Ser Leu
145                 150                 155                 160

Gly Leu Glu Gly Pro Ala Leu Thr Val Asp Thr Ala Cys Ser Ser Ser
                165                 170                 175

Leu Val Ala Leu His Leu Ala Val Gln Ser Leu Arg Arg Gly Glu Cys
            180                 185                 190

Asp Met Ala Leu Ala Gly Gly Val Thr Val Met Ala Thr Pro Thr Val
        195                 200                 205

Phe Val Glu Phe Ser Arg Gln Arg Gly Leu Ala Ser Asp Gly Arg Cys
    210                 215                 220

Lys Ala Phe Ala Glu Gly Ala Asp Gly Thr Ala Trp Gly Glu Gly Val
225                 230                 235                 240

Gly Val Leu Leu Val Glu Arg Leu Ser Asp Ala Arg Leu Gly His
                245                 250                 255

Ser Val Leu Ala Val Val Arg Gly Ser Ala Val Asn Gln Asp Gly Ala
            260                 265                 270

Ser Asn Gly Leu Thr Ala Pro Ser Gly Pro Ala Gln Gln Arg Val Ile
        275                 280                 285

Arg Glu Ala Leu Ala Asp Ala Gly Leu Gly Ser Gly Asp Val Asp Val
    290                 295                 300

Val Glu Ala His Gly Thr Gly Thr Ala Leu Gly Asp Pro Ile Glu Ala
305                 310                 315                 320

Gly Ala Leu Leu Ala Thr Tyr Gly Arg Glu Arg Val Gly Asp Pro Leu
                325                 330                 335

Trp Leu Gly Ser Leu Lys Ser Asn Ile Gly His Thr Gln Ala Ala Ala
            340                 345                 350

Gly Val Gly Gly Val Ile Lys Met Val Glu Ala Leu Arg His Gly Thr
        355                 360                 365

Leu Pro Arg Thr Leu His Val Asp Ala Pro Ser Ser Lys Val Glu Trp
    370                 375                 380

Gly Ser Gly Ala Val Glu Leu Leu Thr Glu Ala Arg Ala Trp Pro Arg
385                 390                 395                 400

Arg Ala Asp Arg Lys Arg Arg Ala Ala Val Ser Ala Phe Gly Val Ser
                405                 410                 415

Gly Thr Asn Ala His Val Val Ile Glu Glu
            420                 425

<210> SEQ ID NO 14
<211> LENGTH: 426
<212> TYPE: PRT
<213> ORGANISM: Streptomyces mycarofaciens

<400> SEQUENCE: 14

```
-continued

Glu Pro Ile Ala Val Gly Met Ala Cys Arg Tyr Pro Gly Gly Val
1               5                   10                  15

Ala Ala Pro Glu Asp Leu Trp Asp Leu Val Ala Gly Thr Asp Ala
            20                  25                  30

Ile Ser Pro Phe Pro Ala Asp Arg Gly Trp Asp Val Glu Gly Leu Tyr
            35                  40                  45

Asp Pro Asp Pro Asp Ala Val Gly Arg Ser Tyr Val Arg Glu Gly Gly
50                      55                  60

Phe Leu His Gly Ala Ala Glu Phe Asp Ala Glu Phe Phe Gly Val Ser
65                  70                  75                  80

Pro Arg Glu Ala Ala Ala Met Asp Pro Gln Gln Arg Leu Leu Leu Glu
                85                  90                  95

Thr Ser Trp Glu Ala Leu Glu Arg Ala Gly Ile Val Pro Ala Ala Leu
            100                 105                 110

Arg Gly Thr Arg Thr Gly Val Phe Thr Gly Val Met Tyr Asp Asp Tyr
            115                 120                 125

Gly Ser Gln Phe Asp Ser Ala Pro Pro Glu Tyr Glu Gly Tyr Leu Val
        130                 135                 140

Asn Gly Ser Ala Gly Ser Ile Ala Ser Gly Arg Val Ala Tyr Ser Leu
145                 150                 155                 160

Gly Leu Glu Gly Pro Ala Leu Thr Val Asp Thr Ala Cys Ser Ser Ser
                165                 170                 175

Leu Val Ala Leu His Leu Ala Val Gln Ser Leu Arg Arg Gly Glu Cys
            180                 185                 190

Asp Met Ala Leu Ala Gly Gly Val Thr Val Met Ala Thr Pro Thr Val
            195                 200                 205

Phe Val Glu Phe Ser Arg Gln Arg Gly Leu Ala Pro Asp Gly Arg Cys
            210                 215                 220

Lys Ala Phe Ala Glu Gly Ala Asp Gly Thr Ala Trp Gly Glu Gly Val
225                 230                 235                 240

Gly Val Leu Leu Val Glu Arg Leu Ser Asp Ala Arg Arg Leu Gly His
                245                 250                 255

Ser Val Leu Ala Val Val Arg Gly Ser Ala Val Asn Gln Asp Gly Ala
            260                 265                 270

Ser Asn Gly Leu Thr Ala Pro Ser Gly Pro Ala Gln Gln Arg Val Ile
            275                 280                 285

Arg Glu Ala Leu Ala Asp Ala Gly Leu Gly Ser Gly Asp Val Asp Val
290                 295                 300

Val Glu Ala His Gly Thr Gly Thr Ala Leu Gly Asp Pro Ile Glu Ala
305                 310                 315                 320

Gly Ala Leu Leu Ala Thr Tyr Gly Arg Glu Arg Val Gly Asp Pro Leu
            325                 330                 335

Trp Leu Gly Ser Leu Lys Ser Asn Ile Gly His Thr Gln Ala Ala Ala
            340                 345                 350

Gly Val Gly Gly Val Ile Lys Met Val Glu Ala Leu Arg His Gly Thr
            355                 360                 365

Leu Pro Arg Thr Leu His Val Asp Ala Pro Ser Ser Lys Val Glu Trp
            370                 375                 380

Gly Trp Gly Ala Val Glu Leu Leu Thr Glu Ala Arg Ala Trp Pro Arg
385                 390                 395                 400
```

```
Arg Ala Asp Arg Lys Arg Arg Ala Ala Val Ser Ala Phe Gly Val Ser
                405             410                 415

Gly Thr Asn Ala His Val Val Ile Glu Glu
            420             425
```